(12) United States Patent
Nickolaus et al.

(10) Patent No.: US 8,592,400 B2
(45) Date of Patent: Nov. 26, 2013

(54) DRUG COMBINATIONS CONTAINING PDE4 INHIBITORS AND NSAIDS

(75) Inventors: Peter Nickolaus, Warthausen (DE); Rolf Goeggel, Ulm (DE); Daniel Peter, Ummendorf (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 190 days.

(21) Appl. No.: 13/201,262

(22) PCT Filed: Feb. 18, 2010

(86) PCT No.: PCT/EP2010/052077
§ 371 (c)(1),
(2), (4) Date: Sep. 29, 2011

(87) PCT Pub. No.: WO2010/097332
PCT Pub. Date: Sep. 2, 2010

(65) Prior Publication Data
US 2012/0028932 A1    Feb. 2, 2012

(30) Foreign Application Priority Data

Feb. 27, 2009  (EP) .................................... 09153853
Jul. 22, 2009   (EP) .................................... 09166127

(51) Int. Cl.
*A61K 31/54*   (2006.01)
*A61K 31/501*  (2006.01)
*A61K 31/497*  (2006.01)

(52) U.S. Cl.
USPC ................... 514/161; 514/226.5; 514/252.02; 514/252.16

(58) Field of Classification Search
USPC ..................... 514/161, 226.5, 252.02, 252.16
See application file for complete search history.

(56) References Cited

U.S. PATENT DOCUMENTS

| 7,511,045 | B2 | 3/2009 | Hoenke et al. |
| 7,723,341 | B2 | 5/2010 | Hoenke et al. |
| 2007/0259846 | A1 | 11/2007 | Hoenke et al. |
| 2008/0096882 | A1 | 4/2008 | Pouzet et al. |
| 2009/0186875 | A1 | 7/2009 | Hoenke et al. |
| 2010/0197656 | A1 | 8/2010 | Hoenke et al. |
| 2010/0305102 | A1 | 12/2010 | Pouzet et al. |
| 2011/0028441 | A1 | 2/2011 | Pouzet et al. |

FOREIGN PATENT DOCUMENTS

| CA | 2 605 161 A1 | 10/2006 |
| CA | 2 647 243 A1 | 10/2007 |
| CA | 2 702 447 A1 | 4/2009 |
| CA | 2 702 524 A1 | 4/2009 |
| WO | 03/024489 A2 | 3/2003 |
| WO | 2006/111549 A1 | 10/2006 |
| WO | 2007/118793 A1 | 10/2007 |
| WO | 2009/050242 A2 | 4/2009 |
| WO | 2009/053268 A1 | 4/2009 |

OTHER PUBLICATIONS

International Search Report for PCT/EP2010/050925 mailed Mar. 29, 2010.

*Primary Examiner* — Raymond Henley, III
(74) *Attorney, Agent, or Firm* — Michael P. Morris; Timothy X. Witkowski

(57) ABSTRACT

Drug combinations which contain a PDE4-inhibitor and a non-steroidal anti-inflammatory drug (NSAID), processes for preparing them, and their use in treating in particular respiratory complaints such as COPD, chronic sinusitis, and asthma. The PDE4 inhibitors of the drug combinations include compounds of general formula 1 wherein X is SO or $SO_2$, but preferably SO, $R^3$ is an optionally substituted, mono- or bicyclic, unsaturated, partly saturated or saturated heterocyclic group or an optionally substituted, mono- or bicyclic heteroaryl, and $R^1$ and $R^2$ have the meanings given in claim 2.

22 Claims, 4 Drawing Sheets

Körpergewicht = body weight
zu Tag 1 = on day 1
Uhr = o'clock or hours, i.e. 8 Uhr = 8 o'clock or 0800 hours
Tag = Day
Kontrolle = control Figure 1B: Roflumilast group compared with the control group and the and roflumilast + diclofenac group; and diclofenac group compared with the control group (statistics: One-way analysis of variance; ns= not significant; *** = p < 0.001).

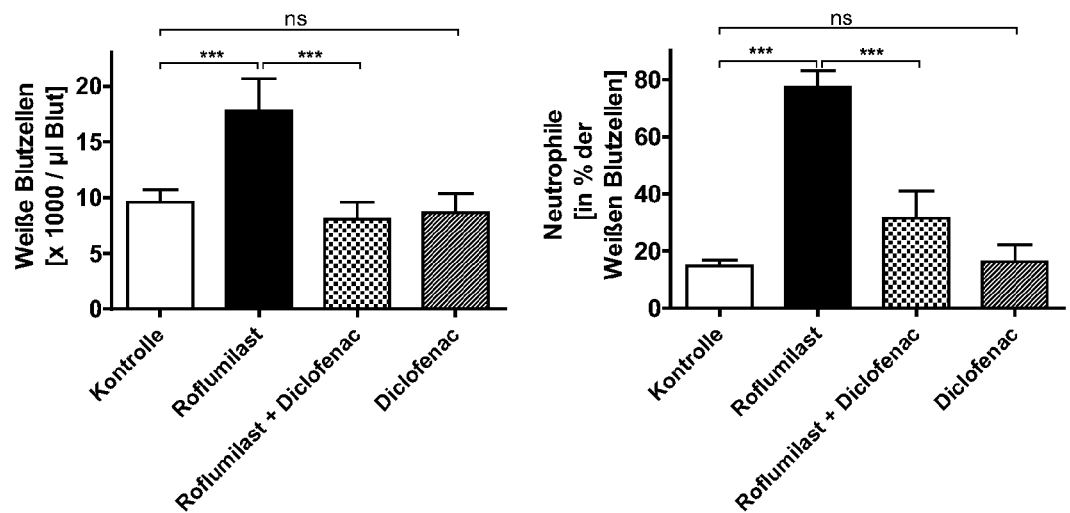

Weiße Blutzellen = white blood cells
Blut = blood
Kontrolle = control
Neutrophilie = neutrophils
in % der Weißen Blutzellen = as a percentage of the white blood cells Körpergewicht = body weight
zu Tag 1 = on day 1
Uhr = o'clock or hours, i.e. 8 Uhr = 8 o'clock or 0800 hours
Tag = Day Figure 2B: Roflumilast group compared with the control group, the roflumilast + SC-560 group and the roflumilast + lumiracoxib group; also the SC-560 group and lumiracoxib group compared with the control group (statistics: One-way analysis of variance; ns = not significant; * = $p < 0.05$; *** = $p < 0.001$).

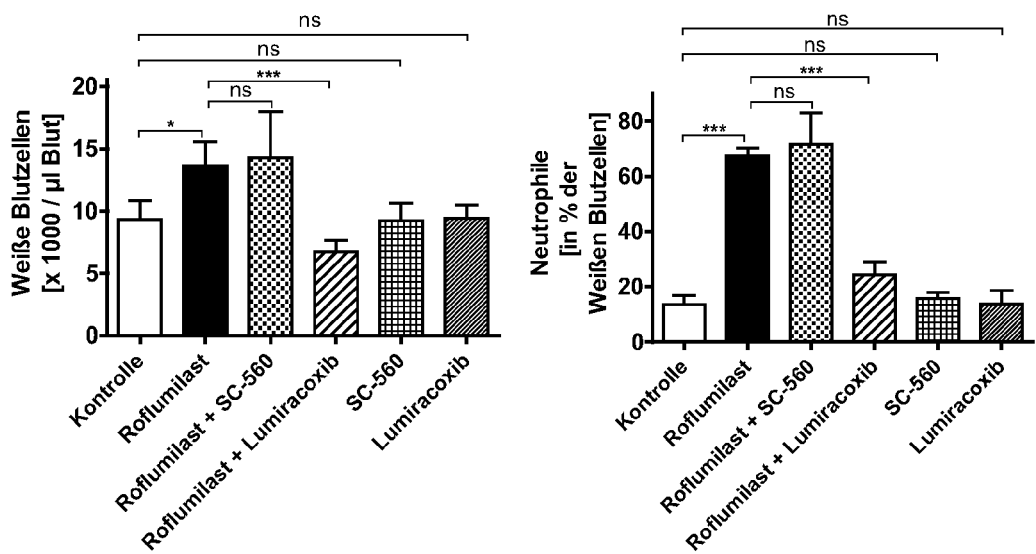

Weiße Blutzellen = white blood cells
Blut = blood
Kontrolle = control
Neutrophilie = neutrophils
in % der Weißen Blutzellen = as a percentage of the white blood cells

DRUG COMBINATIONS CONTAINING PDE4 INHIBITORS AND NSAIDS

This application is the national phase entry under 35 U.S.C. §371 of International Application No. PCT/EP2010/052077, filed Feb. 18, 2010, which claims priority to European Patent Application Nos. 09153853.8, filed Feb. 27, 2009 and 09166127.2, filed Jul. 22, 2009, the contents of which are hereby incorporated by reference in their entireties.

The present invention relates to new drug combinations which contain, in addition to one or more PDE4-inhibitors, at least one NSAID (=non-steroidal anti-inflammatory drug) (2), processes for preparing them and their use for treating in particular respiratory complaints such as for example COPD, chronic sinusitis and asthma.

The invention relates particularly to those drug combinations which comprise, in addition to one or more, preferably one PDE4 inhibitor of general formula 1

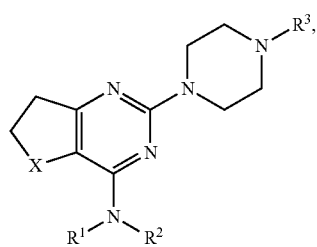

wherein X is SO or $SO_2$, but preferably SO, $R^3$ is an optionally substituted, mono- or bicyclic, unsaturated, partly saturated or saturated heterocyclic group or an optionally substituted, mono- or bicyclic heteroaryl, and $R^1$ and $R^2$ have the meanings given in claim 2, at least one NSAID, the preparation thereof and use thereof for the treatment of respiratory complaints.

PRIOR ART

EP 07118911.2 discloses heterocycle-substituted piperazino-dihydrothienopyrimidines of formula 1 as PDE4-inhibitors, the preparation thereof and the use thereof for the treatment of respiratory complaints.

It is also known that many "1st generation" PDE4-inhibitors such as rolipram, for example, lead to undesirable side effects. Consequently, it was an object of the present invention to provide a drug or drug combination containing a PDE4 inhibitor which has a low side-effect profile.

DESCRIPTION OF THE INVENTION

Surprisingly it has now been found that drug combinations that—in addition to a PDE4 inhibitor and in particular in addition to the dihydrothienopyrimidinesulphoxides of formula 1 known as PDE4-inhibitors wherein $R^3$ denotes a mono- or bicyclic, unsaturated, partly saturated or saturated heterocyclic group or a mono- or bicyclic heteroaryl (1)— also contain at least one NSAID (2), have a significantly lower PDE4-mediated side effect profile compared with a drug that contains the corresponding PDE4 inhibitor or the corresponding dihydrothienopyrimidinesulphoxide of formula 1 on its own. Consequently, the dosage of the corresponding dihydrothienopyrimidinesulphoxide of formula 1 (as PDE4 inhibitor) may turn out to be significantly higher, thus simultaneously increasing its effectiveness in the treatment of for example respiratory complaints such as in particular COPD, chronic sinusitis and asthma while simultaneously retaining a low side effect profile. This therefore gives a larger therapeutic window for the PDE4 inhibitor used.

The present invention therefore relates to a novel drug combination which contains, in addition to one or more PDE4-inhibitors, at least one NSAID (=non-steroidal anti-inflammatory drug) (2).

The present invention preferably relates to drug combinations which, in addition to one or more, preferably one compound of general formula 1 as PDE4 inhibitor

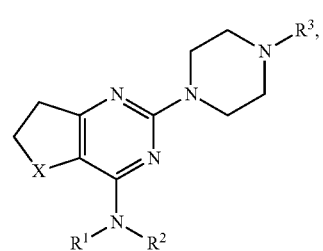

wherein
X denotes SO or $SO_2$,
$R^1$ denotes H, $C_{1-5}$-alkyl,
$R^2$ is H or a group selected from among $C_{1-40}$-alkyl and $C_{2-6}$-alkenyl, which may optionally be substituted by one or more groups selected from halogen and $C_{1-3}$-fluoroalkyl or which may optionally be substituted by one or more groups selected from among $OR^{2.1}$, $COOR^{2.1}$, $CONR^{2.2}R^{2.3}$, $SR^{2.1}$, SO—$R^{2.1}$, $SO_2$—$R^{2.1}$, $C_{6-10}$-aryl, a het, a hetaryl, a mono- or bicyclic $C_{3-10}$-cycloalkyl, $CH_2$—$NR^{2.2}R^{2.3}$ and $NR^{2.2}R^{2.3}$, which in turn may optionally be substituted by one or more groups selected from among OH, halogen, $OR^{2.1}$, oxo, $CF_3$, $CHF_2$, $CH_2F$, $C_{1-5}$-alkyl, $C_{1-6}$-alkanol, $C_{6-10}$-aryl, $COOR^{2.1}$, $CH_2$—$NR^{2.2}R^{2.3}$ and $NR^{2.2}R^{2.3}$,
wherein $R^{2.1}$ is H or a group selected from among $C_{1-6}$-alkyl, $C_{1-6}$-alkanol, $C_{1-3}$-haloalkyl, mono- or bicyclic $C_{3-10}$-cycloalkyl, $C_{6-10}$-aryl-$C_{1-6}$-alkylene, mono- or bicyclic hetaryl-$C_{1-6}$-alkylene, het-$C_{1-6}$-alkylene, $C_{3-10}$-cycloalkyl-$C_{1-6}$-alkylene, a mono- or bicyclic $C_{6-10}$-aryl,
a hetaryl and a het,
which may optionally be substituted by one or more groups selected from among OH, O—($C_{1-3}$-alkyl), halogen, $C_{1-6}$-alkyl and $C_{6-10}$-aryl,
wherein $R^{2.2}$ and $R^{2.3}$ independently of one another denote H or a group selected from among $C_{1-6}$-alkyl, mono- or bicyclic $C_{3-10}$ cycloalkyl, $C_{6-10}$-aryl-$C_{1-6}$-alkylene, hetaryl-$C_{1-6}$-alkylene, mono- or bicyclic $C_{6-10}$-aryl, het, hetaryl, CO—$NH_2$, CO—$NHCH_3$, CO—$N(CH_3)_2$, $SO_2$—($C_1$-$C_2$-alkyl), CO—$R^{2.1}$ and $COOR^{2.1}$,
which may optionally be substituted by one or more groups selected from among OH, halogen, $C_{1-6}$-alkyl, $C_{6-10}$-aryl and $COOR^{2.1}$,
wherein
het is a three- to eleven-membered, mono- or bicyclic, saturated or partly saturated, optionally annelated or optionally bridged heterocyclic group which contains 1, 2, 3 or 4 heteroatoms selected independently of one another from among N, S or O, and wherein hetaryl is a five- to eleven-membered, mono- or bicyclic, optionally annelated heteroaryl which contains 1, 2, 3 or 4 heteroatoms selected independently of one another from among N, S or O, and wherein cycloalkyl may be saturated or partly saturated, or $R^2$ denotes a mono- or polycyclic $C_{3-10}$ cycloalkyl, which may optionally be singly or multiply bridged by $C_{1-3}$-alkyl groups and which may optionally be substituted by a group selected from among branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, het, $C_{6-10}$-aryl, $C_{1-6}$-alkyl, $C_{6-10}$-aryl-$C_{1-46}$-alkylene, hetaryl-$C_{1-6}$-alkylene, mono- or bicyclic $C_{3-10}$ cycloalkyl and $NR^{2.2}R^{2.3}$, which may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, het, —$C_{1-6}$-alkyl, $C_{1-3}$-fluoroalkyl, $C_{6-10}$-aryl-$C_{1-6}$-alkylene, het-$C_{1-6}$-alkylene, hetaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which in turn may optionally be substituted by one or more groups selected from among OH, $OR^{2.1}$, $CF_3$, $CHF_2$, $CH_2F$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a group selected from among het and hetaryl, which may optionally be substituted by one or more groups selected from among halogen, OH, oxo, $CF_3$, $CHF_2$ and $CH_2F$ or by one or more groups selected from among $OR^{2.1}$, $C_{1-3}$-alkylene-$OR^{2.1}$, $SR^{2.1}$, $SO$—$R^{2.1}$ and $SO_2$—$R^{2.1}$, $COOR^{2.1}$, $COR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl, $C_{1-3}$-alkylene-$OR^{2.1}$ and $NR^{2.2}R^{2.3}$, which in turn may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or wherein $NR^1R^2$ together denotes a heterocyclic four- to seven-membered ring which may optionally be bridged, which contains 1, 2 or 3 heteroatoms selected from among N, O and S and which may optionally be substituted by one or more groups selected from among OH, $OR^{2.1}$, $C_{1-3}$-alkylene-$O^{R.1}$, oxo, halogen, $C_{1-6}$-alkyl, $C_{6-10}$-aryl, $COOR^{2.1}$, $CH_2$—$NR^{2.2}$—$COO$—$R^{2.1}$, $CH_2$—$NR^{2.2}$—$CO$—$R^{2.1}$, $CH_2$—$NR^{2.2}$—$CO$—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—$CO$—$NR^{2.2}R^{2.3}$ $CO$—$NR^{2.2}R^{2.3}$, $CH_2$—$NR^{2.2}R^{2.3}$ and $NR^{2.2}R^{2.3}$, and wherein $R^3$ is a group selected from among a het and a hetaryl, which may optionally be substituted by one or more groups selected from among halogen, $C_{1-3}$-fluoroalkyl, CN, OH, oxo, —$C_{1-6}$-alkyl, —$O$—$R^{2.1}$, —$COOR^{2.1}$, $SO$—$R^{2.1}$, $SO_2$—$R^{2.1}$, $C_{6-10}$-aryl, $C_{1-3}$-alkylene-$C_{6-10}$-aryl, —$C_{1-3}$-alkylene-$NR^{2.2}R^{2.3}$, —$NR^{2.2}R^{2.3}$, a $C_{3-10}$-cycloalkyl, a $C_{1-3}$-alkylene-$C_{3-10}$-cycloalkyl, a het, a hetaryl, $C_{1-3}$-alkylene-hetaryl, and $C_{1-3}$-alkylene-het, which in turn may optionally be substituted by one or more groups selected from among OH, halogen, —$C_{1-3}$-fluoroalkyl, $C_{1-6}$-alkyl, $C_{6-10}$-aryl, —$COO(C_{1-3}$-alkyl) and $O$—($C_{1-3}$-alkyl), contain at least one NSAID (=non-steroidal anti-inflammatory drug) (2).

Preferred are drug combinations which, in addition to one or more, preferably one, compound of general formula 1 as PDE4 inhibitor, wherein X denotes SO, $R^1$ denotes H $R^2$ is H or $C_{1-6}$-alkyl, which may optionally be substituted by one or more groups selected from F, $CF_3$, $CHF_2$ or $CH_2F$ or which may optionally be substituted by one or more groups selected from among $OR^{2.1}$, $COOR^{2.1}$, $CONR^{2.2}R^{2.3}$, $SR^{2.1}$, $SO$—$R^{2.1}$, $SO_2$—$R^{2.1}$, phenyl, a het, a hetaryl, a monocyclic $C_{3-7}$-cycloalkyl, $CH_2$—$NR^{2.2}R^{2.3}$ and $NR^{2.2}R^{2.3}$, which in turn may optionally be substituted by one or more groups selected from among OH, F, Cl, Br, $CF_3$, $CHF_2$, $CH_2F$, $OR^{2.1}$, oxo, methyl, ethyl, propyl, isopropyl, $C_{1-2}$-alkanol, phenyl, $COOR^{2.1}$, $CH_2$—$NR^{2.2}R^{2.3}$ and $NR^{2.2}R^{2.3}$, wherein $R^{2.1}$ is H or a group selected from among methyl, ethyl, propyl, isopropyl, monocyclic $C_{3-7}$cycloalkyl, phenyl-$C_{1-2}$-alkylene, hetaryl-$C_{1-2}$-alkylene, het-$C_{1-2}$-alkylene, $C_{3-7}$-cycloalkyl-$C_{1-2}$-alkylene, phenyl, a hetaryl and a het, which may optionally be substituted by one or more groups selected from among OH, halogen, methyl, ethyl, propyl, isopropyl, O-methyl, O-ethyl, O-propyl, O-isopropyl and phenyl, wherein $R^{2.2}$ and $R^{2.3}$ independently of one another denote H or a group selected from among methyl, ethyl, propyl, isopropyl, monocyclic $C_{3-7}$cycloalkyl, phenyl-$C_{1-3}$-alkylene, hetaryl-$C_{1-3}$-alkylene, phenyl, het, hetaryl, $CO$—$NH_2$, $CO$—$NHCH_3$, $CON(CH_3)_2$, $SO_2$—$(C_1$-$C_2$-alkyl), $CO$—$R^{2.1}$ and $COOR^{2.1}$, which may optionally be substituted by one or more groups selected from among OH, F, Cl, Br, methyl, ethyl, propyl, isopropyl, phenyl and $COOR^{2.1}$, wherein het is a three- to seven-membered, monocyclic, saturated or partly saturated heterocyclic group which contains 1, 2 or 3 heteroatoms independently selected from among N, S or O, and wherein hetaryl is a five- to six-membered, monocyclic, aromatic heteroaryl which contains 1, 2 or 3 heteroatoms independently selected from among N, S or O, and wherein cycloalkyl may be saturated or partly saturated, or $R^2$ denotes a monocyclic $C_{3-7}$cycloalkyl, which may optionally be substituted by a group selected from among branched or unbranched $C_{1-2}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, het, methyl, ethyl, propyl, isopropyl, phenyl, phenyl-$C_{1-2}$-alkylene, hetaryl-$C_{1-2}$-alkylene, monocyclic $C_{3-7}$cycloalkyl and $NR^{2.2}R^{2.3}$, which may optionally be substituted by one or more groups selected from among OH, $OR^{2.1}$, oxo, halogen, $CF_3$, $CHF_2$, $CH_2F$, methyl, ethyl, propyl, isopropyl, phenyl and $NR^{2.2}R^{2.3}$, or $R^2$ denotes a phenyl, which may optionally be substituted by OH, SH, F, Cl or Br or by one or more groups selected from among $OR^{2.1}$, $COOR^{2.1}$, $NR^{2.2}R^{2.3}$, $CH_2$—$NR^{2.2}R^{2.3}$, $C_{3-7}$-cycloalkyl, het, methyl, ethyl, propyl, isopropyl, $CF_3$, $CHF_2$, $CH_2F$, phenyl-$C_{1-2}$-alkylene, het-$C_{1-2}$-alkylene, hetaryl-$C_{1-2}$-alkylene, phenyl, $SO_2$—$CH_3$, $SO_2$—$CH_2CH_3$ and $SO_2$—$NR^{2.2}R^{2.3}$, which in turn may optionally be substituted by one or more groups selected from among OH, $OR^{2.1}$, oxo, F, Cl, Br, $CF_3$, $CHF_2$, $CH_2F$, methyl, ethyl, propyl, isopropyl, phenyl and $NR^{2.2}R^{2.3}$, or $R^2$ denotes a group selected from among a het and a hetaryl, which may optionally be substituted by one or more groups selected from among F, Cl, Br, OH, oxo, $CF_3$, $CHF_2$, $CH_2F$ and SH or by one or more groups selected from among $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-2}$-alkanol, $C_{3-10}$-cycloalkyl, phenyl, methyl, ethyl, propyl, isopropyl, phenyl-$C_{1-2}$-alkylene, hetaryl-$C_{1-2}$-alkylene, het, hetaryl, $C_{1-2}$-alkanol and $NR^{2.2}R^{2.3}$, which in turn may optionally be substituted by one or more groups selected from among OH, $OR^{2.1}$, oxo, F, Cl, Br, $CF_3$, $CHF_2$, $CH_2F$, $C_{1-6}$-alkyl, phenyl and $NR^{2.2}R^{2.3}$, and wherein $R^3$ is a group selected from among a saturated or partly saturated, monocyclic three- to seven-membered heterocyclic group, a saturated or partly saturated, bicyclic five- to eleven-membered heterocyclic group, a monocyclic, five- to six-membered heteroaryl and a bicyclic, seven- to eleven-membered heteroaryl, which contains in each case 1, 2, 3 or 4 heteroatoms selected independently of one another from among N, O and S and which may optionally be substituted in each case by one or more groups selected from among halogen, $C_{1-3}$-fluoroalkyl, CN, OH, oxo, —$C_{1-6}$-alkyl, —O—$R^{2.1}$, —$COOR^{2.1}$, SO—$R^{2.1}$, $SO_2$—$R^{2.1}$, $C_{6-10}$-aryl, $C_{1-3}$-alkylene-$C_{6-10}$-aryl, —$C_{1-3}$-alkylene-$NR^{2.2}R^{2.3}$, —$NR^{2.2}R^{2.3}$, a $C_{3-10}$-cycloalkyl, a $C_{1-3}$-alkylene-$C_{3-10}$-cycloalkyl, het, a hetaryl, $C_{1-3}$-alkylene-hetaryl and $C_{1-3}$-alkylene-het, which in turn may optionally be substituted by one or more groups selected from among OH, halogen, —$C_{1-3}$-fluoroalkyl, $C_{1-6}$-alkyl, $C_{6-10}$-aryl, —COO($C_{1-3}$-alkyl) and O—($C_{1-3}$-alkyl), contain at least one NSAID (2).

Also preferred are drug combinations which, in addition to one or more, preferably one, compound of general formula 1 as PDE4 inhibitor, wherein $R^2$ is a group according to formula 3

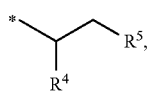

wherein $R^5$ is OH or $NH_2$ and
wherein $R^4$ denotes a group selected from among $C_{1-4}$-alkyl, hetaryl and phenyl, which may optionally be substituted by one or more groups selected from among OH, F, Br, $OR^{2.1}$, oxo, methyl, ethyl, $C_{1-2}$-alkanol, phenyl, $COOR^{2.1}$, $CH_2$—$NR^{2.2}R^{2.3}$
and $NR^{2.2}R^{2.3}$,
and wherein the remaining groups are as hereinbefore defined,
contain at least one NSAID (2).

Also preferred are drug combinations which, in addition to one or more, preferably one, compound of general formula 1 as PDE4 inhibitor, wherein $R^2$ is a group according to formula 3

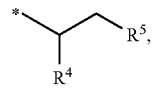

wherein $R^5$ is OH or $NH_2$ and
wherein $R^4$ denotes methyl, ethyl, propyl, isopropyl
and wherein the remaining groups are as hereinbefore defined,
contain at least one NSAID (2).

Also preferred are drug combinations which, in addition to one or more, preferably one, compound of general formula 1 as PDE4 inhibitor, wherein $R^2$ is a monocyclic three-, four-, five-, six- or seven-membered cycloalkyl ring which may optionally be substituted in the spiro position by a group selected from among —$CH_2$—$OR^{2.1}$, branched or unbranched $C_{2-6}$-alkylene-$OR^{2.1}$, methyl, ethyl, propyl, isopropyl, butyl, isobutyl, cyclopropyl, —$CF_3$, $CHF_2$, $CH_2F$ and $C_{2-4}$-fluoroalkyl, wherein $R^{2.1}$ is selected from among methyl, ethyl, propyl, isopropyl, butyl, isobutyl, and wherein the remaining groups are as hereinbefore defined, contain at least one NSAID (2).

Also preferred are drug combinations which, in addition to one or more, preferably one, compound of general formula 1 as PDE4 inhibitor, wherein $R^2$ is a phenyl which is optionally substituted in one or both meta positions by one or more groups selected from among methyl, ethyl, propyl, isopropyl, cyclopropyl, F, Cl, Br, OH, $OR^{2.1}$, $COOR^{2.1}$, $CF_3$, $CHF_2$, $CH_2F$, $NH_2$ and $N(CH_3)_2$, wherein $R^{2.1}$ may be H, methyl or ethyl,
and wherein the remaining groups are as hereinbefore defined,
contain at least one NSAID (2).

Also preferred are drug combinations which, in addition to one or more, preferably one, compound of general formula 1 as PDE4 inhibitor, wherein $R^2$ is a monocyclic, saturated three-, four-, five-, six- or seven-membered heterocyclic group with 1, 2 or 3 heteroatoms in each case selected from among N, O and S, which may optionally be substituted by one or more groups selected from among fluorine, chlorine, bromine, $CF_3$, $CHF_2$, $CH_2F$, OH, oxo and SH or by one or more groups selected from among $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl and $NR^{2.2}R^{2.3}$, which in turn may optionally be substituted by one or more groups selected from among OH, $OR^{2.1}$, oxo, F, Cl, $CF_3$, $CHF_2$, $CH_2F$, $C_{1-6}$-alkyl, phenyl and $NR^{2.2}R^{2.3}$,
wherein $R^{2.1}$, $R^{2.2}$ and $R^{2.3}$ and the remaining groups are as hereinbefore defined, contain at least one NSAID (2).

Also preferred are drug combinations which, in addition to one or more, preferably one, compound of general formula 1 as PDE4 inhibitor, wherein $R^2$ is a monocyclic, saturated, six-membered heterocyclic group with a heteroatom selected from among N, O and S, which may optionally be substituted by one or more groups selected from among F, Cl, Br, $CF_3$, $CHF_2$, $CH_2F$, OH, oxo, $NH_2$, $NHCH_3$, $N(CH_3)_2$, methyl, ethyl, propyl, isopropyl, cyclopropyl, methoxy and ethoxy,
and wherein the remaining groups are as hereinbefore defined,
contain at least one NSAID (2).

Also preferred are drug combinations which, in addition to one or more, preferably one, compound of general formula 1 as PDE4 inhibitor, wherein $R^2$ denotes a group selected from among piperidine or tetrahydropyran, which may optionally be substituted by one or more groups selected from among F, Cl, Br, OH, $CF_3$, $CHF_2$, $CH_2F$, $NH_2$, $NHCH_3$, $N(CH_3)_2$, oxo, methyl and methoxy, and wherein the remaining groups are as hereinbefore defined, contain at least one NSAID (2).

Also preferred are drug combinations which, in addition to one or more, preferably one, compound of general formula 1 as PDE4 inhibitor, wherein $R^3$ is a monocyclic five- or six-membered heteroaryl ring which may optionally be substituted by one or more groups selected from among F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—$(CH_3)$, SO—$(CH_3)$, $SO_2$—$(CH_2CH_3)$, SO—$(CH_2CH_3)$, phenyl, -methylene-phenyl, -ethylene-phenyl, —$NH_2$, —$NH(CH_3)$, $N(CH_3)_2$, -methylene-$NH_2$, -methylene-$NH(CH_3)$, -methylene-N$(CH_3)_2$, a $C_{3-6}$-cycloalkyl, a methylene-$C_{3-6}$-cycloalkyl, a saturated or partly saturated, five- to six-membered heterocyclic group, a five- or six-membered heteroaryl, -methylene-hetaryl, and -methylene-het, which in turn may optionally be substituted by one or more groups selected from among OH, F, Cl, Br, $CF_3$, $CHF_2$, $CH_2F$, methyl, ethyl, propyl, isopropyl, phenyl, —COO$(CH_3)$, —O-methyl and —O-ethyl, and wherein the remaining groups are as hereinbefore defined, contain at least one NSAID (2).

Also preferred are drug combinations which, in addition to one or more, preferably one, compound of general formula 1 as PDE4 inhibitor, wherein $R^3$ is a bicyclic 9- to 11-membered saturated, unsaturated or partly saturated heterocyclic group which may optionally be substituted by one or more groups selected from among F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—$(CH_3)$, SO—$(CH_3)$, $SO_2$—$(CH_2CH_3)$, SO—$(CH_2CH_3)$, phenyl, -methylene-phenyl, -ethylene-phenyl, —$NH_2$, —$NH(CH_3)$, $N(CH_3)_2$, -methylene-$NH_2$, -methylene-$NH(CH_3)$, -methylene-N$(CH_3)_2$, a —$C_{3-6}$-cycloalkyl, α-methylene-$C_{3-6}$-cycloalkyl, a saturated, partly unsaturated or unsaturated 5- to 6-membered heterocyclic group, a 5- to 6-membered heteroaryl, -methylene-hetaryl, and -methylene-het, which in turn may optionally be substituted by one or more groups selected from among OH, F, Cl, Br, $CF_3$, $CHF_2$, $CH_2F$, methyl, ethyl, propyl, isopropyl, phenyl, —COO$(CH_3)$, —O-methyl and —O-ethyl, and wherein the remaining groups are as hereinbefore defined, contain at least one NSAID (2).

Also preferred are drug combinations which, in addition to one or more, preferably one, compound of general formula 1 as PDE4 inhibitor, wherein $R^3$ is a monocyclic five- or six-membered heteroaryl ring selected from among pyrrole, pyrazole, furan, thiophene, thiazole, imidazole, oxazole, pyridazine, pyrimidine, pyrazine, thiadiazole, oxadiazole, triazine, isoxazole, isothiazole and pyridine, which may optionally be substituted by one or more groups selected from among F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—$(CH_3)$, $SO_2$—$(CH_2CH_3)$, phenyl, -methylene-phenyl, -ethylene-phenyl, —$NH_2$, —$NH(CH_3)$, $N(CH_3)_2$, -methylene-$NH_2$, -methylene-$NH(CH_3)$, -methylene-N$(CH_3)_2$, a $C_{3-6}$-cycloalkyl, a methylene-$C_{3-6}$-cycloalkyl, a het, a hetaryl, -methylene-hetaryl, and -methylene-het, which in turn may optionally be substituted by one or more groups selected from among OH, F, Cl, Br, $CF_3$, $CHF_2$, $CH_2F$, methyl, ethyl, propyl, isopropyl, phenyl, —COO$(CH_3)$, —O-methyl and —O-ethyl, and wherein the remaining groups are as hereinbefore defined, contain at least one NSAID (2).

Also preferred are drug combinations which, in addition to one or more, preferably one, compound of general formula 1 as PDE4 inhibitor, wherein $R^3$ denotes a bicyclic 9- to 11-membered heterocyclic group selected from among benzoxazole, benzodioxole, dihydrobenzodioxin, benzodioxin, benzisoxazole, benzothiazole, benzisothiazole, thienopyrimidine, furopyrimidine, thienopyridine, furopyridine, indole, isoindole, quinoxaline, naphthyridine, pyridopyrazine, pyridopyrimidine, quinoline, isoquinoline, benzoimidazole, 6,7,8,9-tetrahydro-5H-pyrazino[2,3-d]azepine, benzothiophene, benzofuran, quinazoline, indazole, isobenzofuran and pteridine, which may optionally be substituted by one or more groups selected from among F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—$(CH_3)$, $SO_2$—$(CH_2CH_3)$, phenyl, -methylene-phenyl, -ethylene-phenyl, —$NH_2$, —$NH(CH_3)$, $N(CH_3)_2$, -methylene-$NH_2$, -methylene-$NH(CH_3)$, -methylene-N$(CH_3)_2$, a $C_{3-6}$-cycloalkyl, a methylene-$C_{3-6}$-cycloalkyl, a het, a hetaryl, -methylene-hetaryl, and -methylene-het, which in turn may optionally be substituted by one or more groups selected from among OH, F, Cl, Br, $CF_3$, $CHF_2$, $CH_2F$, methyl, ethyl, propyl, isopropyl, phenyl, —COO$(CH_3)$, —O-methyl and —O-ethyl, and wherein the remaining groups are as hereinbefore defined, contain at least one NSAID (2).

Also preferred are drug combinations which, in addition to one or more, preferably one, compound of general formula 1 as PDE4 inhibitor, wherein $R^1$ is H, $R^2$ is a group selected from among

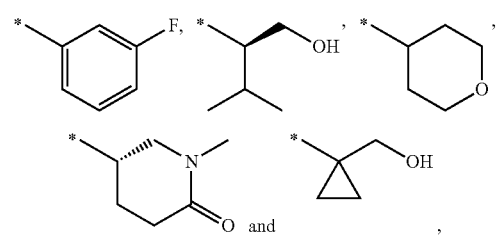

R³ is a group selected from among

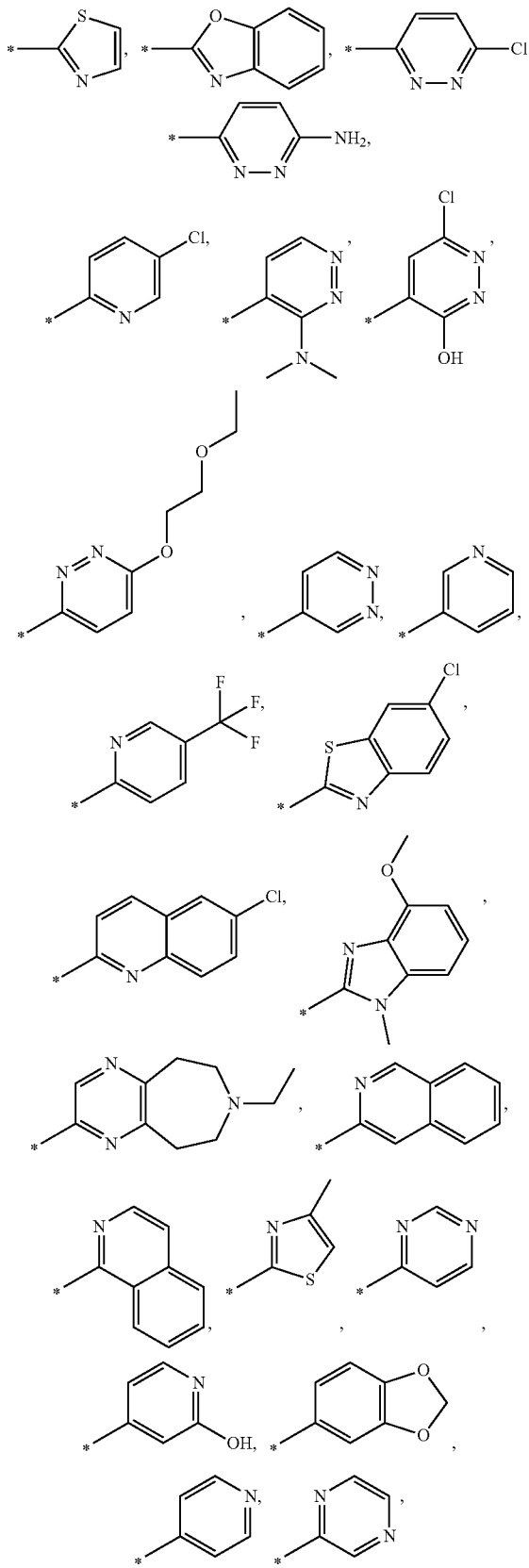
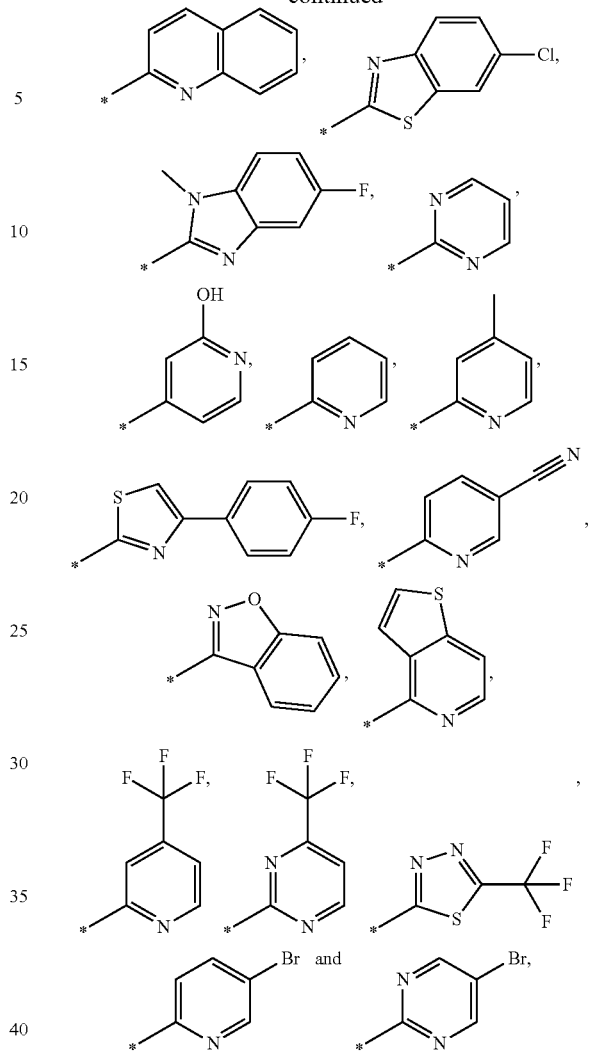

contain at least one NSAID (2).

Also preferred are drug combinations which, in addition to one or more, preferably one, compound of general formula 1 as PDE4 inhibitor selected from among:

1.1 (3-fluorophenyl)-[5-oxo-2-(4-thiazol-2-yl-piperazin-1-yl)-6,7-dihydro-5H-5λ⁴-thieno[3,2-d]pyrimidin-4-yl]-amine 1.2 (R)-3-methyl-2-[5-oxo-2-(4-thiazol-2-yl-piperazin-1-yl)-6,7-dihydro-5H-5λ⁴-thieno[3,2-d]pyrimidin-4-ylamino]-butan-1-ol 1.3 [2-(4-benzoxazol-2-yl-piperazin-1-yl)-5-oxo-6,7-dihydro-5H-5λ⁴-thieno[3,2-d]pyrimidin-4-yl]-(3-fluorophenyl)-amine 1.4 [2-(4-benzoxazol-2-yl-piperazin-1-yl)-5-oxo-6,7-dihydro-5H-5λ⁴-thieno[3,2-d]pyrimidin-4-yl]-(tetrahydropyran-4-yl)-amine 1.5 (R)-2-{2-[4-(6-chloropyridazin-3-yl)-piperazin-1-yl]-5-oxo-6,7-dihydro-5H-5λ⁴-thieno[3,2-d]pyrimidin-4-ylamino}-3-methylbutan-1-ol 1.6 {2-[4-(6-chloropyridazin-3-yl)-piperazin-1-yl]-5-oxo-6,7-dihydro-5H-5λ⁴-thieno[3,2-d]pyrimidin-4-yl}-(3-fluorophenyl)-amine 1.7 (R)-2-[2-(4-benzoxazol-2-yl-piperazin-1-yl)-5-oxo-6,7-dihydro-5H-5λ⁴-thieno[3,2-d]pyrimidin-4-ylamino]-3-methylbutan-1-ol 1.8 (1-{2-[4-(5-chloropyridin-2-yl)-piperazin-1-yl]-5-oxo-6,7-dihydro-5H-5λ⁴-thieno[3,2-d]pyrimidin-4-ylamino}-cyclopropyl)-methanol 1.9 {2-[4-(5-chloropyridin-2-yl)-piperazin-1-yl]-5-oxo-6,7-dihydro-5H-5λ⁴-thieno[3,2-d]pyrimidin-4-yl}-(tetrahydropyran-4-yl)-amine 1.10 {2-[4-(3-dimethylaminopyridazin-4-yl)-piperazin-1-yl]-5-oxo-6,7-dihydro-5H-5λ⁴-thieno[3,2-d]pyrimidin-4-yl}-(3-fluorophenyl)-amine 1.11 6-chloro-4-{4-[4-(3-fluorophenylamino)-5-oxo-6,7-dihydro-5H-5λ⁴-thieno[3,2-d]pyrimidin-2-yl]-piperazin-1-yl}-pyridazin-3-ol 1.12 2-{4-[6-(2-ethoxyethoxy)-pyridazin-3-yl]-piperazin-1-yl}-5-oxo-6,7-dihydro-5H-5λ⁴-thieno[3,2-d]pyrimidin-4-yl)-(3-fluorophenyl)-amine 1.13 (3-fluorophenyl)-[5-oxo-2-(4-pyridazin-4-yl-piperazin-1-yl)-6,7-dihydro-5H-5λ⁴-thieno[3,2-d]pyrimidin-4-yl]-amine 1.14 (R)-2-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-ylamino}-3-methylbutan-1-ol 1.15 (R)-2-{2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-ylamino}-3-methylbutan-1-ol 1.16 (R)-3-methyl-2-[5-oxo-2-(4-pyrimidin-4-yl-piperazin-1-yl)-6,7-dihydro-5H-5λ⁴-thieno[3,2-d]pyrimidin-4-ylamino]-butan-1-ol 1.17 4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridin-2-ol 1.18 (R)-3-methyl-2-[5-oxo-2-(4-pyridin-4-yl-piperazin-1-yl)-6,7-dihydro-5H-5λ⁴-thieno[3,2-d]pyrimidin-4-ylamino]-butan-1-ol 1.19 (R)-2-{2-[4-(3-dimethylaminopyridazin-4-yl)-piperazin-1-yl]-5-oxo-6,7-dihydro-5H-5λ⁴-thieno[3,2-d]pyrimidin-4-ylamino}-3-methylbutan-1-ol 1.20 6-chloro-4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridazin-3-ol 1.21 (R)-2-(2-{4-[6-(2-ethoxyethoxy)-pyridazin-3-yl]-piperazin-1-yl}-5-oxo-6,7-dihydro-5H-5λ⁴-thieno[3,2-d]pyrimidin-4-ylamino)-3-methyl butan-1-ol 1.22 (R)-3-methyl-2-[5-oxo-2-(4-pyridazin-4-yl-piperazin-1-yl)-6,7-dihydro-5H-5λ⁴-thieno[3,2-d]pyrimidin-4-ylamino]-butan-1-ol 1.23 {1-[5-oxo-2-(4-pyrimidin-4-yl-piperazin-1-yl)-6,7-dihydro-5H-5λ⁴-thieno[3,2-d]pyrimidin-4-ylamino]-cyclopropyl}-methanol 1.24 {1-[5-oxo-2-(4-pyrimidin-4-yl-piperazin-1-yl)-6,7-dihydro-5H-5λ⁴-thieno[3,2-d]pyrimidin-4-ylamino]-cyclopropyl}-methanol 1.25 (S)-1-methyl-5-[5-oxo-2-(4-pyrimidin-4-yl-piperazin-1-yl)-6,7-dihydro-5H-5λ⁴-thieno[3,2-d]pyrimidin-4-ylamino]-piperidin-2-one 1.26 {2-[4-(5-fluoro-1-methyl-1H-benzimidazol-2-yl)-piperazin-1-yl]-5-oxo-6,7-dihydro-5H-5λ⁴-thieno[3,2-d]pyrimidin-4-yl}-(tetrahydropyran-4-yl)-amine 1.27 [5-oxo-2-(4-pyridin-4-yl-piperazin-1-yl)-6,7-dihydro-5H-5λ⁴-thieno[3,2-d]pyrimidin-4-y]-4(tetrahydropyran-4-yl)-amine 4

1.28 (3-fluorophenyl)-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-y}-amine 1.29 {2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-y}-(3-fluorophenyl)-amine 1.30 (3-fluorophenyl)-[5-oxo-2-(4-pyrimidin-4-yl-piperazin-1-yl)-6,7-dihydro-5H-5λ⁴-thieno[3,2-d]pyrimidin-4-yl]-amine 1.31 4-{4-[4-(3-fluorophenylamino)-5-oxo-6,7-dihydro-5H-5λ⁴-thieno[3,2-d]pyrimidin-2-yl]-piperazin-1-yl}-pyridin-2-ol 1.32 (3-fluorophenyl)-[5-oxo-2-(4-pyridin-4-yl-piperazin-1-yl)-6,7-dihydro-5H-5λ4-thieno[3,2-d]pyrimidin-4-yl]-amine 1.33 (3-fluorophenyl)-(2-{4-[4-(4-fluorophenyl)-thiazol-2-yl]-piperazin-1-yl}-5-oxo-6,7-dihydro-5H-5λ4-thieno[3,2-d]pyrimidin-4-yl)-amine 1.34 [2-(4-benzo[d]isoxazol-3-yl-piperazin-1-yl)-5-oxo-6,7-dihydro-5H-5λ4-thieno[3,2-d]pyrimidin-4-yl]-(3-fluorophenyl)-amine 1.35 (R)-2-(2-{4-[4-(4-fluorophenyl)-thiazol-2-yl]-piperazin-1-yl}-5-oxo-6,7-dihydro-5H-5λ4-thieno[3,2-d]pyrimidin-4-ylamino)-3-methylbutan-1-ol 1.36 (R)-2-[2-(4-benzo[d]isoxazol-3-yl-piperazin-1-yl)-5-oxo-6,7-dihydro-5H-5λ4-thieno[3,2-d]pyrimidin-4-ylamino]-3-methylbutan-1-ol contain at least one NSAID (2).

The above mentioned compounds of formula 1 are prepared as described in detail in the synthesis instructions.

Also preferred are the above drug combinations which contain at least one NSAID (2) selected from COX 1-inhibitors or COX 2-inhibitors, in addition to one or more, preferably one, compound of general formula 1 as PDE4 inhibitor.

Also preferred are the above mentioned drug combinations which contain, in addition to one or more, preferably one compound of general formula 1 as PDE4 inhibitor, at least one NSAID (2) selected from among
aceclofenac (2.1), acemetacin (2.2), acetylsalicylic acid (2.3), alclofenac (2.4), alminoprofen (2.5), amfenac (2.6), ampiroxicam (2.7), antolmetinguacil (2.8), anirolac (2.9), antrafenine (2.10), azapropazone (2.11), benorilate (2.12), bermoprofen (2.13), bindarit (2.14), bromfenac (2.15), bucloxinic acid (2.16), bucolom (2.17), bufexamac (2.18), bumadizone (2.19), butibufen (2.20), butixirate (2.21), carbasalate calcium (2.22), carprofen (2.23), choline magnesium trisalicylate (2.24), celecoxib (2.25), cinmetacin (2.26), cinnoxicam (2.27), clidanac (2.28), clobuzarit (2.29), deboxamet (2.30), dexibuprofen (2.31), dexketoprofen (2.32), diclofenac (2.33), diflunisal (2.34), droxicam (2.35), eltenac (2.36), enfenamic acid (2.37), etersalate (2.38), etodolac (2.39), etofenamat (2.40), etoricoxib (2.41), feclobuzon (2.42), felbinac (2.43), fenbufen (2.44), fenclofenac (2.45), fenoprofen (2.46), fentiazac (2.47), fepradinol (2.48), feprazone (2.49), flobufen (2.50), floctafenin (2.51), flufenamic acid (2.52), flufenisal (2.53), flunoxaprofen (2.54), flurbiprofen (2.55), flurbiprofenaxetil (2.56), furofenac (2.57), furprofen (2.58), glucametacin (2.59), ibufenac (2.60), ibuprofen (2.61), indobufen (2.62), indometacin (2.63), indometacinfarnesil (2.64), indoprofen (2.65), isoxepac (2.66), isoxicam (2.67), ketoprofen (2.68), ketorolac (2.69), lobenzarit (2.70), lonazolac (2.71), lornoxicam (2.72), loxoprofen (2.73), lumiracoxib (2.74), meclofenamic acid (2.75), meclofen, mefenamic acid (2.76), meloxicam (2.77), mesalazin (2.78), miroprofen (2.79), mofezolac (2.80), nabumetone (2.81), naproxen (2.82), nifluminic acid (2.83), olsalazine (2.84), oxaprozin (2.85), oxipinac (2.86), oxyphenbutazone (2.87), parecoxib (2.88), phenylbutazone (2.89), pelubiprofen (2.90), pimeprofen (2.91), pirazolac (2.92), piroxicam (2.93), pirprofen (2.94), pranoprofen (2.95), prifelon (2.96), prinomod (2.97), proglumetacin (2.98), proquazone (2.99), protizinic acid (2.100), rofecoxib (2.101), romazarit (2.102), salicylamide (2.103), salicylic acid (2.104), salmistein (2.105), salnacedin (2.106), salsalate (2.107), sulindac (2.108), sudoxicam (2.109), suprofen (2.110), talniflumat (2.111), tenidap (2.112), tenosal (2.113), tenoxicam (2.114), tepoxalin (2.115), tiaprofenic acid (2.116), taramide (2.117), tilnoprofenarbamel (2.118), timegadine (2.119), tinoridine (2.120), tiopinac (2.121), tolfenamic acid (2.122), tolmetin (2.123), ufenamate (2.124), valdecoxib (2.125), ximoprofen (2.126), zaltoprofen (2.127) and zoliprofen (2.128).

Also preferred are the above drug combinations which contain, in addition to one or more, preferably one PDE4 inhibitor of general formula 1, as NSAID (2) at least one COX 2 inhibitor selected from among celecoxib (2.25), etoricoxib (2.41), lumiracoxib (2.74), parecoxib (2.88), rofecoxib (2.101) and valdecoxib (2.125).

Particularly preferred are the above-mentioned drug combinations which contain, in addition to one or more, preferably one PDE4 inhibitor of general formula 1 at least one NSAID (2) selected from among acetylsalicylic acid (2.3), celecoxib (2.25), diclofenac (2.33), ibuprofen (2.61), indometacin (2.63), lumiracoxib (2.74), meloxicam (2.77), naproxen (2.82) and priroxicam (2.93).

The present invention relates in particular to the above-mentioned drug combinations which contain, in addition to one or more, preferably one PDE4 inhibitor of general formula 1, at least one NSAID (2) selected from among acetylsalicylic acid (2.3), diclofenac (2.33), meloxicam (2.77), naproxen (2.82) and ibuprofen (2.61).

Particularly preferred within the scope of the present invention are those of the above drug combinations which are selected from among
1.1 and 2.3; 1.1 and 2.33; 1.1 and 2.77; 1.1 and 2.82; 1.1 and 2.61; 1.2 and 2.3; 1.2 and 2.33; 1.2 and 2.77; 1.2 and 2.82; 1.2 and 2.61; 1.3 and 2.3; 1.3 and 2.33; 1.3 and 2.77; 1.3 and 2.82; 1.3 and 2.61; 1.4 and 2.3; 1.4 and 2.33; 1.4 and 2.77; 1.4 and 2.82; 1.4 and 2.61; 1.5 and 2.3; 1.5 and 2.33; 1.5 and 2.77; 1.5 and 2.82; 1.5 and 2.61; 1.6 and 2.3; 1.6 and 2.33; 1.6 and 2.77; 1.6 and 2.82; 1.6 and 2.61; 1.7 and 2.3; 1.7 and 2.33; 1.7 and 2.77; 1.7 and 2.82; 1.7 and 2.61; 1.8 and 2.3; 1.8 and 2.33; 1.8 and 2.77; 1.8 and 2.82; 1.8 and 2.61; 1.9 and 2.3; 1.9 and 2.33; 1.9 and 2.77; 1.9 and 2.82; 1.9 and 2.61; 1.10 and 2.3; 1.10 and 2.33; 1.10 and 2.77; 1.10 and 2.82; 1.10 and 2.61; 1.11 and 2.3; 1.11 and 2.33; 1.11 and 2.77; 1.11 and 2.82; 1.11 and 2.61; 1.12 and 2.3; 1.12 and 2.33; 1.12 and 2.77; 1.12 and 2.82; 1.12 and 2.61; 1.13 and 2.3; 1.13 and 2.33; 1.13 and 2.77; 1.13 and 2.82; 1.13 and 2.61; 1.14 and 2.3; 1.14 and 2.33; 1.14 and 2.77; 1.14 and 2.82; 1.14 and 2.61; 1.15 and 2.3; 1.15 and 2.33; 1.15 and 2.77; 1.15 and 2.82; 1.15 and 2.61; 1.16 and 2.3; 1.16 and 2.33; 1.16 and 2.77; 1.16 and 2.82; 1.16 and 2.61; 1.17 and 2.3; 1.17 and 2.33; 1.17 and 2.77; 1.17 and 2.82; 1.17 and 2.61; 1.18 and 2.3; 1.18 and 2.33; 1.18 and 2.77; 1.18 and 2.82; 1.18 and 2.61; 1.19 and 2.3; 1.19 and 2.33; 1.19 and 2.77; 1.19 and 2.82; 1.19 and 2.61; 1.20 and 2.3; 1.20 and 2.33; 1.20 and 2.77; 1.20 and 2.82; 1.20 and 2.61; 1.21 and 2.3; 1.21 and 2.33; 1.21 and 2.77; 1.21 and 2.82; 1.21 and 2.61; 1.22 and 2.3; 1.22 and 2.33; 1.22 and 2.77; 1.22 and 2.82; 1.22 and 2.61; 1.23 and 2.3; 1.23 and 2.33; 1.23 and 2.77; 1.23 and 2.82; 1.23 and 2.61; 1.24 and 2.3; 1.24 and 2.33; 1.24 and 2.77; 1.24 and 2.82; 1.24 and 2.61; 1.25 and 2.3; 1.25 and 2.33; 1.25 and 2.77; 1.25 and 2.82; 1.25 and 2.61; 1.26 and 2.3; 1.26 and 2.33; 1.26 and 2.77; 1.2 and 2.82; 1.26 and; and 2.61; 1.27 and 2.3; 1.27 and 2.33; 1.27 and 2.77; 1.27 and 2.82; 1.27 and 2.61; 1.28 and 2.3; 1.28 and 2.33; 1.28 and 2.77; 1.28 and 2.82; 1.28 and 2.61; 1.29 and 2.3; 1.29 and 2.33; 1.29 and 2.77; 1.29 and 2.82; 1.29 and 2.61; 1.30 and 2.3; 1.30 and 2.33; 1.30 and 2.77; 1.30 and 2.82; 1.30 and 2.61; 1.31 and 2.3; 1.31 and 2.33; 1.31 and 2.77; 1.31 and 2.82; 1.31 and 2.61; 1.32 and 2.3; 1.32 and 2.33; 1.32 and 2.77; 1.32 and 2.82; 1.32 and 2.61; 1.33 and 2.3; 1.33 and 2.33; 1.33 and 2.77; 1.33 and 2.82; 1.33 and 2.61; 1.34 and 2.3; 1.34 and 2.33; 1.34 and 2.77; 1.34 and 2.82; 1.34 and 2.61; 1.35 and 2.3; 1.35 and 2.33; 1.35 and 2.77; 1.35 and 2.82; 1.35 and 2.61; 1.36 and 2.3; 1.36 and 2.33; 1.36 and 2.77; 1.36 and 2.82; 1.36 and 2.61.

Particularly preferred are the above-mentioned drug combinations wherein the PDE4 inhibitor of general formula 1 is administered in a single dose of 0.01 mg to 50 mg, preferably 0.05 to 30 mg, more preferably 0.1 to 20 mg, particularly 0.5 to 10 mg.

Also particularly preferred are the above mentioned drug combinations, wherein the NSAID (2) used is either
acetylsalicylic acid (2.3) in a single dose of 50 to 2000 mg, preferably 100 to 500 mg,
diclofenac (2.33) in a single dose of 25 mg to 150 mg, preferably 25 to 100 mg,
meloxicam (2.77) in a single dose of 7.5 mg to 30 mg, preferably 10 to 20 mg,
naproxen in a single dose of 250 to 1000 mg, preferably 250 to 750 mg, or
ibuprofen in a single dose of 200 to 2400 mg, preferably 200 to 800 mg, this single dose in each case being given once or twice a day.

In particular the invention relates to the above mentioned drug combinations, wherein the or at least one or more of the PDE4 inhibitor-mediated side effects is considerably reduced or avoided completely by comparison with the sole administration of the PDE4 inhibitor used in the drug combination. These PDE4 inhibitor-mediated side effects are preferably selected from among weight loss, leukocytosis, neutrophilia, nausea, vomiting, diarrhoea (including the occurrence of inflammatory parameters and the proliferation of fibroblasts in the mesentery). These PDE4 inhibitor-mediated side effects are more preferably selected from weight loss, leukocytosis, neutrophilia and diarrhoea. These PDE4 inhibitor-mediated side effects relate particularly to the occurrence of diarrhoea.

The present invention further relates to the use of an NSAID (2) for reducing the side effects of one or more PDE4-inhibitors in the treatment of a disease selected from among respiratory complaints, pulmonary diseases, gastrointestinal ailments and diseases and also inflammatory diseases of the joints, skin or eyes, cancers and diseases of the peripheral or central nervous system.

In another aspect the present invention relates to the use of a combination containing one or more PDE4-inhibitors and at least one NSAID (2) for the treatment of a disease selected from among respiratory complaints, pulmonary diseases, gastrointestinal ailments and diseases and also inflammatory diseases of the joints, skin or eyes, cancers and diseases of the peripheral or central nervous system.

It is also preferable to use a combination of one or more, preferably one, PDE4 inhibitor of general formula 1,

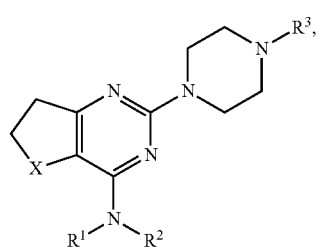

wherein X, $R^1$, $R^2$, and $R^3$ are defined as hereinbefore and according to the preferred definitions, and at least one NSAID for preparing a drug combination for the treatment of one of the diseases selected from respiratory complaints, pulmonary diseases, gastrointestinal ailments and diseases and also inflammatory diseases of the joints, skin or eyes, cancers and diseases of the peripheral or central nervous system, but particularly for the treatment of inflammatory and obstructive diseases such as COPD, chronic sinusitis, asthma, Crohn's disease, and ulcerative colitis.

In a preferred aspect the invention relates to the use of the combination containing one or more PDE4-inhibitors—particularly one or more of the PDE4-inhibitors according to formula 1—and of the at least one NSAID (2) for preparing a drug combination for the treatment of the above mentioned diseases, characterised in that the PDE4 inhibitor—particularly the PDE4 inhibitor of formula 1—and the at least one NSAID (2) are administered together and simultaneously in a single formulation, this single formulation preferably being an oral formulation such as for example a tablet, capsule or the like.

It is also preferable to use the combination containing one or more PDE4-inhibitors—particularly one or more of the PDE4-inhibitors according to formula 1- and the at least one NSAID (2) to prepare a drug combination for the treatment of the above mentioned diseases, characterised in that the PDE4 inhibitor—particularly the PDE4 inhibitor of formula 1- and the at least one NSAID (2) are administered in two separate formulations separated from one another within a time interval of 0 to 6 hours. In this separate administration in two separate formulations the formulation containing the PDE4 inhibitor—particularly the PDE4 inhibitor of formula 1—may be an oral or inhalative formulation, but is preferably an oral formulation, and the formulation containing the at least one NSAID (2) is preferably an oral formulation. Moreover, when the combination is used in separate formulations to prepare a drug combination for the treatment of the above mentioned diseases the formulation containing the PDE4 inhibitor—particularly the PDE4 inhibitor of formula 1—is preferably administered once a day and the formulation containing the at least one NSAID (2) is preferably administered either once or twice a day.

It is also preferable to use the combination containing one or more PDE4-inhibitors—particularly one or more of the PDE4-inhibitors according to formula 1- and the at least one NSAID (2) to prepare a drug combination for the treatment of the above mentioned diseases, using PDE4-inhibitors of general formula 1, wherein $R^1$ is H, $R^2$ is a group selected from among

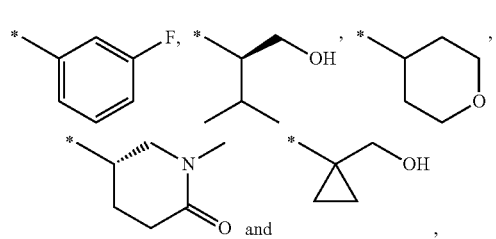

$R^3$ is a group selected from among

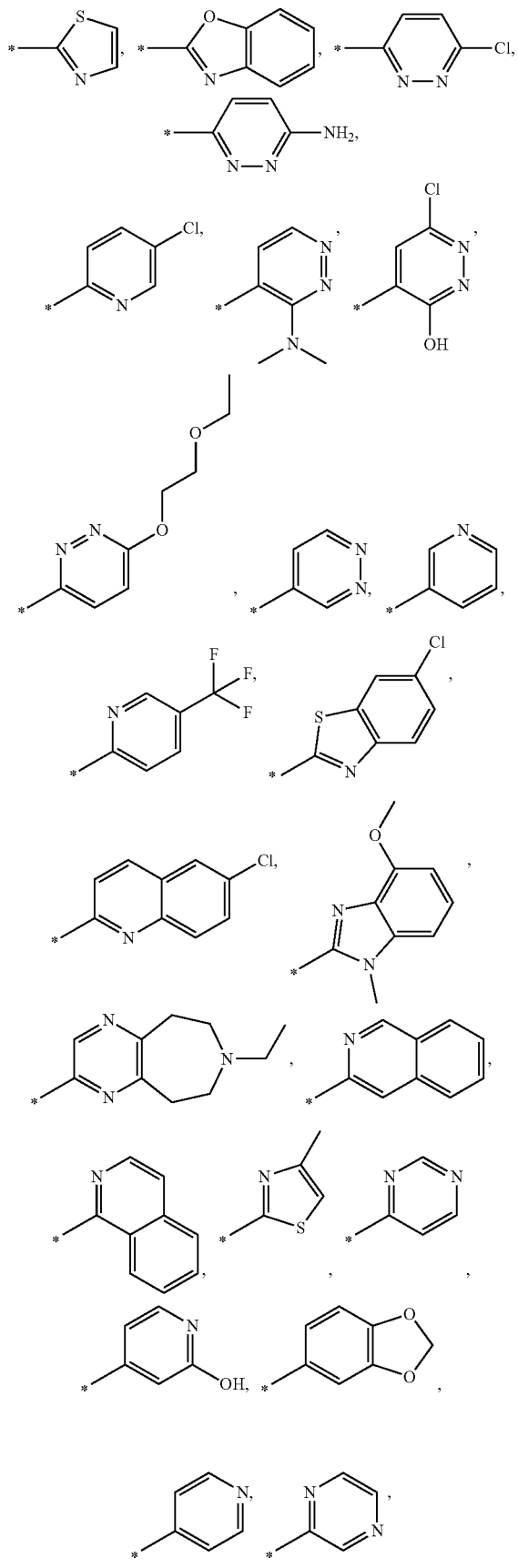

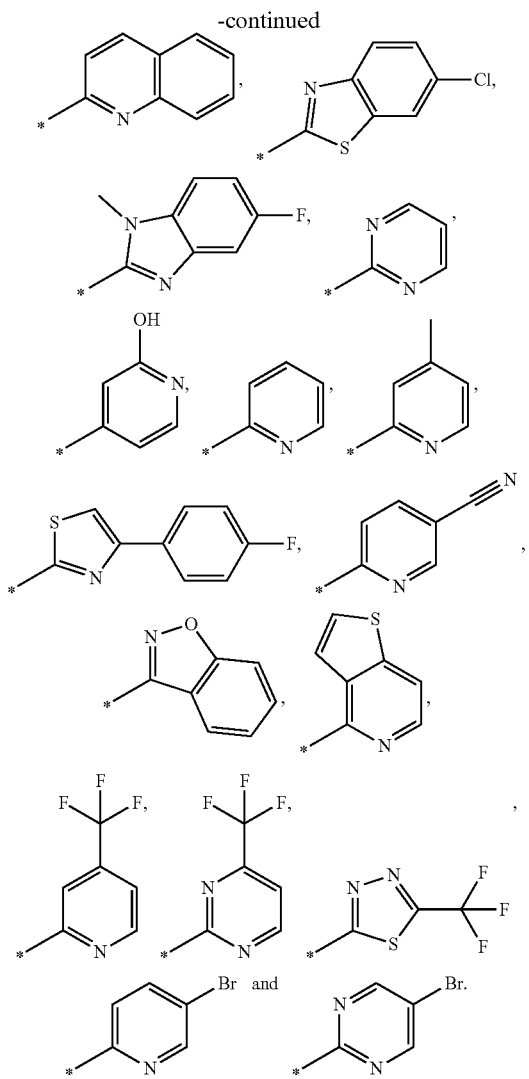

In particular, in the uses mentioned above, the PDE4-inhibitors of formula 1 are selected from:

1.1 (3-fluorophenyl)-[5-oxo-2-(4-thiazol-2-yl-piperazin-1-yl)-6,7-dihydro-5H-5λ⁴-thieno[3,2-d]pyrimidin-4-yl]-amine
1.2 (R)-3-methyl-2-[5-oxo-2-(4-thiazol-2-yl-piperazin-1-yl)-6,7-dihydro-5H-5λ⁴-thieno[3,2-d]pyrimidin-4-ylamino]-butan-1-ol
1.3 [2-(4-benzoxazol-2-yl-piperazin-1-yl)-5-oxo-6,7-dihydro-5H-5λ☐⁴-thieno[3,2-d]pyrimidin-4-yl]-(3-fluorophenyl)-amine
1.4 [2-(4-benzoxazol-2-yl-piperazin-1-yl)-5-oxo-6,7-dihydro-5H-5λ⁴-thieno[3,2-d]pyrimidin-4-yl]-(tetrahydropyran-4-yl)-amine
1.5 (R)-2-{2-[4-(6-chloropyridazin-3-yl)-piperazin-1-yl]-5-oxo-6,7-dihydro-5H-5λ⁴-thieno[3,2-d]pyrimidin-4-ylamino}-3-methylbutan-1-ol
1.6 {2-[4-(6-chloropyridazin-3-yl)-piperazin-1-yl]-5-oxo-6,7-dihydro-5H-5λ⁴-thieno[3,2-d]pyrimidin-4-yl}-(3-fluorophenyl)-amine
1.7 (R)-2-[2-(4-benzoxazol-2-yl-piperazin-1-yl)-5-oxo-6,7-dihydro-5H-5λ⁴-thieno[3,2-d]pyrimidin-4-ylamino]-3-methylbutan-1-ol
1.8 (1-{2-[4-(5-chloropyridin-2-yl)-piperazin-1-yl]-5-oxo-6,7-dihydro-5H-5λ⁴-thieno[3,2-d]pyrimidin-4-ylamino}-cyclopropyl)-methanol
1.9 {2-[4-(5-chloropyridin-2-yl)-piperazin-1-yl]-5-oxo-6,7-dihydro-5H-5λ⁴-thieno[3,2-d]pyrimidin-4-yl}-(tetrahydropyran-4-yl)-amine
1.10 {2-[4-(3-dimethylaminopyridazin-4-yl)-piperazin-1-yl]-5-oxo-6,7-dihydro-5H-5λ⁴-thieno[3,2-d]pyrimidin-4-yl}-(3-fluorophenyl)-amine
1.11 6-chloro-4-{4-[4-(3-fluorophenylamino)-5-oxo-6,7-dihydro-5H-5λ⁴-thieno[3,2-d]pyrimidin-2-yl]-piperazin-1-yl}-pyridazin-3-ol
1.12 2-{4-[6-(2-ethoxyethoxy)-pyridazin-3-yl]-piperazin-1-yl}-5-oxo-6,7-dihydro-5H-5λ⁴-thieno[3,2-d]pyrimidin-4-yl)-(3-fluorophenyl)-amine
1.13 (3-fluorophenyl)-[5-oxo-2-(4-pyridazin-4-yl-piperazin-1-yl)-6,7-dihydro-5H-5λ⁴-thieno[3,2-d]pyrimidin-4-yl]-amine
1.14 (R)-2-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-ylamino}-3-methylbutan-1-ol
1.15 (R-2-{2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-ylamino}-3-methylbutan-1-ol
1.16 (R)-3-methyl-2-[5-oxo-2-(4-pyrimidin-4-yl-piperazin-1-yl)-6,7-dihydro-5H-5λ⁴-thieno[3,2-d]pyrimidin-4-ylamino]-butan-1-ol
1.17 4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridin-2-ol
1.18 (R)-3-methyl-2-[5-oxo-2-(4-pyridin-4-yl-piperazin-1-yl)-6,7-dihydro-5H-5λ⁴-thieno[3,2-d]pyrimidin-4-ylamino]-butan-1-ol
1.19 (R)-2-{2-[4-(3-dimethylaminopyridazin-4-yl)-piperazin-1-yl]-5-oxo-6,7-dihydro-5H-5λ⁴-thieno[3,2-d]pyrimidin-4-ylamino}-3-methylbutan-1-ol
1.20 6-chloro-4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridazin-3-ol
1.21 (R)-2-(2-{4-[6-(2-ethoxyethoxy)-pyridazin-3-yl]-piperazin-1-yl}-5-oxo-6,7-dihydro-5H-5λ⁴-thieno[3,2-d]pyrimidin-4-ylamino)-3-methylbutan-1-ol
1.22 (R)-3-methyl-2-[5-oxo-2-(4-pyridazin-4-yl-piperazin-1-yl)-6,7-dihydro-5H-5λ⁴-thieno[3,2-d]pyrimidin-4-ylamino]-butan-1-ol
1.23 {1-[5-oxo-2-(4-pyrimidin-4-yl-piperazin-1-yl)-6,7-dihydro-5H-5λ⁴-thieno[3,2-d]pyrimidin-4-ylamino]-cyclopropyl}-methanol
1.24 {1-[5-oxo-2-(4-pyridin-4-yl-piperazin-1-yl)-6,7-dihydro-5H-5λ⁴-thieno[3,2-d]pyrimidin-4-ylamino]-cyclopropyl}-methanol
1.25 (S)-1-methyl-5-[5-oxo-2-(4-pyrimidin-4-yl-piperazin-1-yl)-6,7-dihydro-5H-5λ4-thieno[3,2-d]pyrimidin-4-ylamino]-piperidin-2-one
1.26 {2-[4-(5-fluoro-1-methyl-1H-benzoimidazol-2-yl)-piperazin-1-yl]-5-oxo-6,7-dihydro-5H-5λ4-thieno[3,2-d]pyrimidin-4-yl}-(tetrahydropyran-4-yl)-amine
1.27 [5-oxo-2-(4-pyridin-4-yl-piperazin-1-yl)-6,7-dihydro-5H-5λ4-thieno[3,2-d]pyrimidin-4-yl]-(tetrahydropyran-4-yl)-amine
1.28 (3-fluorophenyl)-{2-[4-(4-methoxy-1-methyl-1H-benzimidazol-2-yl)-piperazin-1-yl]-5-oxo-6,7-dihydro-5H-5λ4-thieno[3,2-d]pyrimidin-4-yl}-amine
1.29 {2-[4-(7-ethyl-6,7,8,9-tetrahydro-5H-pyrazino[2,3-d]azepin-2-yl)-piperazin-1-yl]-5-oxo-6,7-dihydro-5H-5λ4-thieno[3,2-d]pyrimidin-4-yl}-(3-fluorophenyl)-amine
1.30 (3-fluorophenyl)-[5-oxo-2-(4-pyrimidin-4-yl-piperazin-1-yl)-6,7-dihydro-5H-5λ4-thieno[3,2-d]pyrimidin-4-yl]-amine 1.31 4-{4-[4-(3-fluorophenylamino)-5-oxo-6,7-dihydro-5H-5λ4-thieno[3,2-d]pyrimidin-2-yl]-piperazin-1-yl}-pyridin-2-ol 1.32 (3-fluorophenyl)-[5-oxo-2-(4-pyridin-4-yl-piperazin-1-yl)-6,7-dihydro-5H-5λ4-thieno[3,2-d]pyrimidin-4-yl]-amine 1.33 (3-fluorophenyl)-(2-{4-[4-(4-fluorophenyl)-thiazol-2-yl]-piperazin-1-yl}-5-oxo-6,7-dihydro-5H-5λ4-thieno[3,2-d]pyrimidin-4-yl)-amine 1.34 [2-(4-benzo[d]isoxazol-3-yl-piperazin-1-yl)-5-oxo-6,7-dihydro-5H-5λ4-thieno[3,2-d]pyrimidin-4-yl]-(3-fluorophenyl)-amine 1.35 (R)-2-(2-{4-[4-(4-fluorophenyl)-thiazol-2-yl]-piperazin-1-yl}-5-oxo-6,7-dihydro-5H-5λ4-thieno[3,2-d]pyrimidin-4-ylamino)-3-methylbutan-1-ol 1.36 (R)-2-[2-(4-benzo[d]isoxazol-3-yl-piperazin-1-yl)-5-oxo-6,7-dihydro-5H-5λ4-thieno[3,2-d]pyrimidin-4-ylamino]-3-methylbutan-1-ol.

In these above mentioned uses the NSAIDs (2) are preferably selected from among: aceclofenac (2.1), acemetacin (2.2), acetylsalicylic acid (2.3), alclofenac (2.4), alminoprofen (2.5), amfenac (2.6), ampiroxicam (2.7), antolmetinguacil (2.8), anirolac (2.9), antrafenine (2.10), azapropazone (2.11), benorilate (2.12), bermoprofen (2.13), bindarit (2.14), bromfenac (2.15), bucloxinic acid (2.16), bucolom (2.17), bufexamac (2.18), bumadizone (2.19), butibufen (2.20), butixirate (2.21), carbasalate calcium (2.22), carprofen (2.23), choline magnesium trisalicylate (2.24), celecoxib (2.25), cinmetacin (2.26), cinnoxicam (2.27), clidanac (2.28), clobuzarit (2.29), deboxamet (2.30), dexibuprofen (2.31), dexketoprofen (2.32), diclofenac (2.33), diflunisal (2.34), droxicam (2.35), eltenac (2.36), enfenamic acid (2.37), etersalate (2.38), etodolac (2.39), etofenamat (2.40), etoricoxib (2.41), feclobuzon (2.42), felbinac (2.43), fenbufen (2.44), fenclofenac (2.45), fenoprofen (2.46), fentiazac (2.47), fepradinol (2.48), feprazone (2.49), flobufen (2.50), floctafenin (2.51), flufenamic acid (2.52), flufenisal (2.53), flunoxaprofen (2.54), flurbiprofen (2.55), flurbiprofenaxetil (2.56), furofenac (2.57), furprofen (2.58), glucametacin (2.59), ibufenac (2.60), ibuprofen (2.61), indobufen (2.62), indometacin (2.63), indometacinfarnesil (2.64), indoprofen (2.65), isoxepac (2.66), isoxicam (2.67), ketoprofen (2.68), ketorolac (2.69), lobenzarit (2.70), lonazolac (2.71), lornoxicam (2.72), loxoprofen (2.73), lumiracoxib (2.74), meclofenamic acid (2.75), meclofen, mefenamic acid (2.76), meloxicam (2.77), mesalazin (2.78), miroprofen (2.79), mofezolac (2.80), nabumetone (2.81), naproxen (2.82), nifluminic acid (2.83), olsalazine (2.84), oxaprozin (2.85), oxipinac (2.86), oxyphenbutazone (2.87), parecoxib (2.88), phenylbutazone (2.89), pelubiprofen (2.90), pimeprofen (2.91), pirazolac (2.92), priroxicam (2.93), pirprofen (2.94), pranoprofen (2.95), prifelon (2.96), prinomod (2.97), proglumetacin (2.98), proquazone (2.99), protizinic acid (2.100), rofecoxib (2.101), romazarit (2.102), salicylamide (2.103), salicylic acid (2.104), salmistein (2.105), salnacedin (2.106), salsalate (2.107), sulindac (2.108), sudoxicam (2.109), suprofen (2.110), talniflumat (2.111), tenidap (2.112), tenosal (2.113), tenoxicam (2.114), tepoxalin (2.115), tiaprofenic acid (2.116), taramide (2.117), tilnoprofenarbamel (2.118), timegadine (2.119), tinoridine (2.120), tiopinac (2.121), tolfenamic acid (2.122), tolmetin (2.123), ufenamate (2.124), valdecoxib (2.125), ximoprofen (2.126), zaltoprofen (2.127) and zoliprofen (2.128).

More preferably, in the uses mentioned above, the NSAIDs (2) are selected from among acetylsalicylic acid (2.3), celecoxib (2.25), diclofenac (2.33), ibuprofen (2.61), indometacin (2.63), lumiracoxib (2.74), meloxicam (2.77), naproxen (2.82) and priroxicam (2.93).

Particularly, in the uses mentioned above, the NSAIDs (2) are selected from among
- acetylsalicylic acid (2.3), preferably in a single dose of 50 to 2000 mg, more preferably 100 to 500 mg,
- diclofenac (2.33), preferably in a single dose of 25 to 150 mg, more preferably 25 to 100 mg,
- meloxicam (2.77), preferably in a single dose of 7.5 to 30 mg, more preferably 10 to 20 mg
- naproxen (2.82), preferably in a single dose of 250 to 1000 mg, more preferably 250 to 750 mg, and
- ibuprofen (2.61), preferably in a single dose of 200 to 2400 mg, more preferably 200 to 800 mg used, while this single dose may be administered once or twice a day.

Preferably, in the above-mentioned uses of the combination for treating the above mentioned diseases the PDE4 inhibitor of general formula 1 is given in a single dose of 0.01 mg to 50 mg, preferably 0.05 to 30 mg, more preferably 0.1 to 20 mg, particularly 0.5 to 10 mg.

In particular, the invention relates to the above mentioned uses, wherein the or at least one or more of the PDE4 inhibitor-mediated side effects is substantially reduced or prevented completely, by comparison with the sole administration of the PDE4 inhibitor used in the drug combination.

The invention also particularly relates to the use of NSAIDs, preferably as hereinbefore defined and according to the preferred definitions, for reducing or avoiding one or more PDE4 inhibitor-mediated side effects.

These PDE4 inhibitor-mediated side effects are preferably selected from among weight loss, leukocytosis, neutrophilia, nausea, vomiting, diarrhoea (including the occurrence of inflammatory parameters and the proliferation of fibroblasts in the mesentery). These PDE4 inhibitor-mediated side effects are more preferably selected from weight loss, leukocytosis, neutrophilia and diarrhoea. These PDE4 inhibitor-mediated side effects relate particularly to the occurrence of diarrhoea.

Synthesis Instructions

The compounds of general formula (I) may be prepared according to the following general synthesis scheme in which the substituents of general formula (I) have the meanings given hereinbefore. These methods are to be understood as illustrating the invention without restricting it to their subject-matter.

GENERAL SYNTHESIS SCHEME

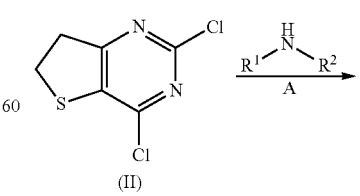

(II)

For the preparation of (II) see WO06111549

-continued

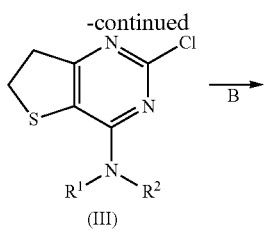

(III)

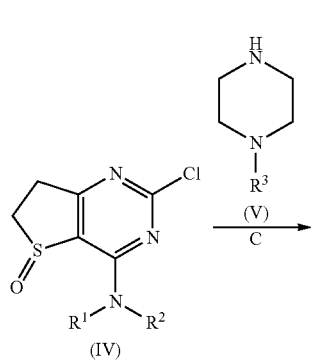

(I)

1. SYNTHESIS OF (3-FLUOROPHENYL)-[5-OXO-2-(4-THIAZOL-2-YL-PIPERAZIN-1-YL)-6,7-DIHYDRO-5H-5λ⁴-THIENO[3,2-D]PYRIMIDIN-4-YL]-AMINE (EXAMPLE 1.1)

1.1 (2-chloro-6,7-dihydrothieno[3,2-d]pyrimidin-4-yl)-(3-fluorophenyl)-amine (III-1)

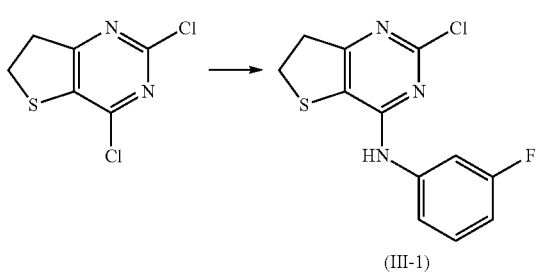 [SMILES: Clc1nc(Cl)c2c(n1)CCS2 ; Fc1cccc(Nc2nc(Cl)nc3c2SCC3)c1 ; "(III-1)"]

(III-1)

4 g (II) are placed in 15 ml dimethylformamide, then 4.5 ml diisopropylethylamine are added followed by 2.5 ml 3-fluorophenylamine. The reaction mixture is heated to 120° C. until there is no further reaction then cooled and evaporated down. The residue is mixed with water. The product is extracted with dichloromethane and purified by chromatography (silica gel, petroleum ether/ethyl acetate 80/20 to 60/40). 2.6 g (III-1) are obtained in the form of a solid. Analytical HPLC (method A): RT=3.27 min.

1.2 2-chloro-5-oxo-6,7-dihydro-5H-5λ⁴-thieno[3,2-d]pyrimidin-4-yl)-(3-fluorophenyl)-amine (IV-1)

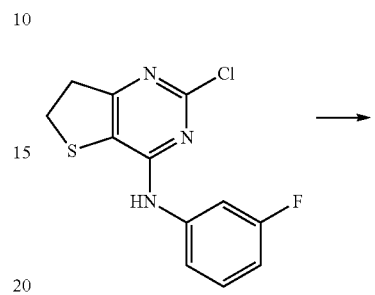

(IV-1)

0.102 g S-(−)-1,1'-bi-2-naphthol are placed in 0.5 ml chloroform under argon, then 0.052 ml titanium(IV)-isopropoxide and 0.064 ml of water are added. The reaction mixture is stirred for 45 minutes at ambient temperature. Then a suspension of 0.5 g (III-1) in 25 ml chloroform is added. The reaction mixture is cooled to −2°/−4° C. and after 20 minutes 0.323 ml tert-butylhydroperoxide 5-6 M in decane are added dropwise. The reaction mixture is stirred further at −2/−4° C. until there is no further reaction, and mixed with water. The product is extracted with dichloromethane and purified by chromatography (silica gel, dichloromethane/methanol 100/0 to 95/5). 0.47 g (IV-1) are obtained in the form of a solid. Analytical HPLC-MS (method A): RT=1.16 min.

1.3 (3-fluorophenyl)-[5-oxo-2-(4-thiazol-2-yl-piperazin-1-yl)-6,7-dihydro-5H-5λ⁴-thieno[3,2-d]pyrimidin-4-yl]-amine (Example 1.1)

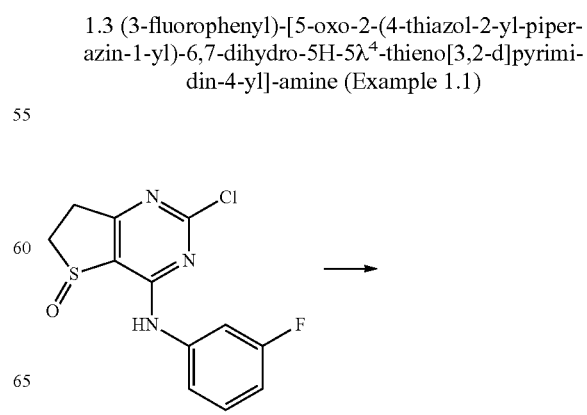

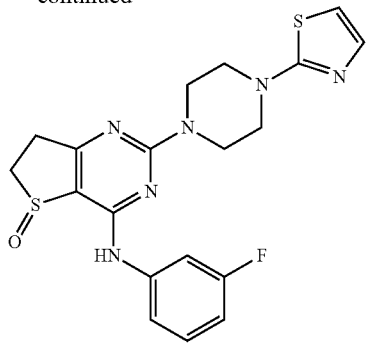

Example 1.1

0.2 g (IV-1) is placed in 3 ml dioxane, 240 µl diisopropylethylamine and 0.24 g 1-thiazol-2-yl-piperazin are added. The reaction mixture is heated to 120° C. in the microwave until there is no further reaction and mixed with water. The precipitated solid is suction filtered and purified by chromatography (silica gel, ethyl acetate/methanol 100/0 to 80/20). 0.17 g Example 1.1 are obtained in the form of a solid. Analytical HPLC-MS (method A): RT=1.07 min.

2. SYNTHESIS OF (R)-3-METHYL-2-[5-OXO-2-(4-THIAZOL-2-YL-PIPERAZIN-1-YL)-6,7-DIHYDRO-5H-5λ⁴-THIENO[3,2-D]PYRIMIDIN-4-YLAMINO]-BUTAN-1-OL (EXAMPLE 1.2)

2.1 (R)-2-(2-chloro-6,7-dihydro-thieno[3,2-d]pyrimidin-4-ylamino)-3-methyl-butan-1-ol (III-2)

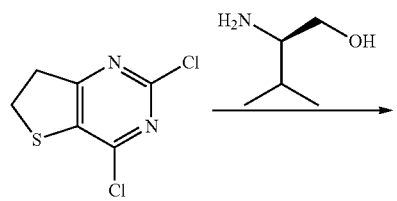

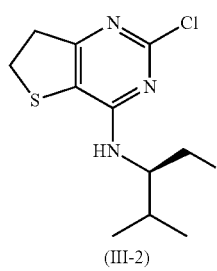

(III-2)

7.2 g 2,4-dichloro-6,7-dihydro-thieno[3,2-d]pyrimidine (II) are placed in 36 ml dioxane, then 18 ml diisopropylethylamine are added followed by 6.1 g (R)-(−)-2-amino-3-methyl-1-butanol. The reaction mixture is heated to 100° C. until there is no further reaction, then cooled and evaporated down. The residue is treated with petroleum ether/ethyl acetate 9:1 in the ultrasound bath and the solid is suction filtered and dried. 8.3 g (III-2) are obtained in the form of a solid. Analytical HPLC (method A): RT=2.75 min 2.2 (R)-2-(2-chloro-5-oxo-6,7-dihydro-5H-5λ⁴-thieno[3,2-d]pyrimidin-4-ylamino)-3-methyl-butan-1-ol (IV-2)

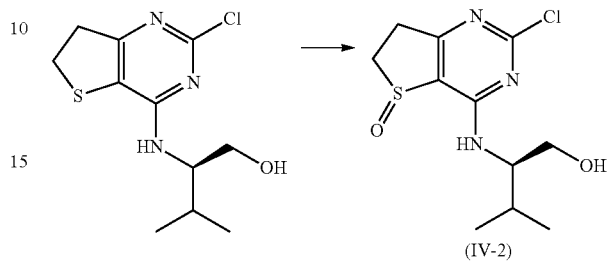

(IV-2)

4.1 g S-(−)-1,1'-bi-2-naphthol are placed in 15 ml chloroform under argon, then 0.44 ml titanium(IV)-isopropoxide and 0.54 ml of water are added. The reaction mixture is stirred for 1 hour at ambient temperature. Then a suspension of 4.1 g (III-2) in 107 ml dichloromethane is added. The reaction mixture is cooled to −2° C. and after 30 minutes 2.7 ml tert-butylhydroperoxide 5-6 M in decane are added dropwise. The reaction mixture is stirred further at −2° C. until there is no further reaction and made basic with NH₄OH. The product is extracted with dichloromethane and purified by chromatography (silica gel, ethyl acetate/methanol 100/0 to 86/14). 2.45 g (IV-2) are obtained in the form of a solid. Analytical HPLC-MS (method A): RT=0.98 min 2.3 (R)-3-methyl-2-[5-oxo-2-(4-thiazol-2-yl-piperazin-1-yl)-6,7-dihydro-5H-5λ⁴-thieno[3,2-d]pyrimidin-4-ylamino]-butan-1-ol (Example 1.2)

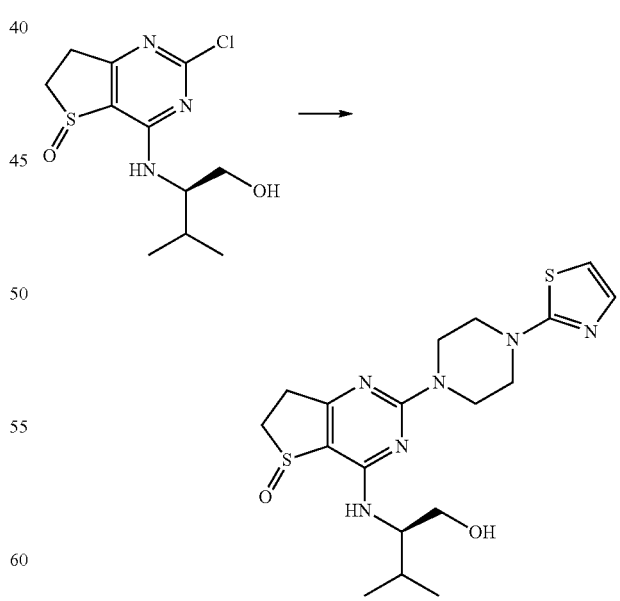

Example 1.2

Starting from 0.2 g (IV-2) and 0.245 g 1-thiazol-2-yl-piperazine, 0.13 g Example 1.2 are prepared analogously to Example 1.1 (cf. 1.3). The reaction mixture is mixed with water and the product is extracted with dichloromethane and purified by chromatography (silica gel, dichloromethane/methanol 100/0 to 90/10). Analytical HPLC-MS (method A): RT=0.87 min.

3. SYNTHESIS OF [2-(4-BENZOXAZOL-2-YL-PIPERAZIN-1-YL)-5-OXO-6,7-DIHYDRO-5H-5λ☐⁴-THIENO[3,2-D]PYRIMIDIN-4-YL]-(3-FLUOROPHENYL)-AMINE (EXAMPLE 1.3)

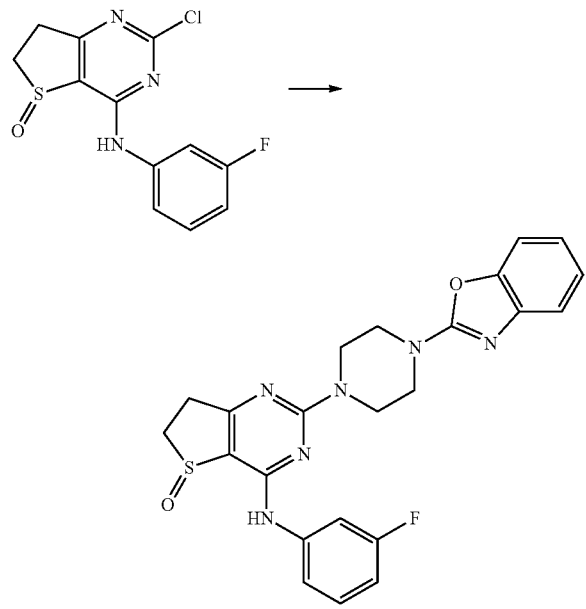

Example 1.3

Starting from 0.2 g (IV-1) (cf. 1.2) and 0.287 g 2-piperazin-1-yl-benzoxazole 0.31 g Example 1.3 are prepared analogously to Example 1.1 (cf. 1.3). The reaction mixture is mixed with water and the product is suction filtered. Analytical HPLC-MS (method A): RT=1.23 min.

4. SYNTHESIS OF [2-(4-BENZOXAZOL-2-YL-PIPERAZIN-1-YL)-5-OXO-6,7-DIHYDRO-5H-5λ⁴-THIENO[3,2-D]PYRIMIDIN-4-YL]-(TETRAHYDROPYRAN-4-YL)-AMINE (EXAMPLE 1.4)

4.1 (2-chloro-6,7-dihydrothieno[3,2-d]pyrimidin-4-yl)-(tetrahydropyran-4-yl)-amine (III-3)

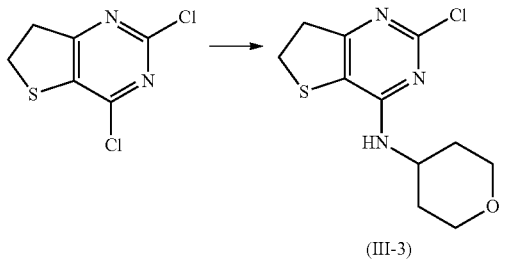 [SMILES: Clc1nc(Cl)c2c(n1)CCS2 ; Clc1nc2c(c(NC3CCOCC3)n1)SCC2 ; "(III-3)"]

(III-3)

0.68 g (II) are placed in 6 ml dioxane, then 1.72 ml diisopropylethylamine are added followed by 0.6 g 4-aminotetrahydropyran. The reaction mixture is heated to 130° C. until there is no further reaction, then cooled and evaporated down. The product is treated with water in the ultrasound bath and the solid is suction filtered and dried. 0.66 g (III-3) are obtained. Analytical HPLC-MS (method A): RT=1.08 min.

4.2 (2-chloro-5-oxo-6,7-dihydro-5H-5λ⁴-thieno[3,2-d]pyrimidin-4-yl)-(tetrahydropyran-4-yl)-amine (IV-3)

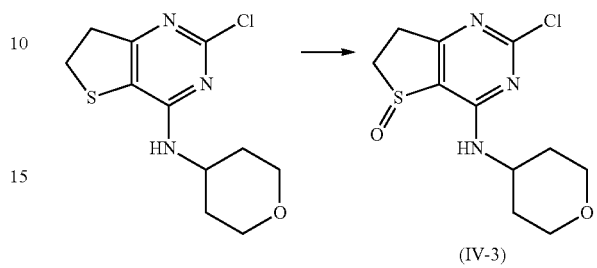

(IV-3)

0.14 g S-(−)-1,1'-bi-2-naphthol are placed in 5 ml chloroform under argon, then 0.072 ml titanium(IV)-isopropoxide and 0.087 ml of water are added. The reaction mixture is stirred for 45 minutes at ambient temperature. Then a suspension of 0.66 g (III-3) in 25 ml chloroform is added. The reaction mixture is cooled to −10° C. and after 60 minutes 0.444 ml tert-butylhydroperoxide 5-6 M in decane are added dropwise. The reaction mixture is stirred further at −10 to −4° C. until there is no further reaction and mixed with water. The product is extracted with dichloromethane and purified by chromatography (silica gel, ethyl acetate/methanol 100/0 to 80/20). 0.42 g (IV-3) are obtained in the form of a solid. Analytical HPLC-MS (method A): RT=0.94 min.

4.3 [2-(4-benzoxazol-2-yl-piperazin-1-yl)-5-oxo-6,7-dihydro-5H-5λ⁴-thieno[3,2-d]pyrimidin-4-yl]-(tetrahydropyran-4-yl)-amine (Example 1.4)

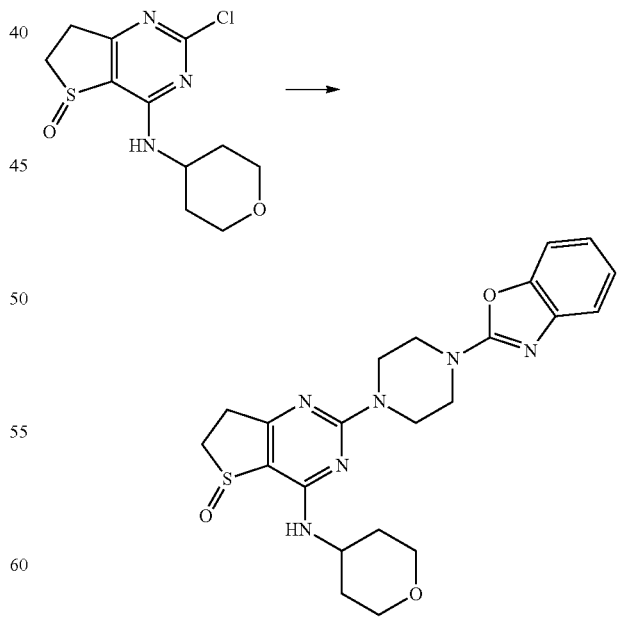

Example 1.4

Starting from 0.2 g (IV-3) and 0.315 g 2-piperazin-1-yl-benzoxazole, 0.3 g Example 1.4 are prepared and worked up analogously to Example 1.3 (cf. 3.). Analytical HPLC-MS (method A): RT=1.04 min.

5. SYNTHESIS OF (R)-2-{2-[4-(6-CHLOROPYRIDAZIN-3-YL)-PIPERAZIN-1-YL]-5-OXO-6,7-DIHYDRO-5H-5λ⁴-THIENO[3,2-D]PYRIMIDIN-4-YLAMINO}-3-METHYLBUTAN-1-OL (EXAMPLE 1.5)

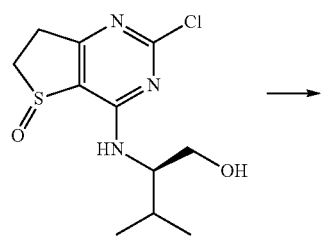

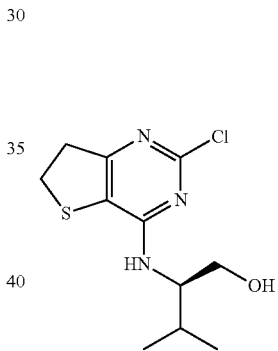

Example 1.5

Starting from 0.2 g (IV-2) (cf. 2.2) and 0.287 g 3-chloro-6-piperazin-1-yl-pyridazine, 0.257 g Example 1.5 are prepared and worked up analogously to Example 1.3 (cf. 3.). Analytical HPLC-MS (method A): RT=0.98 min.

6. SYNTHESIS OF {2-[4-(6-CHLOROPYRIDAZIN-3-YL)-PIPERAZIN-1-YL]-5-OXO-6,7-DIHYDRO-5H-5λ⁴-THIENO[3,2-D]PYRIMIDIN-4-YL}-(3-FLUOROPHENYL)-AMINE (EXAMPLE 1.6)

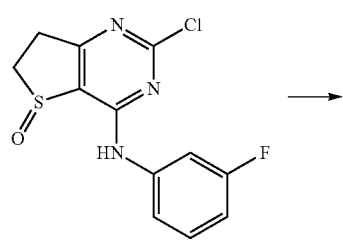

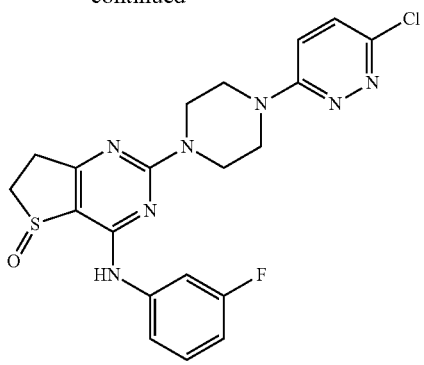

Example 1.6

Starting from 0.2 g (IV-1) (cf. 1.2) and 0.28 g 3-chloro-6-piperazin-1-yl-pyridazine, 0.31 g Example 1.6 are prepared analogously to Example 1.3 (cf. 3.). Analytical HPLC-MS (method A): RT=1.12 min.

7. SYNTHESIS OF (R)-2-[2-(4-BENZOXAZOL-2-YL-PIPERAZIN-1-YL)-5-OXO-6,7-DIHYDRO-5H-5λ⁴-THIENO[3,2-D]PYRIMIDIN-4-YLAMINO]-3-METHYLBUTAN-1-OL (EXAMPLE 1.7)

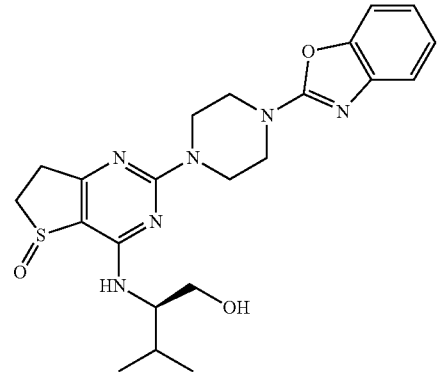

Example 1.7

Starting from 0.2 g (IV-2) (cf. 2.2) and 0.313 g 2-piperazin-1-yl-benzoxazole, 0.16 g Example 1.7 are prepared analogously to Example 1.1 (cf. 1.3). The reaction mixture is mixed with water and the product is extracted with dichloromethane and purified by chromatography (silica gel, ethyl acetate/methanol 100/0 to 80/20). Analytical HPLC-MS (method A): RT=1.06 min.

8. SYNTHESIS OF (1-{2-[4-(5-CHLOROPYRIDIN-2-YL)-PIPERAZIN-1-YL]-5-OXO-6,7-DIHYDRO-5H-5λ$^4$-THIENO[3,2-D]PYRIMIDIN-4-YLAMINO}-CYCLOPROPYL)-METHANOL (EXAMPLE 1.8)

8.1 tert-butyl (1-hydroxymethylcyclopropyl)-carbamidate:

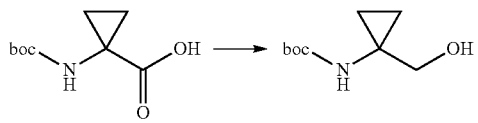

1-g 1-(BOC-amino)-cyclopropanecarboxylic acid is dissolved in 20 ml dimethoxyethane and cooled to −70° C. Then 0.65 ml N-methylmorpholine are added and 0.71 ml isobutylchloroformate in 5 ml dimethoxyethane are added dropwise. The reaction mixture is heated to −5° C. The precipitate is suction filtered. The eluate is cooled to −15° C. and 0.303 g sodium borohydride are slowly added. The reaction mixture is then stirred for 30 minutes at ambient temperature, mixed with water and the product is extracted with dichloromethane. The organic phase is dried and evaporated to dryness. 1.04 g product are obtained in the form of a solid. $^1$H NMR (400 MHz, DMSO): 1.36 (9H, s); 0.61 (2H, t); 0.52 (2H, t).

8.2 1-aminocyclopropanemethanol:

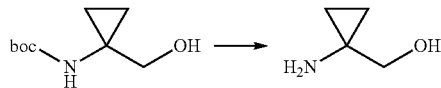

1.04 g tert-butyl (1-hydroxymethylcyclopropyl)-carbamidate are placed in 5 ml dioxane. 2.5 ml HCl in dioxane (4 mol/l) are added dropwise. The reaction mixture is stirred for 15 h at ambient temperature. The solvent is evaporated down by half and the precipitated solid is suction filtered. 0.5 g product are obtained as the hydrochloride. $^1$H NMR (400 MHz, DMSO): 5.27 (1H, t); 0.91 (2H, t); 0.71 (2H, t).

8.3 [1-(2-chloro-6,7-dihydrothieno[3,2-d]pyrimidin-4-ylamino)-cyclopropyl]-methanol (III-4)

1.4 g (II) are placed in 10 ml dioxane, then first 3.6 ml diisopropylethylamine are added followed by 1 g 1-aminocyclopropanemethanol (cf. 8.2). The reaction mixture is heated to 160° C. until there is no further reaction, then cooled and evaporated down.

The residue is treated with cyclohexane/ethyl acetate (8:2) in the ultrasound bath and the solid is suction filtered and dried. 1.24 g (III-4) are obtained in the form of a solid. Analytical HPLC-MS (method A): RT=1.01 min.

8.4 [1-(2-chloro-5-oxo-6,7-dihydro-5H-5λ$^4$-thieno[3,2-d]pyrimidin-4-ylamino)-cyclopropyl]-methanol (IV-4)

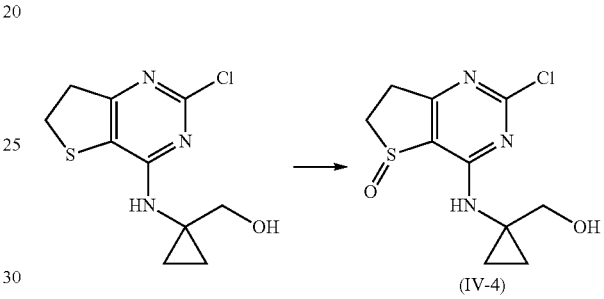

0.28 g S-(−)-1,1'-bi-2-naphthol are placed in 20 ml chloroform under argon, then 0.14 ml titanium(IV)-isopropoxide and 0.17 ml of water are added. The reaction mixture is stirred for 1 hour at ambient temperature. Then a suspension of 1.2 g (III-4) in 40 ml dichloromethane and 2 ml of methanol is added. The reaction mixture is cooled to −5° C. and after 30 minutes 0.91 ml of tert-butylhydroperoxide 5-6 M in decane are added dropwise. The reaction mixture is stirred further at −5° C. until there is no further reaction and made basic with NH$_4$OH. The aqueous phase is washed with dichloromethane and freeze-dried. 1 g (IV-4) is obtained in the form of a solid. Analytical HPLC-MS (method A) RT=0.85 min.

8.5 (1-{2-[4-(5-chloropyridin-2-yl)-piperazin-1-yl]-5-oxo-6,7-dihydro-5H-5λ$^4$-thieno[3,2-d]pyrimidin-4-ylamino}-cyclopropyl)-methanol (Example 1.8)

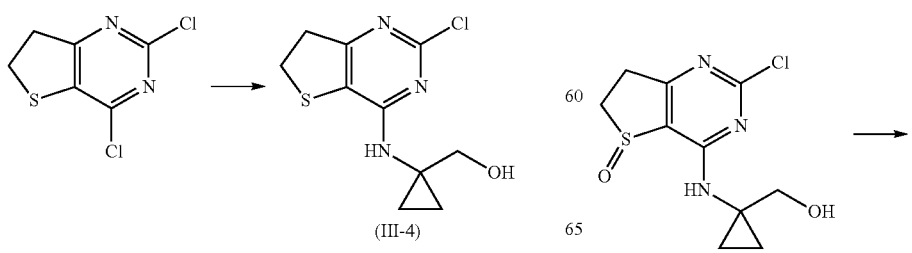

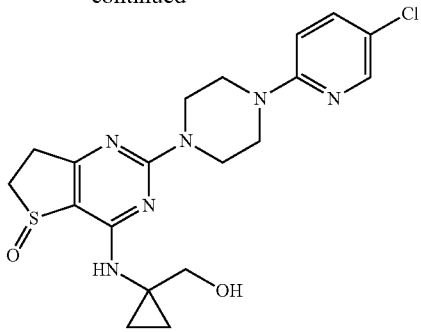

Example 1.8

0.1 g (IV-4) is placed in 3 ml N-methyl-2-pyrrolidone, then 182 µl diisopropylethylamine and 0.08 g 1-(5-chloropyridin-2-yl)-piperazine are added. The reaction mixture is heated to 120° C. in the microwave until there is no further reaction. The product is purified by chromatography (preparative HPLC, method A). Analytical HPLC-MS (method B): RT=1.09 min.

9. SYNTHESIS OF {2-[4-(5-CHLOROPYRIDIN-2-YL)-PIPERAZIN-1-YL]-5-OXO-6,7-DIHYDRO-5H-5λ⁴-THIENO[3,2-D]PYRIMIDIN-4-YL}-(TETRAHYDROPYRAN-4-YL)-AMINE (EXAMPLE 1.9)

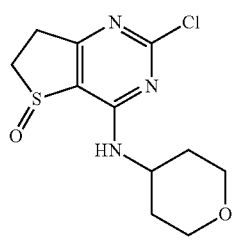

Example 1.9

Starting from 0.11 g (IV-3) (cf. 4.2) and 0.083 g 1-(5-chloropyridin-2-yl)-piperazine, 0.14 g Example 1.9 are prepared and purified analogously to Example 1.8 (cf. 8.5). Analytical HPLC-MS (method B): RT=1.14 min.

10. SYNTHESIS OF {2-[4-(3-DIMETHYLAMINOPYRIDAZIN-4-YL)-PIPERAZIN-1-YL]-5-OXO-6,7-DIHYDRO-5H-5λ⁴-THIENO[3,2-D]PYRIMIDIN-4-YL}-(3-FLUOROPHENYL)-AMINE (EXAMPLE 1.10)

10.1 3,4,6-trichloropyridazine

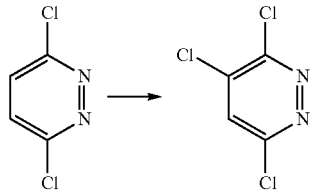 [SMILES: Clc1ccc(Cl)nn1 ; Clc1cc(Cl)c(Cl)nn1]

44 g 3,6-dichloropyridazine and 22 g aluminium trichloride are heated to 140° C. At this temperature 10.6 l chlorine are piped into the reaction mixture over a period of 4 hours. After cooling the product is extracted with toluene, washed with a 10% sodium chloride solution and distilled (bp=127-129° C.). 44.1 g of product are obtained.

10.2 3,6-dichloro-4-piperazin-1-yl-pyridazine

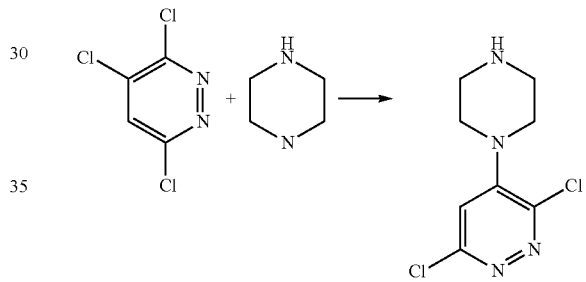

18 g 3,4,6-trichloro-pyridazine and 34 g piperazine are suspended in 100 ml of ethanol and stirred for 30 minutes at ambient temperature. The precipitated solid is suction filtered. 500 ml of water are added to the mother liquor and the precipitated product is suction filtered. 14 g product are obtained in the form of a solid. M.p.=111-115° C.

10.3 (6-chloro-4-piperazin-1-yl-pyridazin-3-yl)-dimethylamine

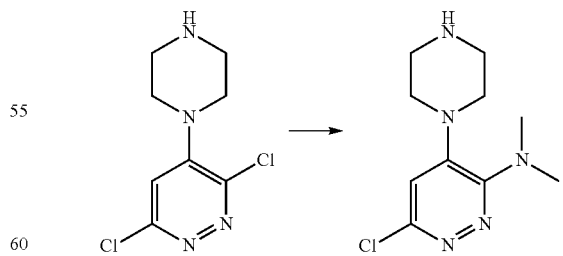

23 g 3,6-dichloro-4-piperazin-1-yl-pyridazine and 45 g dimethylamine are suspended in 200 ml of methanol and autoclaved for 4 hours at 100° C. The reaction mixture is evaporated to dryness and the product is extracted with chloroform and washed with sodium hydroxide solution. The hydrochloride is precipitated with an ethereal HCl solution. 27 g product are obtained. M.p.=291° C.

10.4 dimethyl-(4-piperazin-1-yl-pyridazin-3-yl)-amine (V-1)

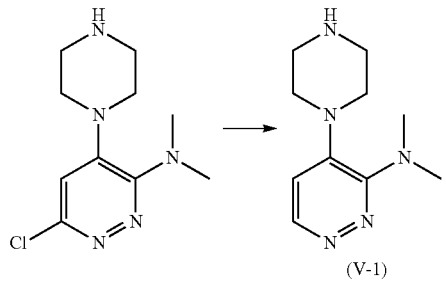

(V-1)

9.4 g (6-chloro-4-piperazin-1-yl-pyridazin-3-yl)-dimethylamine hydrochloride and 7.3 g sodium acetate are suspended in 150 ml of methanol and hydrogenated with 1 g Pd/C 10% at ambient temperature. The catalyst is suction filtered, the filtrate is evaporated to dryness and the product is extracted with chloroform and washed with sodium hydroxide solution.

The hydrochloride is precipitated with an ethereal HCl solution. 7 g (V-1) are obtained. M.p.=335° C.

10.5 {2-[4-(3-dimethylaminopyridazin-4-yl)-piperazin-1-yl]-5-oxo-6,7-dihydro-5H-5λ$^4$-thieno[3,2-d]pyrimidin-4-yl}-(3-fluorophenyl)-amine (Example 1.10)

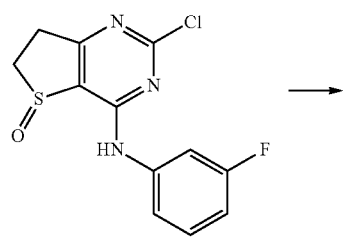

Example 1.10

(IV-1) (cf. 1.2) (0.1 mmol) is placed in 750 µl N-methyl-2-pyrrolidone (NMP) and 50 µl diisopropylethylamine, mixed with a solution of (V-1) (0.1 mmol) in 400 µl NMP and heated to 120° C. in the microwave for 30 min. Then 600 µL DMF are added, the reaction solution is purified by chromatography (preparative HPLC-MS, method A) and the product fractions are freeze-dried. Example 1.10 is obtained as the trifluoroacetate. Analytical HPLC-MS (method C): RT=1.61 min.

11. SYNTHESIS OF 6-CHLORO-4-{4-[4-(3-FLUOROPHENYLAMINO)-5-OXO-6,7-DIHYDRO-5H-5λ$^4$-THIENO[3,2-D]PYRIMIDIN-2-YL]-PIPERAZIN-1-YL}-PYRIDAZIN-3-OL (EXAMPLE 1.11)

11.1 (6-chloro-4-piperazin-1-yl-pyridazin-3-yloxy)-ethanol

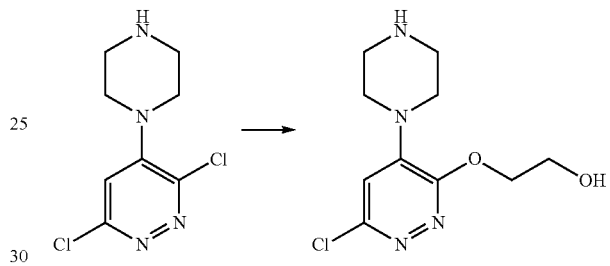

23 g 3,6-dichloro-4-piperazin-1-yl-pyridazine (cf. 10.2) are suspended in 100 ml ethyleneglycol and added dropwise to a suspension of 2.3 g sodium in 100 ml ethyleneglycol. The reaction mixture is heated to 100° C. for 3 hours and evaporated to dryness. The residue is suspended in acetonitrile and the solid is suction filtered. The mother liquor is evaporated to dryness, the product is extracted with dichloromethane and washed with conc. NaOH. The product is suspended in ethanol and precipitated as the fumarate with fumaric acid. 13 g product are obtained. M.p.=179° C.

11.2 6-chloro-4-piperazin-1-yl-pyridazin-3-ol (V-2)

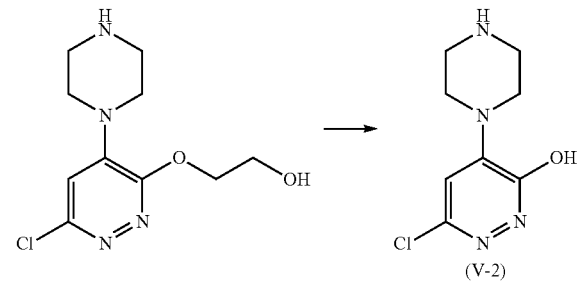

(V-2)

15 g (6-chloro-4-piperazin-1-yl-pyridazin-3-yloxy)-ethanol fumarate are suspended in 90 ml hydrogen bromide (48%). The reaction mixture is stirred for 1 hour at reflux temperature and evaporated to dryness. 19 g product are obtained as the hydrobromide. M.p.=35° C.

11.3 6-chloro-4-{4-[4-(3-fluorophenylamino)-5-oxo-6,7-dihydro-5H-5λ⁴-thieno[3,2-d]pyrimidin-2-yl]-piperazin-1-yl}-pyridazin-3-ol (Example 1.11)

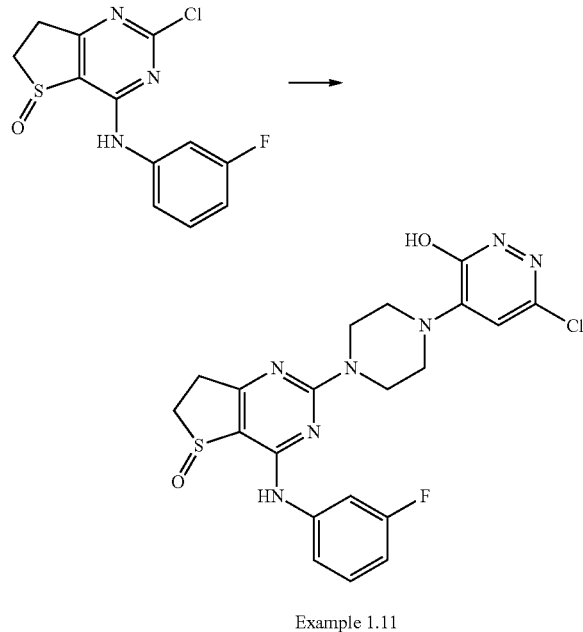

Example 1.11

Starting from (IV-1) (cf. 1.2) and (V-2) Example 1.11 is prepared and purified analogously to Example 1.10 (cf. 10.5). Analytical HPLC-MS (method C): RT=1.86 min.

12. SYNTHESIS OF (2-{4-[6-(2-ETHOXY-ETHOXY)-PYRIDAZIN-3-YL]-PIPERAZIN-1-YL}-5-OXO-6,7-DIHYDRO-5H-5λ⁴-THIENO[3,2-D]PYRIMIDIN-4-YL)(3-FLUOROPHENYL)-AMINE (EXAMPLE 1.12)

12.1 3-ethoxyethoxy-6-piperazin-1-yl-pyridazine (V-3)

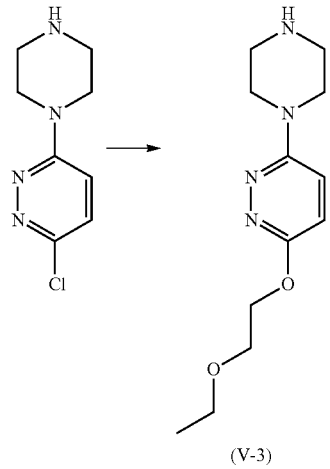

(V-3)

18 g 3-chloro-6-piperazin-1-yl-pyridazine and 30 g potassium hydroxide in 30 ml of water are suspended in 180 ml ethylglycol and stirred for 4 hours at reflux temperature. The reaction mixture is evaporated to dryness. The product is extracted with diethyl ether, washed with a concentrated potassium carbonate solution and distilled (bp=190° C.). 18 g (V-3) are obtained.

12.2 (2-{4-[6-(2-ethoxyethoxy)-pyridazin-3-yl]-piperazin-1-yl}-5-oxo-6,7-dihydro-5H-5λ⁴-thieno[3,2-d]pyrimidin-4-yl)-(3-fluorophenyl)-amine (Example 1.12)

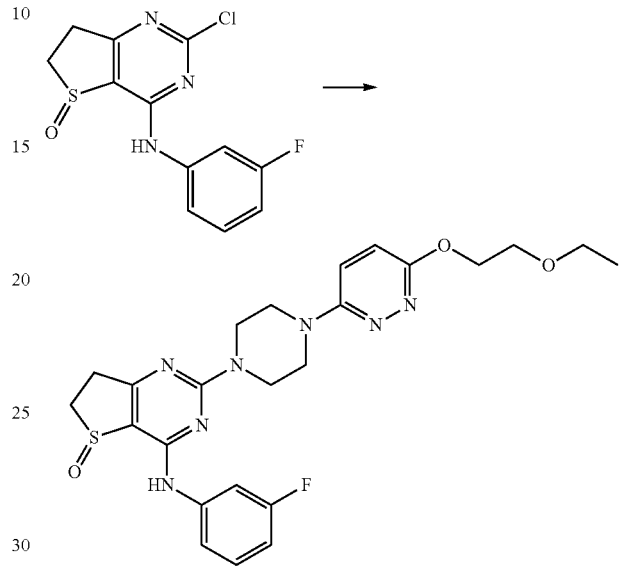

Example 1.12

Starting from (IV-1) (cf. 1.2) and (V-3) Example 1.12 is prepared and purified as the trifluoroacetate analogously to Example 1.10 (cf. 10.5). Analytical HPLC-MS (method C): RT=1.66 min.

13. SYNTHESIS OF (3-FLUOROPHENYL)-[5-OXO-2-(4-PYRIDAZIN-4-YL-PIPERAZIN-1-YL)-6,7-DIHYDRO-5H-5λ⁴-THIENO[3,2-D]PYRIMIDIN-4-YL]-AMINE (EXAMPLE 1.13)

13.1 4-piperazin-1-yl-pyridazine (V-4)

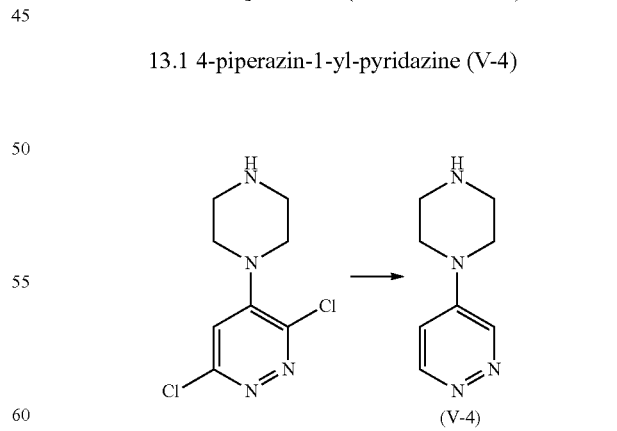

(V-4)

9.3 g 3,6-dichloro-4-piperazin-1-yl-pyridazine (cf. 10.2) and 6.5 g sodium acetate are suspended in 100 ml of methanol and hydrogenated with 1 g Pd/C 10% at ambient temperature. The catalyst is suction filtered and the filtrate is evaporated to dryness. The product is extracted with chloroform, washed with sodium hydroxide solution and precipitated as the hydrochloride with an ethereal HCl solution. 8.6 g (V-4) are obtained. M.p.>300° C.

13.2 (3-fluorophenyl)-[5-oxo-2-(4-pyridazin-4-yl-piperazin-1-yl)-6,7-dihydro-5H-5λ⁴-thieno[3,2-d]pyrimidin-4-yl]-amine (Example 1.13)

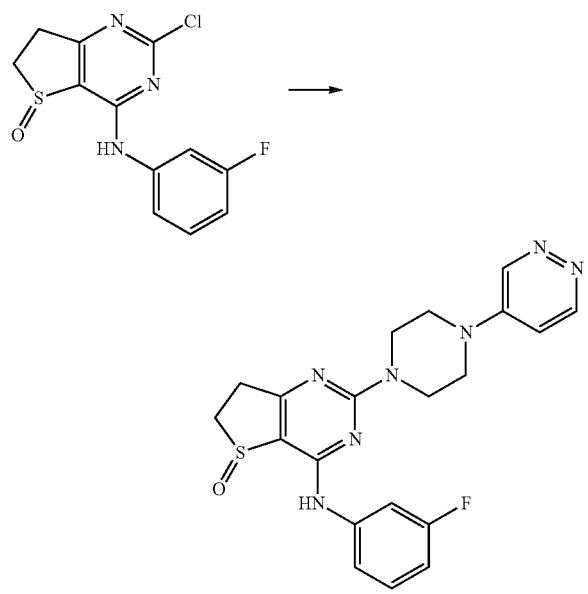

Example 1.13

Starting from (IV-1) (cf. 1.2) and (V-4) Example 1.13 is prepared and purified as the trifluoroacetate analogously to Example 1.10 (cf. 10.5). Analytical HPLC-MS (method C): RT=1.54 min.

14. SYNTHESIS OF (R)-2-{2-[4-(4-METHOXY-1-METHYL-1H-BENZIMIDAZOL-2-YL)-PIPER-AZIN-1-YL]-5-OXO-6,7-DIHYDRO-5H-5λ⁴-THIENO[3,2-D]PYRIMIDIN-4-YLAMINO}-3-METHYLBUTAN-1-OL TRIFLUOROACETATE (EXAMPLE 1.14)

14.1 tert-butyl (3-methoxy-2-nitrophenyl)-carbamidate

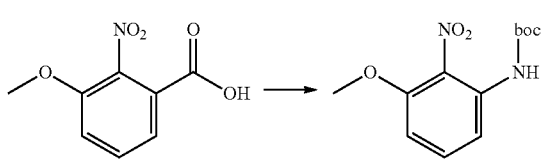

10 g 3-methoxy-2-nitrobenzoic acid and 7 ml triethylamine are placed in 100 ml tert-butanol and 11 ml diphenylphosphorylazide are added dropwise. The reaction mixture is then stirred for 6 hours at reflux temperature and evaporated to dryness. The product is extracted with ethyl acetate, then washed with a 10% citric acid, a saturated sodium hydrogen carbonate and a saturated sodium chloride solution. 12.4 g product are obtained as a solid. M.p.=90° C.

14.2 tert-butyl (3-methoxy-2-nitrophenyl)-methyl-carbamidate

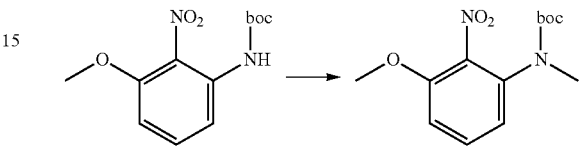

12.2 g tert-butyl (3-methoxy-2-nitrophenyl)-methyl-carbamidate are placed in 80 ml dimethylformamide and cooled at 0° C. 2.4 g sodium hydride (50% in mineral oil) are slowly added. The reaction mixture is stirred for 30 minutes at 0° C. Then 3.1 ml methyl iodide are added dropwise. The reaction mixture is stirred for 2 hours at ambient temperature and mixed with water. The product is extracted with ethyl acetate. 12.5 g product are obtained as an oil.

14.3 (3-methoxy-2-nitrophenyl)-methylamine

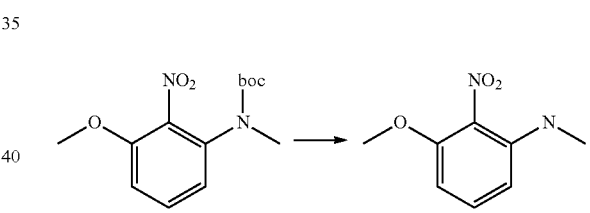

12.5 g tert-butyl (3-methoxy-2-nitrophenyl)-methyl-carbamidate and 78 ml hydrochloric acid (4 M) are suspended in 300 ml of ethyl acetate and heated for 5 hours at 60° C. The reaction mixture is evaporated to dryness, the residue is combined with a saturated sodium hydrogen carbonate solution and the product is extracted with ethyl acetate. 7.5 g product are obtained in the form of a solid. M.p=58-59° C.

14.4 3-methoxy-N'-methylbenzene-1,2-diamine

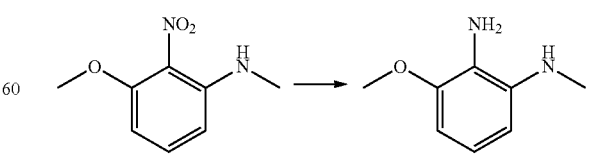

7.4 g (3-methoxy-2-nitrophenyl)-methylamine are suspended in 150 ml of ethyl acetate and hydrogenated with 1 g Pd/C 10% at a pressure of 50 psi and at ambient temperature.

After 4.5 hours the catalyst is suction filtered and the filtrate is evaporated to dryness. 5.9 g of the product are obtained as an oil.

14.5 4-methoxy-1-methyl-1,3-dihydrobenzimidazol-2-one

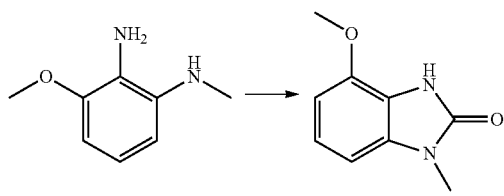

5.9 g 3-methoxy-N-1-methylbenzol-1,2-diamine are suspended in 70 ml of tetrahydrofuran and 6.3 g N,N'-carbonyldiimidazole are added. The reaction mixture is stirred for 5 hours at ambient temperature, mixed with water and the product is extracted with ethyl acetate. 3.9 g product are obtained as a solid.

14.6 2-chloro-4-methoxy-1-methyl-1H-benzimidazole

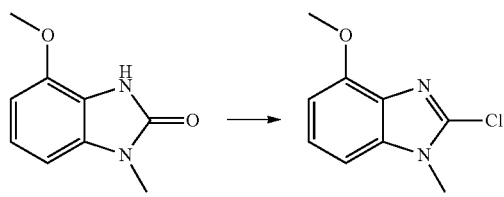

3.7 g 4-methoxy-1-methyl-1,3-dihydrobenzimidazol-2-one are suspended in 15 ml phosphorus oxychloride. The reaction mixture is stirred for 3 hours at reflux temperature, ice water is slowly added and the mixture is made alkaline with conc. ammonia. The precipitated product is suction filtered. 3.6 g product are obtained in the form of a solid. M.p.=118-119° C.

14.7 4-methoxy-1-methyl-2-piperazin-1-yl-1-benzimidazole (V-5)

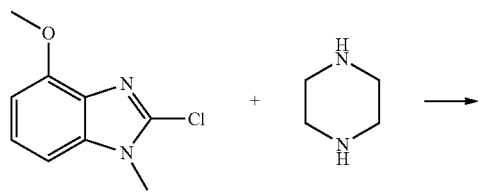

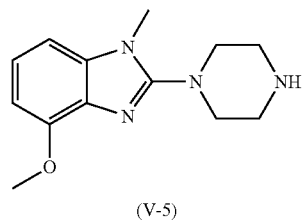

(V-5)

2 g 2-chloro-4-methoxy-1-methyl-1H-benzimidazole and 4.4 g piperazine are suspended in 20 ml n-butanol and stirred for 5 hours at reflux temperature. The reaction mixture is evaporated to dryness and the product is purified by chromatography (silica gel, dichloromethane/methanol 10:1). 1.6 g (V-5) are obtained in the form of a solid. M.p.=147° C.

14.8 (R)-2-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-ylamino}-3-methylbutan-1-ol (Example 1.14)

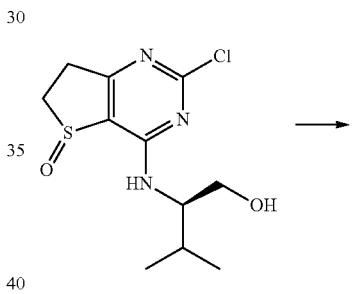

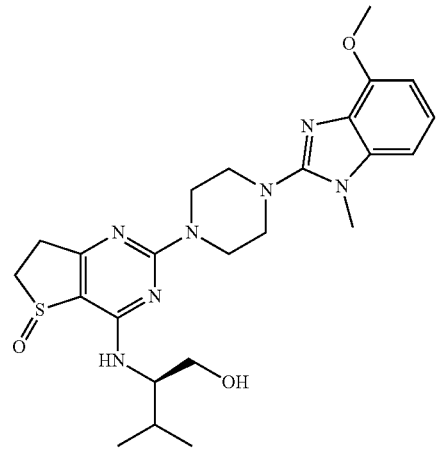

Example 1.14

Starting from (IV-2) (cf. 2.2) and (V-5), Example 1.14 is prepared and purified as the trifluoroacetate analogously to Example 1.10 (cf. 10.5). Analytical HPLC-MS (method C): RT=1.5 min.

15. SYNTHESIS OF (R)-2-{2-[4-(7-ETHYL-6,7,8,9-TETRAHYDRO-5H-PYRAZINO[2,3-d]AZEPIN-2-YL)-PIPERAZIN-1-YL]-5-OXO-6,7-DIHYDRO-5H-5λ⁴-THIENO[3,2-D]PYRIMIDIN-4-YLAMINO}-3-METHYLBUTAN-1-OL (EXAMPLE 1.15)

15.1 2-chloro-7-ethyl-6,7,8,9-tetrahydro-5H-pyrazino[2,3-d]azepine

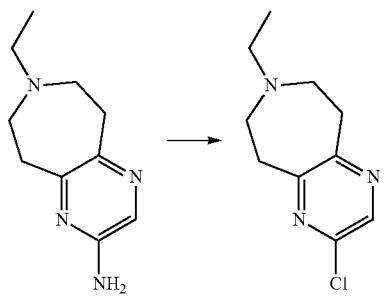

26.5 g of 7-ethyl-6,7,8,9-tetrahydro-5H-pyrazino[2,3-d]azepin-2-ylamine (U.S. Pat. No. 4,409,220) are suspended in 130 ml conc. hydrochloric acid, combined with 0.1 g copper (I)bromide and cooled to −5° C. A suspension of 11 g sodium nitrite in 14 ml of water is slowly added dropwise. The reaction mixture is stirred for 15 hours at ambient temperature and evaporated almost to dryness. The residue is slowly added to ice water and potassium carbonate. The product is extracted with dichloromethane and precipitated as the hydrochloride with an ethereal HCl solution. 14.3 g product are obtained. M.p.=258-262° C.

15.2 7-ethyl-2-piperazin-1-yl-6,7,8,9-tetrahydro-5H-pyrazino[2,3-d]azepine (V-6)

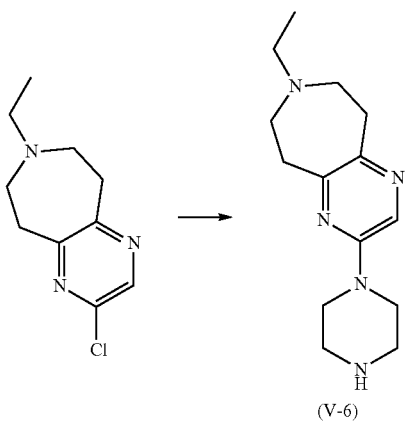

3 g 2-chloro-7-ethyl-6,7,8,9-tetrahydro-5H-pyrazino[2,3-d]azepine are combined with 23.3 g piperazine and the mixture is heated to 145° C. for 5 hours. Excess piperazine is distilled off and the residue is treated with dichloromethane and methanol. Any product precipitated is suction filtered and purified by chromatography (Alox, dioxane/toluene/methanol/NH₄OH 50/20/20/2). 1.95 g product are obtained.

15.3 (R)-2-{2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-ylamino}-3-methylbutan-1-ol (Example 1.15)

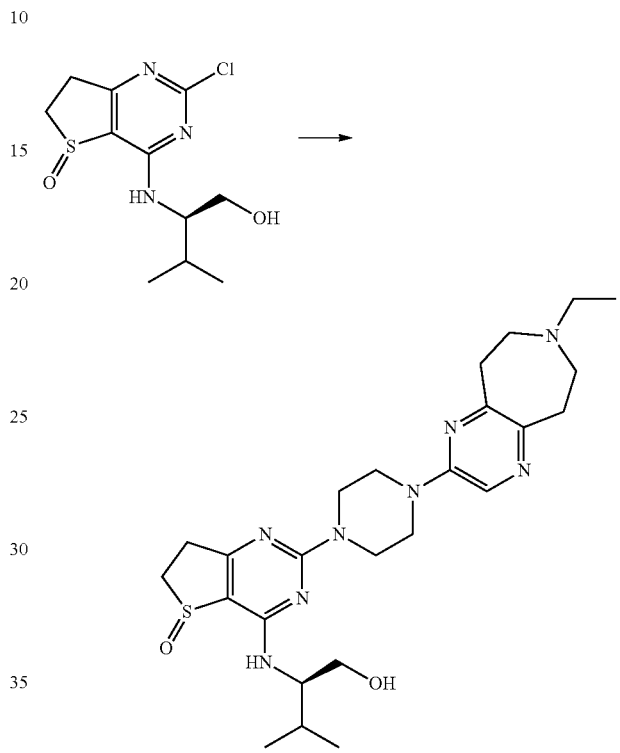

Example 1.15

Starting from (IV-2) (cf. 2.2) and (V-6) Example 1.15 is prepared and purified as the trifluoroacetate analogously to Example 1.10 (cf. 10.5). Analytical HPLC-MS (method C): RT=1.38 min.

16. SYNTHESIS OF (R)-3-METHYL-2-[5-OXO-2-(4-PYRIMIDIN-4-YL-PIPERAZIN-1-YL)-6,7-DIHYDRO-5H-5λ⁴-THIENO[3,2-D]PYRIMIDIN-4-YLAMINO]-BUTAN-1-OL (EXAMPLE 1.16)

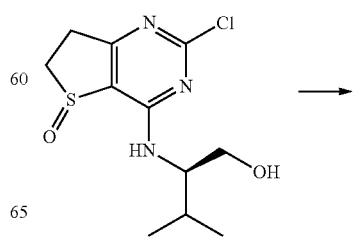

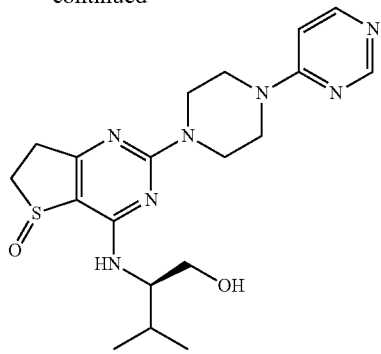

Example 1.16

Starting from (IV-2) (cf. 2.2) and 4-piperazin-1-yl-pyrimidine (*J. Org. Chem.* 1953, 1484) Example 1.16 is prepared and purified as the trifluoroacetate analogously to Example 1.10 (cf. 10.5). Analytical HPLC-MS (method C): RT=1.31 min.

17. SYNTHESIS OF 4-{4-[4-((R)-1-HYDROXYMETHYL-2-METHYLPROPYLAMINO)-5-OXO-6,7-DIHYDRO-5H-5$\lambda^4$-THIENO[3,2-D]PYRIMIDIN$^2$-YL]-PIPERAZIN-1-YL}-PYRIDIN-2-OL (EXAMPLE 1.17)

17.1 4-(1-oxypyridin-4-yl)-piperazin-1-BOC:

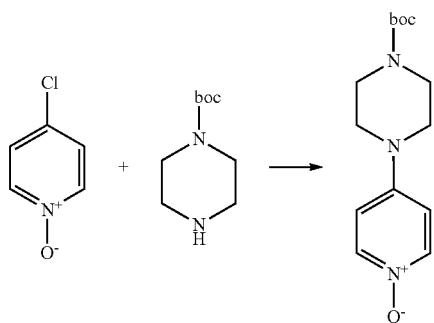

3 g 4-chloropyridine-N-oxide and 13.2 g piperazine-1-BOC are heated to 90° C. for 4 hours. The product is purified by chromatography (silica gel, dichloromethane/methanol/ammonia 90/10/1). 2.9 g product are obtained in the form of a solid.

17.2 4-(2-hydroxypyridin-4-yl)-piperazine-1-BOC

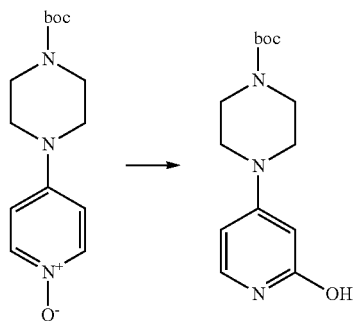

1.75 g 4-(1-oxypyridin-4-yl)-piperazin-1-BOC are suspended in 15 ml acetic anhydride and heated to 150° C. for 24 h. The reaction mixture is evaporated to dryness and the product is purified by chromatography (silica gel, ethyl acetate/methanol/ammonia 95/5/0.5). 0.51 g product are obtained in the form of a solid 17.3 4-piperazin-1-yl-pyridin-2-ol (V-7)

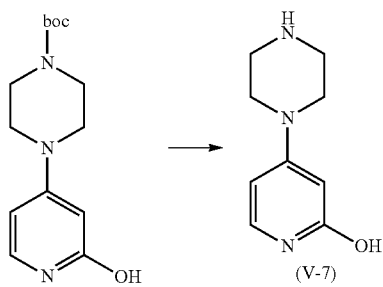

0.51 g 4-(2-hydroxypyridin-4-yl)-piperazine-1-BOC and 2 ml trifluoroacetic acid are suspended in 15 ml dichloromethane and stirred for 2 hours at ambient temperature. The reaction mixture is evaporated to dryness. 1 g (V-7) are obtained as an oil. $^1$H NMR (400 MHz, DMSO): 7.30 (1H, d); 5.99 (1H, dd); 5.34 (1H, d).

17.4 4-{4-[4-((R)-1-hydroxymethyl-2-methylpropylamino)-5-oxo-6,7-dihydro-5H-5$\lambda^4$-thieno[3,2-d]pyrimidin-2-yl]-piperazin-1-yl}-pyridin-2-ol (Example 1.17)

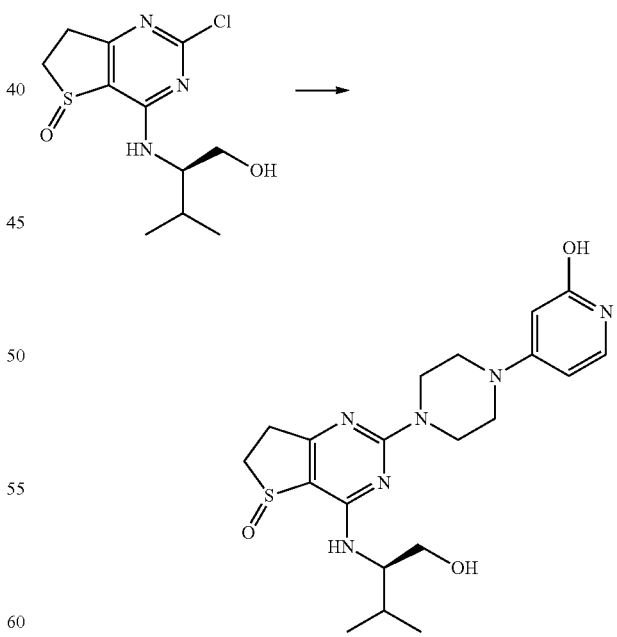

Example 1.17

Starting from (IV-2) (cf. 2.2) and (V-7) Example 1.17 is prepared and purified analogously to Example 1.10 (cf. 10.5). Analytical HPLC-MS (method C): RT=1.37 min.

18. SYNTHESIS OF (R)-3-METHYL-2-[5-OXO-2-(4-PYRIDIN-4-YL-PIPERAZIN-1-YL)-6,7-DIHYDRO-5H-5λ⁴-THIENO[3,2-D]PYRIMIDIN-4-YLAMINO]-BUTAN-1-OL TRIFLUOROACETATE (EXAMPLE 1.18)

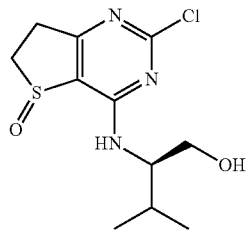

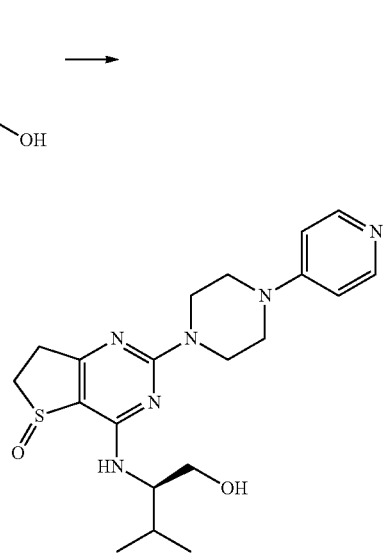

Example 1.18

Starting from (IV-2) (cf. 2.2) and 1-pyridin-4-yl-piperazine Example 1.18 is prepared and purified as the trifluoroacetate analogously to Example 1.10 (cf. 10.5). Analytical HPLC-MS (method C): RT=1.33 min.

19. SYNTHESIS OF (R)-2-{2-[4-(3-DIMETHYLAMINOPYRIDAZIN-4-YL)-PIPERAZIN-1-YL]-5-OXO-6,7-DIHYDRO-5H-5λ⁴-THIENO[3,2-D]PYRIMIDIN-4-YLAMINO}-3-METHYLBUTAN-1-OL (EXAMPLE 1.19)

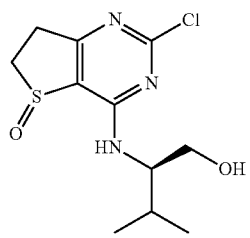

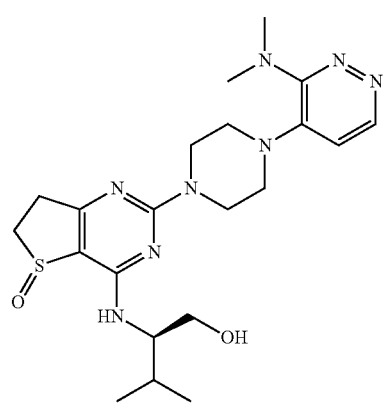

Example 1.19

Starting from (IV-2) (cf. 2.2) and (V-1) (cf. 10.4) Example 1.19 is prepared and purified as the trifluoroacetate analogously to Example 1.10 (cf. 10.5). Analytical HPLC-MS (method C): RT=1.37 min.

20. SYNTHESIS OF 6-CHLORO-4-{4-[4-((R)-1-HYDROXYMETHYL-2-METHYL-PROPYLAMINO)-5-OXO-6,7-DIHYDRO-5H-5λ⁴-THIENO[3,2-D]PYRIMIDIN-2-YL]-PIPERAZIN-1-YL}-PYRIDAZIN-3-OL (EXAMPLE 1.20)

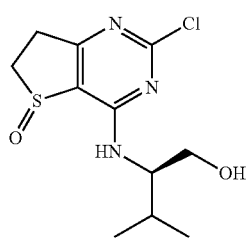

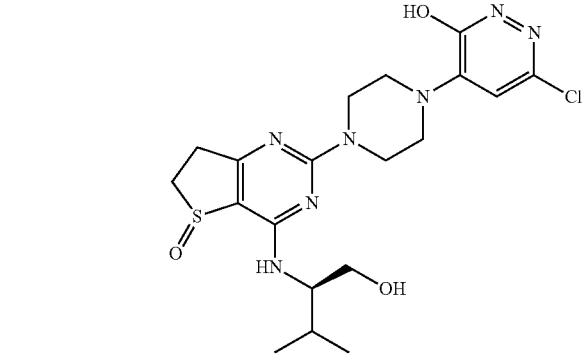

Example 1.20

Starting from (IV-2) (cf. 2.2) and (V-2) (cf. 11.2) Example 1.20 is prepared and purified analogously to Example 1.10 (cf. 10.5). Analytical HPLC-MS (method C): RT=1.55 min.

21. SYNTHESIS OF (R)-2-(2-{4-[6-(2-ETHOXYETHOXY)-PYRIDAZIN-3-YL]-PIPERAZIN-1-YL}-5-OXO-6,7-DIHYDRO-5H-5λ⁴-THIENO[3,2-D]PYRIMIDIN-4-YLAMINO)-3-METHYLBUTAN-1-OL (EXAMPLE 1.21)

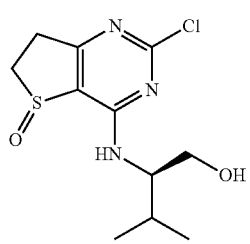

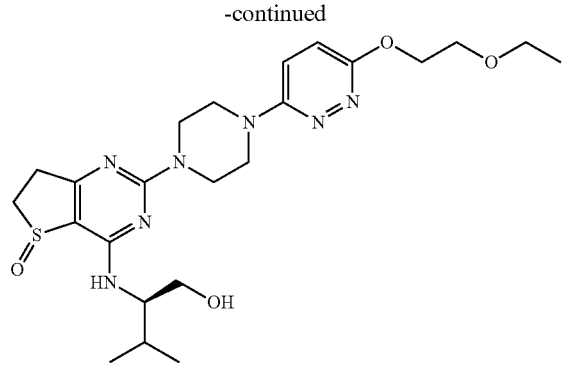

Example 1.21

Starting from (IV-2) (cf. 2.2) and (V-3) (cf. 12.1) Example 1.21 is prepared and purified as the trifluoroacetate analogously to Example 1.10 (cf. 10.5). Analytical HPLC-MS (method C): RT=1.45 min.

22. SYNTHESIS OF (R)-3-METHYL-2-[5-OXO-2-(4-PYRIDAZIN-4-YL-PIPERAZIN-1-YL)-6,7-DI-HYDRO-5H-5λ⁴-THIENO[3,2-D]PYRIMIDIN-4-YLAMINO]-BUTAN-1-OL (EXAMPLE 1.22)

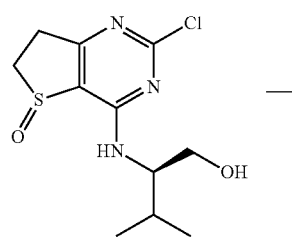

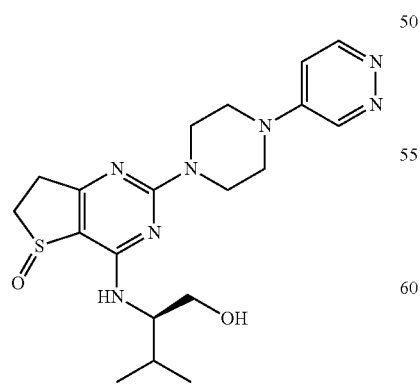

Example 1.22

Starting from (IV-2) (cf. 2.2) and (V-4) (cf. 13.1) Example 1.22 is prepared and purified as the trifluoroacetate analogously to Example 1.10 (cf. 10.5). Analytical HPLC-MS (method C): RT=0.56 min.

23. SYNTHESIS OF {1-[5-OXO-2-(4-PYRIMIDIN-4-YL-PIPERAZIN-1-YL)-6,7-DI-HYDRO-5H-5λ⁴-THIENO[3,2-D]PYRIMIDIN-4-YLAMINO]-CY-CLOPROPYL}-METHANOL TRIFLUOROACETATE (EXAMPLE 1.23)

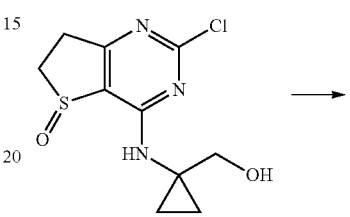

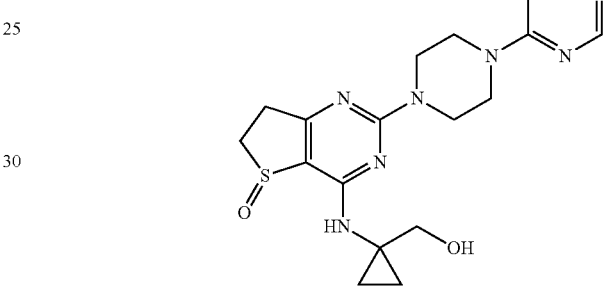

Example 1.23

Starting from (IV-4) (cf. 8.4) and 4-piperazin-1-yl-pyrimidine (*J. Org. Chem.* 1953, 1484) Example 1.23 is prepared and purified as the trifluoroacetate analogously to Example 1.10 (cf. 10.5). Analytical HPLC-MS (method C): RT=1.29 min.

24 SYNTHESIS OF {1-[5-OXO-2-(4-PYRIDIN-4-YL-PIPERAZIN-1-YL)-6,7-DIHYDRO-5H-5λ⁴-THIENO[3,2-D]PYRIMIDIN-4-YLAMINO]-CY-CLOPROPYL}-METHANOL TRIFLUOROACETATE (EXAMPLE 1.24)

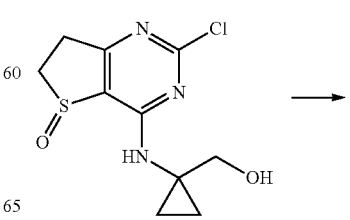

-continued

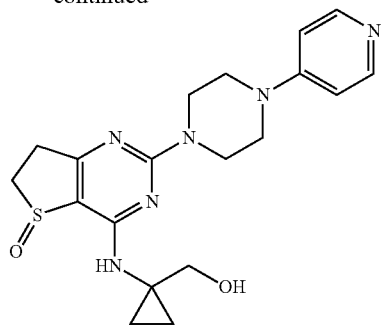

Example 1.24

Starting from (IV-4) (cf. 8.4) and 1-pyridin-4-yl-piperazine Example 1.24 is prepared and purified as the trifluoroacetate analogously to Example 1.10 (cf. 10.5). Analytical HPLC-MS (method C): RT=1.29 min.

25. SYNTHESIS OF (S)-1-METHYL-5-[5-OXO-2-(4-PYRIMIDIN-4-YL-PIPERAZIN-1-YL)-6,7-DI-HYDRO-5H-5λ⁴-THIENO[3,2-D]PYRIMIDIN-4-YLAMINO]-PIPERIDIN-2-ONE (EXAMPLE 1.25)

25.1 (S)-5-dibenzylaminopiperidin-2-one:

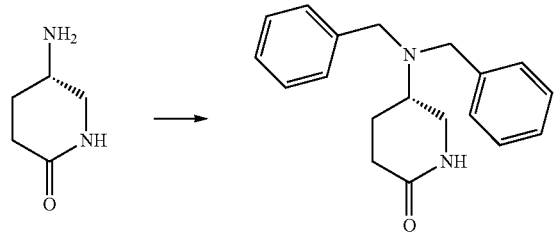 [SMILES: N[C@H]1CCC(=O)NC1 ; O=C1CC[C@H](N(Cc2ccccc2)Cc2ccccc2)CN1]

0.600 g 4-(S)-amino-delta-valerolactam hydrochloride, 0.970 ml benzylbromide and 1.5 g sodium hydrogen carbonate are suspended in 30 ml of ethanol. The reaction mixture is then stirred for 8 hours at 80° C. and then evaporated to dryness. The residue is suspended in water and the product is extracted with dichloromethane and purified by chromatography (silica gel, dichloromethane/methanol 100/0 to 95/5). 0.500 g of the product are obtained as an oil. Analytical HPLC-MS (method A): RT=1.01 min.

25.2 (S)-5-dibenzylamino-1-methylpiperidin-2-one:

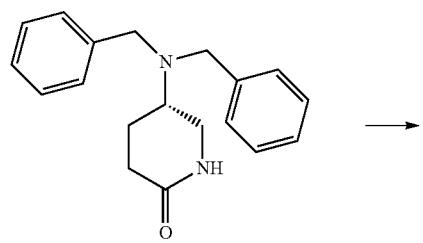

-continued

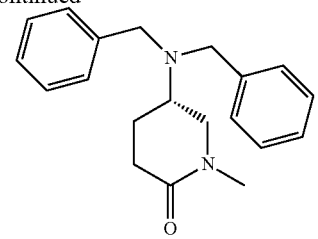

0.500 g (S)-5-dibenzylaminopiperidin-2-one are suspended in 15 ml of tetrahydrofuran. While cooling with the ice bath 0.175 g potassium-tert-butoxide are added. The reaction mixture is then stirred for 30 minutes at ambient temperature. While cooling with the ice bath 0.095 ml methyl iodide are added. The reaction mixture is then stirred for 48 hours at ambient temperature and then combined with a saturated NaCl solution. The product is extracted with ethyl acetate. 0.450 g of the product are obtained as an oil. Analytical HPLC-MS (method A): RT=1.07 min.

25.3 (S)-5-amino-1-methylpiperidin-2-one:

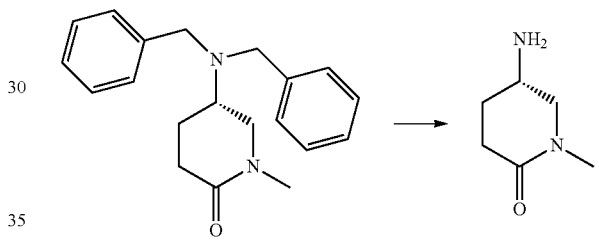

0.450 g (S)-5-dibenzylamino-1-methylpiperidin-2-one are suspended in 25 ml of methanol and hydrogenated with 0.150 g Pd/C 10% at a pressure of 3 bar and a temperature of 60° C. After 16 hours the catalyst is eliminated by suction filtering and the filtrate is evaporated to dryness. 0.190 g of the product are obtained as an oil. $^1$H NMR (400 MHz, DMSO): 2.76 (3H, s).

25.4 (S)-5-(2-chloro-6,7-dihydrothieno[3,2-d]pyrimidin-4-ylamino)-1-methylpiperidin-2-one (III-5)

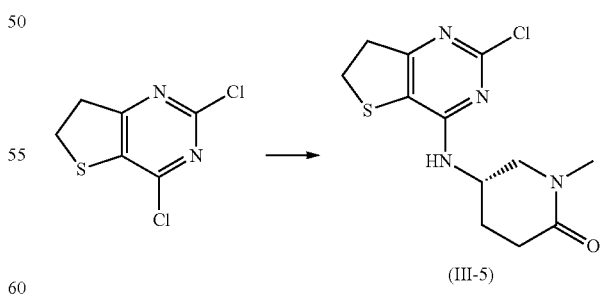

(III-5)

0.27 g (II) are placed in 3 ml dioxane, then 0.45 ml diisopropylethylamine and 0.25 g (S)-5-amino-1-methylpiperidin-2-one are added. The reaction mixture is heated to 130° C. until there is no further reaction, then cooled and evaporated down. The product is extracted with dichloromethane and purified by chromatography (preparative HPLC, method B).

0.26 g (III-5) are obtained in the form of a solid. Analytical HPLC-MS (method A): RT=1.06 min.

25.5 (S)-5-(2-chloro-5-oxo-6,7-dihydro-5H-5λ$^4$-thieno[3,2-d]pyrimidin-4-ylamino)-1-methylpiperidin-2-one (IV-5)

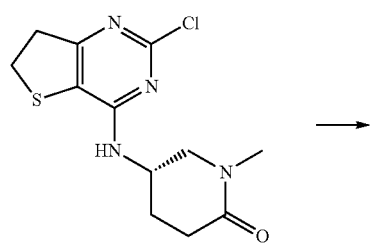

0.04 g S-(−)-1,1'-bi-2-naphthol are placed in 5 ml chloroform under argon, then 0.02 ml titanium(IV)-isopropoxide and 0.025 ml of water are added. The reaction mixture is stirred for 1 hour at ambient temperature. Then a suspension of 0.2 g (III-5) in 4 ml dichloromethane is added. The reaction mixture is cooled to −5° C. and after 20 minutes 0.12 ml tert-butylhydroperoxide 5-6 M in decane are added dropwise. The reaction mixture is stirred further at −5° C. until there is no further reaction and made basic with NH$_4$OH. The product is extracted with dichloromethane and purified by chromatography (silica gel, ethyl acetate/methanol 100/0 to 60/40). 0.09 g (IV-5) are obtained in the form of a solid. Analytical HPLC-MS (method A): RT=0.83 min.

25.6 (S)-1-methyl-5-[5-oxo-2-(4-pyrimidin-4-yl-piperazin-1-yl)-6,7-dihydro-5H-5λ$^4$-thieno[3,2-d]pyrimidin-4-ylamino]-piperidin-2-one (Example 1.25)

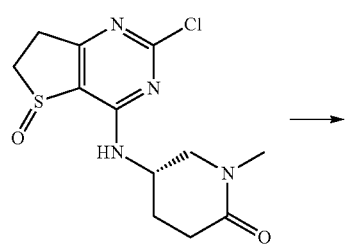

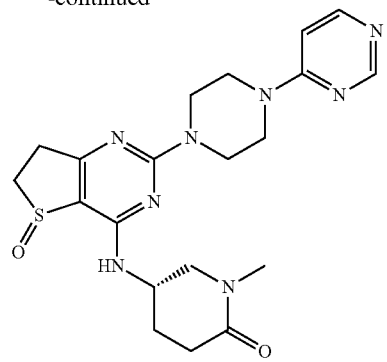

Example 1.25

Starting from (IV-5) and 4-piperazin-1-yl-pyrimidine (*J. Org. Chem.* 1953, 1484) Example 1.25 is prepared and purified as the trifluoroacetate analogously to Example 1.10 (cf. 10.5). Analytical HPLC-MS (method C): RT=1.28 min.

26. SYNTHESIS OF {2-[4-(5-FLUORO-1-METHYL-1H-BENZIMIDAZOL-2-YL)-PIPERAZIN-1-YL]-5-OXO-6,7-DIHYDRO-5H-5λ$^4$-THIENO[3,2-D]PYRIMIDIN-4-YL}-(TETRAHYDROPYRAN-4-YL)-AMINE (EXAMPLE 1.26)

26.1 (4-fluoro-2-nitrophenyl)-methylamine

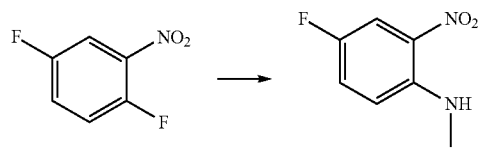

7.3 g 1,4-difluoro-2-nitrobenzene are slowly added to a 30 ml 40% aqueous methylamine solution while cooling with ice and the reaction mixture is stirred for 1 hour at ambient temperature. The precipitated product is suction filtered and recrystallised aus water and ethanol umkristallisiert. 6.3 g product are obtained in the form of a solid. M.p.=74-76° C.

26.2 4-fluoro-N$^1$-methylbenzol-1,2-diamine

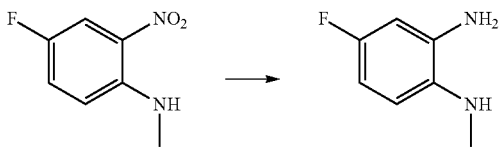

6.2 g (4-fluoro-2-nitrophenyl)-methylamine are suspended in 200 ml of ethyl acetate and hydrogenated with 1 g Raney-Nickel at a pressure of 5 bar and ambient temperature. After 4.5 hours the catalyst is removed by suction filtering and the filtrate is evaporated to dryness. 3.9 g product are obtained as an oil.

26.3
5-fluoro-1-methyl-1,3-dihydrobenzimidazol-2-one

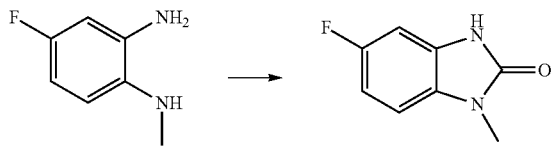

6 g 4-fluoro-N-1-methylbenzol-1,2-diamine are suspended in 200 ml of tetrahydrofuran and 7.1 g N,N'-carbonyldiimidazole are added. The reaction mixture is stirred for 48 hours at ambient temperature and the precipitated product is suction filtered and recrystallised from dioxane. 3.9 g product are obtained in the form of a solid. M.p.=207° C.

26.4 2-chloro-5-fluoro-1-methyl-1H-benzimidazole

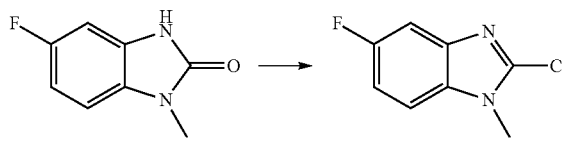

3.9 g 5-fluoro-1-methyl-1,3-dihydro-benzimidazol-2-one are suspended in 80 ml phosphorus oxychloride and the reaction mixture is stirred for 2 hours at reflux temperature. 50 ml diethylaniline are added. The reaction mixture is stirred for a further 10 minutes at reflux temperature and ice water is slowly added thereto. The product is extracted with dichloromethane and purified by chromatography (silica gel, cyclohexane, methylene chloride/acetone 20/1). 1.4 g product are obtained in the form of a solid. M.p.=138-141° C.

26.5 5-fluoro-1-methyl-2-piperazin-1-yl-1H-benzimidazole (V-8)

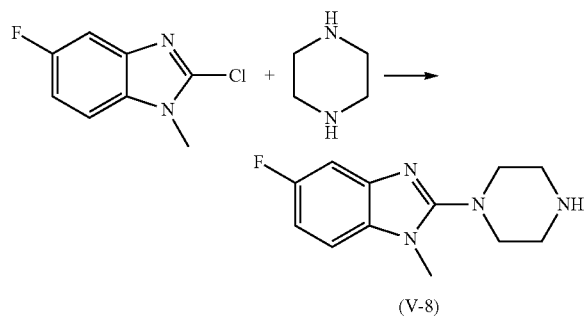

0.7 g 2-chloro-5-fluoro-1-methyl-1H-benzimidazole and 1.3 g piperazine are suspended in 10 ml n-butanol and stirred for 48 hours at ambient temperature. The reaction mixture is evaporated to dryness and the product is purified by chromatography (aluminium oxide, methylene chloride/methanol 10/1). 0.73 g (V-8) are obtained in the form of a solid. $^1$H NMR (400 MHz, DMSO): 6.9 (1H, t); 3.6 (3H, s).

26.6 {2-[4-(5-fluoro-1-methyl-1H-benzoimidazol-2-yl)-piperazin-1-yl]-5-oxo-6,7-dihydro-5H-5$\lambda^4$-thieno[3,2-d]pyrimidin-4-yl}-(tetrahydropyran-4-yl)-amine (Example 1.26)

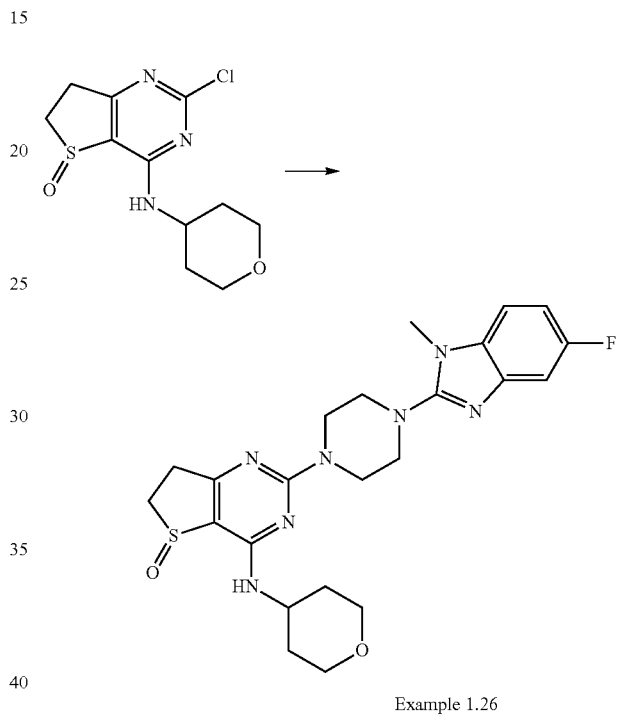

Example 1.26

Starting from (IV-3) (cf. 4.2) and (V-8) Example 1.26 is prepared and purified analogously to Example 1.10 (cf. 10.5). Analytical HPLC-MS (method C): RT=1.48 min.

27. SYNTHESIS OF [5-OXO-2-(4-PYRIDIN-4-YL-PIPERAZIN-1-YL)-6,7-DIHYDRO-5H-5$\lambda^4$-THIENO[3,2-D]PYRIMIDIN-4-YL]-(TETRAHYDROPYRAN-4-YL)-AMINE (EXAMPLE 1.27)

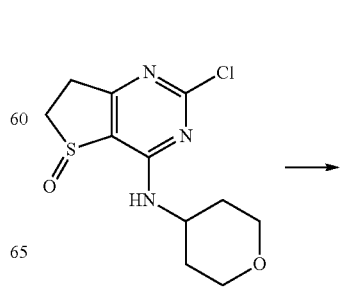

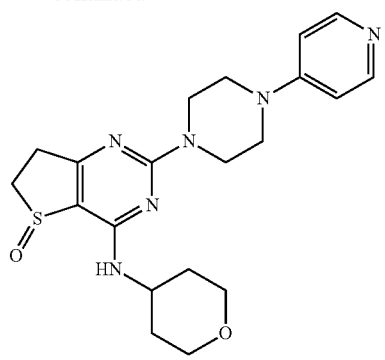

Example 1.27

Starting from (IV-3) (cf. 4.2) and 1-pyridin-4-yl-piperazine Example 1.27 is prepared and purified as the trifluoroacetate analogously to Example 15 (cf. 10.5). Analytical HPLC-MS (method C): RT=1.32 min.

28. SYNTHESIS OF (3-FLUOROPHENYL)-{2-[4-(4-METHOXY-1-METHYL-1H-BENZ-IMIDAZOL-2-YL)-PIPERAZIN-1-YL]-5-OXO-6,7-DIHYDRO-5H-5λ⁴-THIENO[3,2-D]PYRIMIDIN-4-YL}-AMINE (EXAMPLE 1.28)

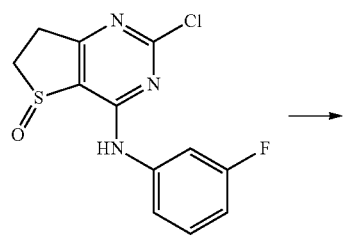

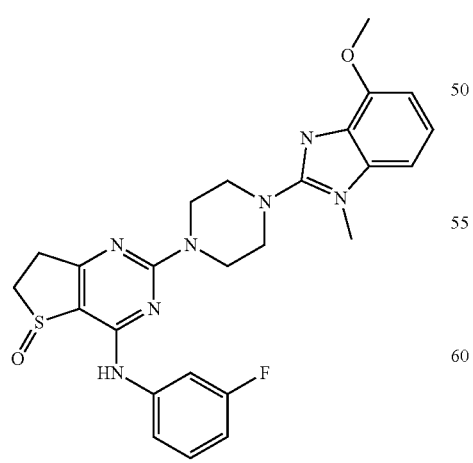

Example 1.28

Starting from (IV-1) (cf. 1.2) and (V-5) (cf. 14.7) Example 1.28 is prepared and purified as the trifluoroacetate analogously to Example 1.10 (cf. 10.5). Analytical HPLC-MS (method C): RT=1.73 min.

29. SYNTHESIS OF {2-[4-(7-ETHYL-6,7,8,9-TETRAHYDRO-5H-PYRAZINO[2,3-d]AZEPIN-2-YL)-PIPERAZIN-1-YL]-5-OXO-6,7-DIHYDRO-5H-5λ⁴-THIENO[3,2-D]PYRIMIDIN-4-YL}-(3-FLUOROPHENYL)-AMINE (EXAMPLE 1.29)

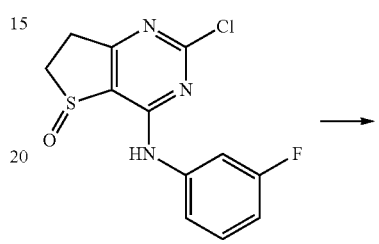

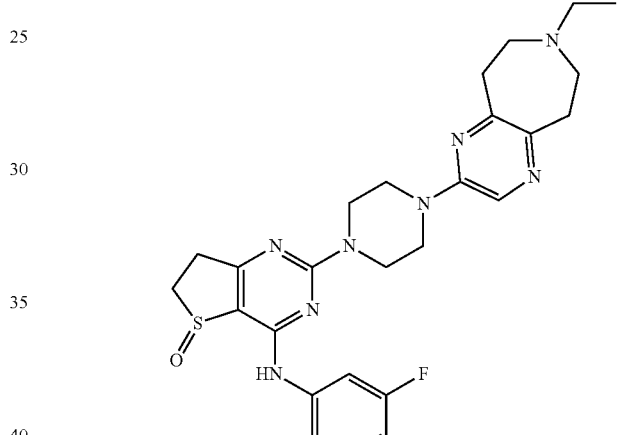

Example 1.29

Starting from (IV-1) (cf. 1.2) and (V-6) (cf. 15.2) Example 1.29 is prepared and purified as the trifluoroacetate analogously to Example 1.10 (cf. 10.5). Analytical HPLC-MS (method C): RT=1.6 min.

30. SYNTHESIS OF (3-FLUOROPHENYL)-[5-OXO-2-(4-PYRIMIDIN-4-YL-PIPERAZIN-1-YL)-6,7-DIHYDRO-5H-5λ⁴-THIENO[3,2-D]PYRIMIDIN-4-YL]-AMINE (EXAMPLE 1.30)

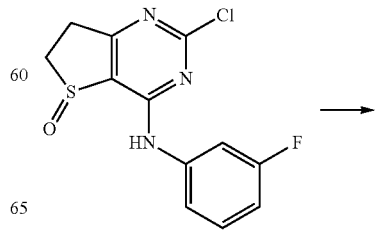

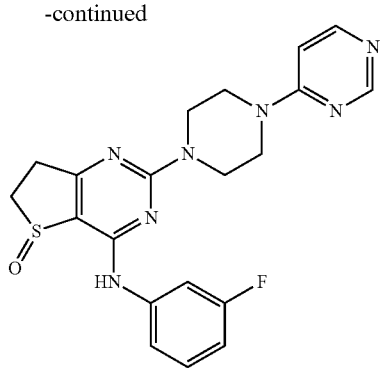

Example 1.30

Starting from (IV-1) (cf. 1.2) and 4-piperazin-1-yl-pyrimidine (*J. Org. Chem.* 1953, 1484) Example 1.30 is prepared and purified as the trifluoroacetate analogously to Example 1.10 (cf. 10.5). Analytical HPLC-MS (method C): RT=1.56 min.

31. SYNTHESIS OF 4-{4-[4-(3-FLUOROPHENY-LAMINO)-5-OXO-6,7-DIHYDRO-5H-5λ⁴-THIENO[3,2-D]PYRIMIDIN-2-YL]-PIPERAZIN-1-YL}-PYRIDIN-2-OL (EXAMPLE 1.31)

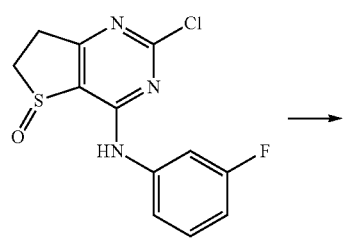

→

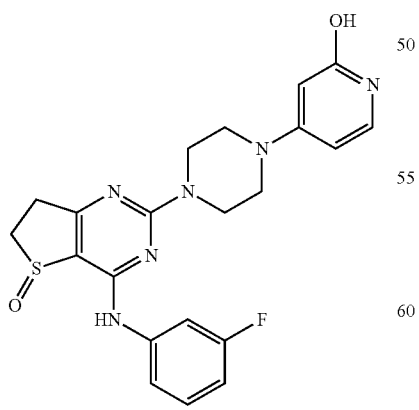

Example 1.31

Starting from (IV-1) (cf. 1.2) and (V-7) (cf. 17.3) Example 1.31 is prepared and purified analogously to Example 1.10 (cf. 10.5). Analytical HPLC-MS (method C): RT=1.61 min.

32. SYNTHESIS OF (3-FLUOROPHENYL)-[5-OXO-2-(4-PYRIDIN-4-YL-PIPERAZIN-1-YL)-6,7-DIHYDRO-5H-5λ⁴-THIENO[3,2-D]PYRIMIDIN-4-YL]-AMINE (EXAMPLE 1.32)

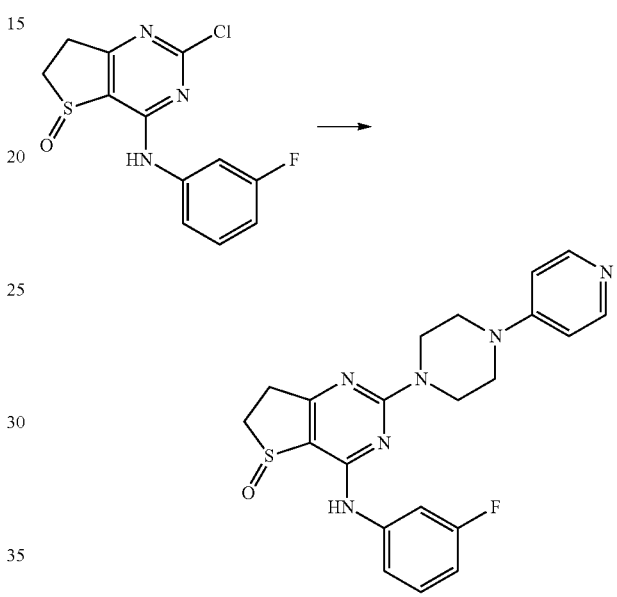

Example 1.32

Starting from (IV-1) (cf. 1.2) and 1-pyridin-4-yl-piperazine Example 1.32 is prepared and purified analogously to Example 1.10 (cf. 10.5). Analytical HPLC-MS (method C): RT=1.56 min.

33. SYNTHESIS OF (3-FLUOROPHENYL)-(2-{4-[4-(4-FLUOROPHENYL)-THIAZOL-2-YL]-PIPERAZIN-1-YL}-5-OXO-6,7-DIHYDRO-5H-5λ⁴-THIENO[3,2-D]PYRIMIDIN-4-YL)-AMINE (EXAMPLE 1.33)

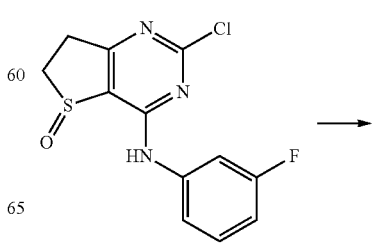

→

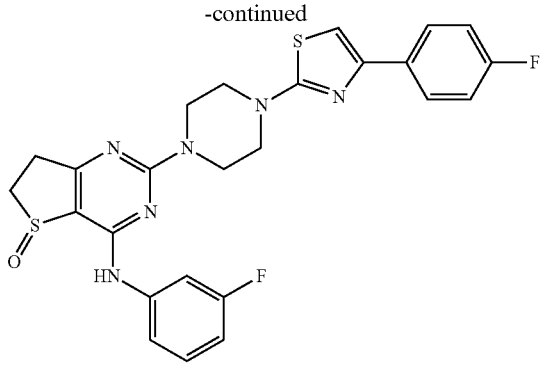

Example 1.33

Starting from (IV-1) (cf. 1.2) and 1-[4-(4-fluorophenyl)-thiazol-2-yl]-piperazine Example 1.33 is prepared and purified analogously to Example 1.10 (cf. 10.5). Analytical HPLC-MS (method C): RT=2.42 min.

34. SYNTHESIS OF [2-(4-BENZO[d]ISOXAZOL-3-YL-PIPERAZIN-1-YL)-5-OXO-6,7-DIHYDRO-5H-5λ⁴-THIENO[3,2-D]PYRIMIDIN-4-YL]-(3-FLUOROPHENYL)-AMINE (EXAMPLE 1.34)

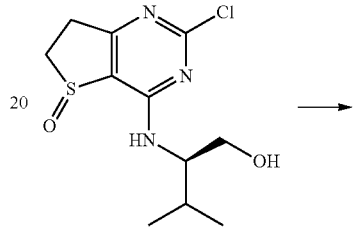

→

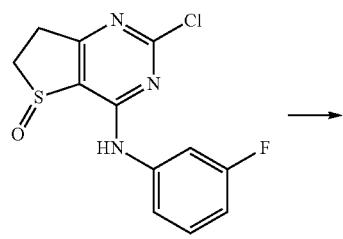

Example 1.34

Starting from (IV-1) (cf. 1.2) and 3-piperazin-1-yl-benzo[d]isoxazole Example 1.34 is prepared and purified analogously to Example 1.10 (cf. 10.5). Analytical HPLC-MS (method C): RT=2.19 min.

35. SYNTHESIS OF (R)-2-(2-{4-[4-(4-FLUOROPHENYL)-THIAZOL-2-YL]-PIPERAZIN-1-YL}-5-OXO-6,7-DIHYDRO-5H-5λ⁴-THIENO[3,2-D]PYRIMIDIN-4-YLAMINO)-3-METHYLBUTAN-1-OL (EXAMPLE 1.35)

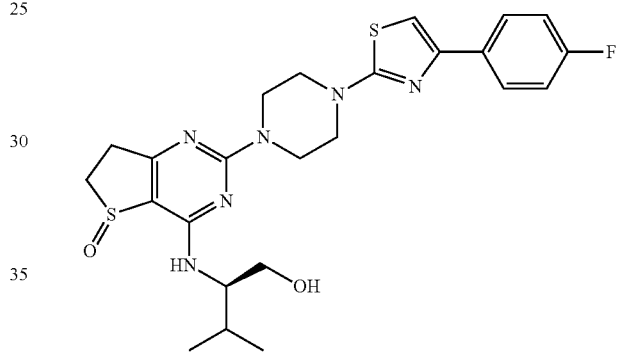

→

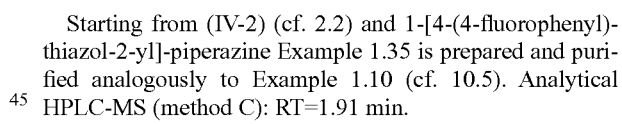

Example 1.35

Starting from (IV-2) (cf. 2.2) and 1-[4-(4-fluorophenyl)-thiazol-2-yl]-piperazine Example 1.35 is prepared and purified analogously to Example 1.10 (cf. 10.5). Analytical HPLC-MS (method C): RT=1.91 min.

36. SYNTHESIS OF (R)-2-[2-(4-BENZO[d]ISOXAZOL-3-YL-PIPERAZIN-1-YL)-5-OXO-6,7-DIHYDRO-5H-5λ⁴-THIENO[3,2-D]PYRIMIDIN-4-YLAMINO]-3-METHYLBUTAN-1-OL (EXAMPLE 1.36)

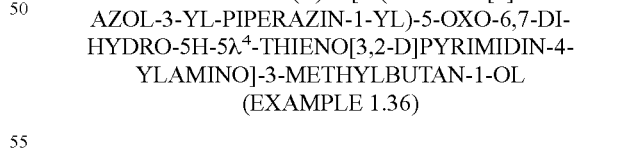

→

-continued

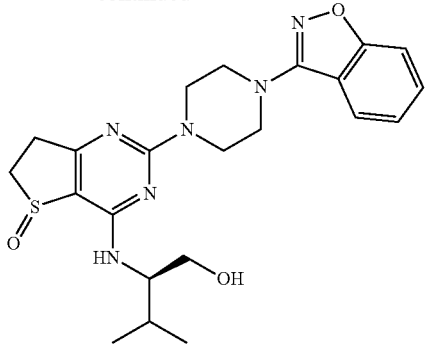

Example 1.36

Starting from (IV-2) (cf. 2.2) and 3-piperazin-1-yl-benzo[d]isoxazol Example 1.36 is prepared and purified analogously to Example 1.10 (cf. 10.5). Analytical HPLC-MS (method C): RT=1.76 min.

Methods of Chromatography

The Example compounds prepared according to the synthesis schemes shown above were characterised by the following chromatographic methods, which—if used—are individually specified in Table A.

Analytical HPLC-MS, method A

Waters ZMD mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% TFA
B: acetonitrile with 0.10% TFA

| time in min | % A | % B | flow rate in ml/min |
|---|---|---|---|
| 0.00 | 95 | 5 | 2.50 |
| 0.20 | 95 | 5 | 2.50 |
| 1.50 | 2 | 98 | 2.50 |
| 1.70 | 2 | 98 | 2.50 |
| 1.90 | 95 | 5 | 2.50 |
| 2.20 | 95 | 5 | 2.50 |

The stationary phase used is a Merck Chromolith™ Flash RP-18e column, 4.6 mm×25 mm (column temperature: constant at 25° C.).

Analytical HPLC-MS, Method B

Waters ZMD mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% NH$_3$
B: acetonitrile with 0.10% NH$_3$

| time in min | % A | % B | flow rate in ml/min |
|---|---|---|---|
| 0.00 | 95 | 5 | 3.00 |
| 0.20 | 95 | 5 | 3.00 |
| 1.50 | 2 | 98 | 3.00 |
| 1.90 | 2 | 98 | 3.00 |
| 2.00 | 2 | 98 | 3.00 |

The stationary phase used is Waters, X-Bridge, C18, 3.5 nm, 4.6×20 mm, ambient temperature Analytical HPLC-MS, Method C Waters ZQ2000 mass spectrometer (positive ionisation (ESI+)), HP1100 HPLC (DAD, wavelength range: 210 to 500 nm), and Gilson 215 Autosampler.
A: water with 0.10% TFA
B: acetonitrile with 0.10% TFA

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

The stationary phase used is a Sunfire C18 column, 4.6×50 mm, 3.5 μm, column temperature 40° C.

Analytical HPLC, Method A

Agilent 1100, diode array detection is carried out in the wavelength range 210-380 nm.
A: water with 0.10% TFA
B: acetonitrile with 0.13% TFA

| time in min | % A | % B | flow rate in ml/min |
|---|---|---|---|
| 0.00 | 95 | 5 | 1.50 |
| 0.60 | 95 | 5 | 1.50 |
| 3.40 | 2 | 98 | 1.50 |
| 3.90 | 2 | 98 | 1.50 |
| 4.20 | 95 | 5 | 1.50 |
| 4.90 | 95 | 5 | 1.50 |

The stationary phase used is a Varian Microsorb column, RP C18, 3 μm, 100 A, ambient temperature.

Preparative HPLC-MS, Method A

Waters ZQ2000 mass spectrometer (positive ionisation (ESI+)), HP1100 HPLC (DAD, wavelength range: 210-500 nm), and Gilson 215 Autosampler.
A: water with 0.10% TFA
B: acetonitrile

| time in min | % A | % B | flow rate in ml/min |
|---|---|---|---|
| 0.00 | 90 | 10 | 50 |
| 1.50 | 90 | 10 | 50 |
| 8.00 | 40 | 60 | 50 |
| 10.00 | 40 | 60 | 50 |
| 11.00 | 90 | 10 | 50 |

The stationary phase used is a Sunfire C18 column, 30×100 mm, 5 μm, ambient temperature.

Preparative HPLC, Method A

Gilson HPLC with Gilson UV-VIS-155 Detektor, 231 XL sampling injector.
The wavelength given is the substance-specific UV maximum.
A: water with 0.1% ammonia 35%
B: acetonitrile

| time in min | % A | % B | flow rate in ml/min |
|---|---|---|---|
| 0.00 | 95 | 5 | 180 |
| 1.40 | 95 | 5 | 180 |
| 17.00 | 2 | 98 | 180 |
| 18.50 | 2 | 98 | 180 |
| 18.70 | 95 | 5 | 180 |
| 20.-50 | 95 | 5 | 180 |

The stationary phase used is a Pursuit XRS RP 18 column, 10 μm, 50×150 mm, ambient temperature.

Preparative HPLC, Method B

Gilson HPLC with Gilson UV-VIS-155 detector, 231 XL sampling injector.

The wavelength given is the substance-specific UV maximum.

A: water with 0.13% TFA
B: acetonitrile with 0.1% TFA

| time in min | % A | % B | flow rate in ml/min |
|---|---|---|---|
| 0.00 | 95 | 5 | 165 |
| 1.30 | 95 | 5 | 165 |
| 8.90 | 2 | 98 | 165 |
| 10.00 | 2 | 98 | 165 |
| 10.50 | 95 | 5 | 165 |
| 11.60 | 95 | 5 | 165 |

The stationary phase used is a Microsorb RP 18 column, 8 μm, 50×65 mm, ambient temperature Indications As has been found, the combinations according to the invention containing a compound of formula 1 and at least one NSAID are characterised by their wide range of applications in the therapeutic field. Particular mention should be made of those applications for which the combinations according to the invention are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia, and bone tumours such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of the combinations according to the invention for preparing a medicament for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

It is most preferable to use the combinations according to the invention for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the combinations according to the invention for the treatment of diseases of the peripheral or central nervous system such as depression, bipolar or manic depression, acute and chronic anxiety states, schizophrenia, Alzheimer's disease, Parkinson's disease, acute and chronic multiple sclerosis, amyotrophic lateral sclerosis (ALS) or acute and chronic pain as well as injuries to the brain caused by stroke, hypoxia or craniocerebral trauma.

An outstanding aspect of the formulations according to the invention containing a combination of a compound of formula 1 and at least one NSAID is the reduced profile of side effects compared with formulations that contain the same compound of formula 1 in the same amount in the absence of an NSAID. Side effects that frequently occur when taking a PDE4 inhibitor preferentially include, inter alia, diarrhoea, nausea and vomiting. In the rat model further side effects were observed after the administration of PDE4 inhibitor, such as for example weight loss, leukocytosis and neutrophilia, as well as diarrhoea.

By a reduced profile of side effects is meant, within the scope of the invention, in particular being able to administer a therapeutically effective dose of a PDE4 inhibitor in a pharmaceutical composition according to the invention without inducing to any appreciable extent in the patient the or at least one of the side effects commonly observed when PDE4 inhibitors are administered. It is particularly preferable to administer a therapeutically effective amount of a PDE4 inhibitor in the composition according to the invention at every stage of the course of the disease without triggering the typical PDE4 inhibitor-mediated side effects of diarrhoea, weight loss, leukocytosis or neutrophilia. In a particular aspect the present invention relates to the administration of a therapeutically effective amount of the pharmaceutical composition according to the invention at every stage of the course of the disease without triggering the typical PDE4 inhibitor-mediated side effect of diarrhoea to any appreciable degree.

Experiments on the rat model described hereinafter show that the pharmaceutical compositions according to the invention containing a PDE4 inhibitor and at least one NSAID substantially reduce or even totally prevent many of the side effects which occur when the corresponding PDE4 inhibitor is administered on its own.

EXPERIMENTAL METHOD

The results of the following experiments are summarized in the Figures:

FIG. 1B shows the measured white blood cells (left side) and the measured neutrophils (right side) for the different groups (control group, Roflumilast group, Roflumilast+Diclofenac group and Diclofenac group). Statistics: One-way analysis of variance; ns=not significant; ***=p<0.001.

FIG. 2B shows the measured white blood cells (left side) and the measured neutrophils (right side) for the different groups (control group, Roflumilast group, Roflumilast+SC-560 group, Roflumilast+Lumiracoxib group, SC-560 group and Lumiracoxib group). Statistics: One-way analysis of variance; ns=not significant; *=p<0.05; ***=p<0.001.

EXPERIMENT 1

Diclofenac Provides Protection Against Roflumilast-Mediated Effects Such as Weight Loss, Leukocytosis, and Neutrophilia Six male Wistar rats in each group were treated for four days with the following substances (all substances are given p.o.=orally):
Group 1 ("control group"): Six male Wistar rats were given a daily dose of 0.5% Natrosol (placebo) at the times 0800, 1300 and 1700 hours.
Group 2 ("roflumilast group"): Six male Wistar rats were given a daily dose of 0.5% Natrosol (placebo) at 0800 and 1700 hours and 10 mg/kg roflumilast (PDE4 inhibitor) at 1300 hours.
Group 3 ("roflumilast+diclofenac group"): Six male Wistar rats were given a daily dose of 1 mg/kg diclofenac (NSAID) at the times 0800 and 1700 hours and 10 mg/kg roflumilast (PDE4 inhibitor) at 1300 hours.
Group 4 ("diclofenac group"): Six male Wistar rats were given a daily dose of 1 mg/kg diclofenac (NSAID) at the times 0800 and 1700 hours and 0.5% Natrosol (placebo) at 1300 hours.

For pharmacokinetic analysis (determining the plasma levels of the substances) on day 4 one rate from each group was used; these rats were no longer available for other parameters under investigation. The same applied to one rat from the roflumilast group which died between day 4 and day 5 of the experiment.

Figure 1A:
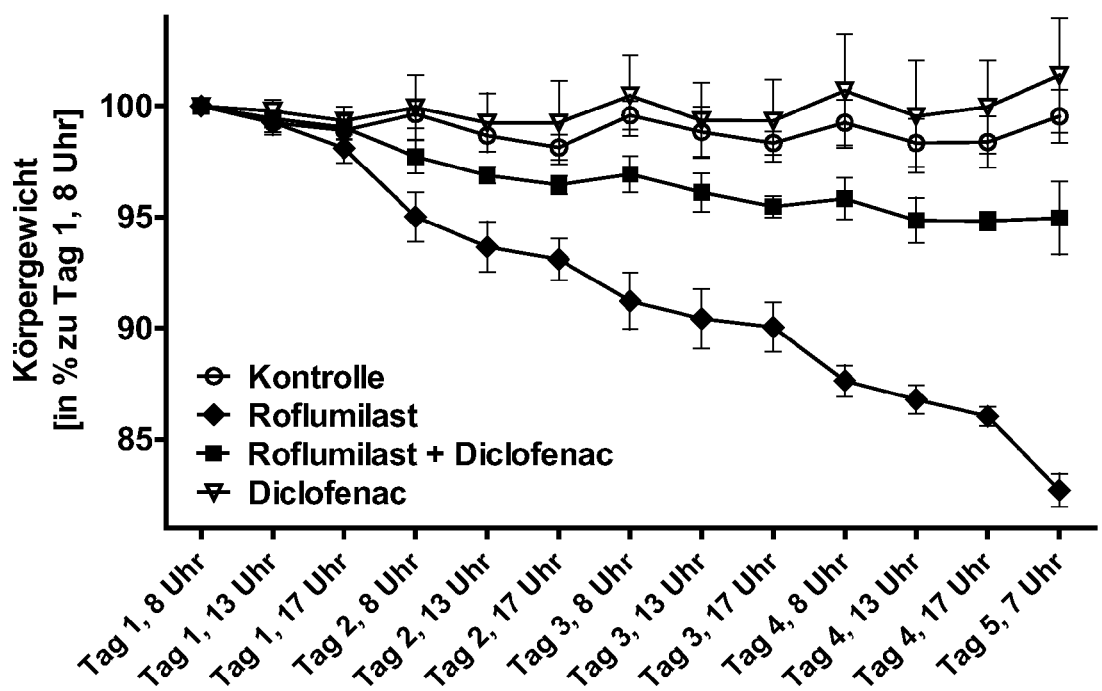
FIG. 1A shows the body weights of the rats from the different groups (control group, Roflumilast group, Roflumilast+Diclofenac group and Diclofenac group) as a percentage change from the time of the first administration (=day 1, 0800 hours (=time $t_0$)). The average±standard deviation of the body weights at time t0 was 355±17 g.

FIG. 1A shows the body weights of the rats from the different groups as a percentage change from the time of the first administration (=day 1, 0800 hours (=time $t_0$)). The average±standard deviation of the body weights at time to was 355±17 g.

At the end of the experiment (95 hours after $t_0$ (=the time of the first administration on day 1, 0800)) the proportion of white blood cells (×1000 cells/μl blood, FIG. 1B, left-hand Figure) and the proportion of neutrophils (in % of white blood cells, FIG. 1B, right-hand Figure) were determined from the blood of 4 or 5 of the rats from the individual groups.

EXPERIMENT 2

Diclofenac Provides Protection Against Roflumilast-Mediated Effects Such as Diarrhoea Six male Wistar rats in each group were treated for four days with the following substances (all substances are given p.o.=orally):
Group 1 ("control group"): Six male Wistar rats were given a daily dose of 0.5% Natrosol (placebo) at the times 0800, 1300 and 1700 hours.
Group 2 ("roflumilast group"): Six male Wistar rats were given a daily dose of 0.5% Natrosol (placebo) at 0800 and 1700 hours and 10 mg/kg roflumilast (PDE4 inhibitor) at 1300 hours.
Group 3 ("roflumilast+diclofenac group"): Six male Wistar rats were given a daily dose of 1 mg/kg diclofenac (NSAID) at the times 0800 and 1700 hours and 10 mg/kg roflumilast (PDE4 inhibitor) at 1300 hours.
Group 4 ("diclofenac group"): Six male Wistar rats were given a daily dose of 1 mg/kg diclofenac (NSAID) at the times 0800 and 1700 hours and 0.5% Natrosol (placebo) at 1300 hours.

For pharmacokinetic analysis (determining the plasma levels of the substances) on day 4 one rat from each group was used; these rats were no longer available for other parameters under investigation. The same applied to one rat from the roflumilast group which died between day 4 and day 5 of the experiment.

At the end of the experiment (95 hours after $t_0$ (=the time of the first administration on day 1, 0800 hours)) the rats from the individual groups were examined phenotypically and histopathologically for the presence of multifocal perivascular mononuclear infiltration (=inflammation parameter) in the mesentery and for the proliferation of fibroblasts in the mesentery. In addition, the occurrence of diarrhoea in the rats from the different groups was noted. The findings are summarised in Table 1 as follows:

TABLE 1

| Phenotypical and histopathological findings | | | | |
|---|---|---|---|---|
| Parameter | Control (group 1) | roflumilast (group 2) | roflumilast + diclofenac (group 3) | diclofenac (group 4) |
| Diarrhoea | 0/6 (=0 out of 6 animals) | 5/6 | 0/6 | 0/6 |
| Mesentery: multifocal perivascular mononuclear infiltration (=inflammation parameter) | 0/5 | 4/4 | 0/5 | 0/5 |
| Mesentery: Proliferation of fibroblasts | 0/5 | 4/4 | 0/5 | 0/5 |

To summarise, it can be stated that the PDE4 inhibitor-mediated side effects such as weight loss (FIG. 1A), leukocytosis (FIG. 1B, on the left), neutrophilia (FIG. 1B, on the right) and diarrhoea (including the presence of inflammation parameters and the proliferation of fibroblasts in the mesentery) observed in the roflumilast group can be substantially reduced or prevented (often even reduced to the level found in the control group), by co-administering an NSAID such as diclofenac (cf. roflumilast+diclofenac group) simultaneously or only a few hours apart. The parameters measured after the administration of diclofenac alone were found to be very similar to the control groups.

EXPERIMENT 3

The COX-2 Selective Inhibitor Lumiracoxib, but not the COX-1 Selective Inhibitor SC-560, Provides Protection from Roflumilast-Mediated Effects Such as Weight Loss, Leukocytosis and Neutrophilia:

Six male Wistar rats in each group were treated for four days with the following substances (all substances are given p.o.=orally):
Group 1 ("control group"): Six male Wistar rats were given a daily dose of 0.5% Natrosol (placebo) at the times 0800, 1300 and 1700 hours.
Group 2 ("roflumilast group"): Six male Wistar rats were given a daily dose of 0.5% Natrosol (placebo) at 0800 and 1700 hours and 10 mg/kg roflumilast (PDE4 inhibitor) at 1300 hours.
Group 3 ("roflumilast+SC-560 group"): Six male Wistar rats were given a daily dose of 2 mg/kg SC-560 (NSAID, selective for COX-1) at the times 0800 and 1700 hours and 10 mg/kg roflumilast (PDE4 inhibitor) at 1300 hours.
Group 4 ("roflumilast+lumiracoxib group"): Six male Wistar rats were given a daily dose of 2 mg/kg lumiracoxib (NSAID, selective for COX-2) at the times 0800 and 1700 hours and 10 mg/kg of reflumilast (PDE4 inhibitor) at 1300 hours.
Group 5 ("SC-560 group"): Six male Wistar rats were given a daily dose of 2 mg/kg SC-560 (NSAID, selective for COX-1) at the times 0800 and 1700 hours and 0.5% Natrosol at 1300 hours.
Group 6 ("lumiracoxib group"): Six male Wistar rats were given a daily dose of 2 mg/kg lumiracoxib (NSAID, selective for COX-2) at the times 0800 and 1700 hours and 0.5% Natrosol at 1300 hours.

For pharmacokinetic analysis (determining the plasma levels of the substances) on day 4 one rat from each group was used; these rats were no longer available for other parameters under investigation.

Figure 2A:
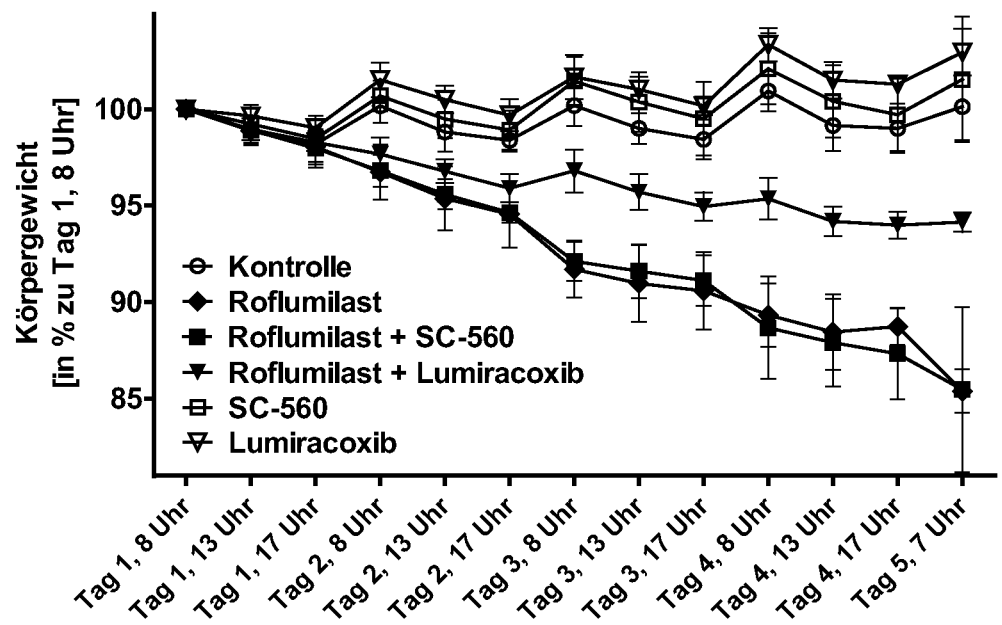
FIG. 2A shows the body weights of the rats from the different groups (control group, Roflumilast group, Roflumilast+SC-560 group, Roflumilast+Lumiracoxib group, SC-560 group and Lumiracoxib group) as a percentage change from the time of the first administration (=day 1, 0800 hours (=time $t_0$)). The average±standard deviation of the body weights at time to was 306±11 g.

FIG. 2A shows the body weights of the rats from the different groups as a percentage change from the time of the first administration (=day 1, 0800 hours (=time $t_0$)). The average±standard deviation of the body weights at time $t_0$ was 306±11 g.

At the end of the experiment (95 hours after $t_0$ (=the time of the first administration on day 1, 0800 hours)) the proportion of white blood cells (×1000 cells/µl blood, FIG. 2B, left-hand Figure) and the proportion of neutrophils (in % of white blood cells, FIG. 2B, right-hand Figure) were determined from the blood of 5 of the rats from the individual groups.

EXPERIMENT 4

The COX-2 selective inhibitor lumiracoxib, but not the COX-1 selective inhibitor SC-560, provides protection from roflumilast-mediated effects such as diarrhoea Six male Wistar rats in each group were treated for four days with the following substances (all substances are given p.o.=orally):
Group 1 ("control group"): Six male Wistar rats were given a daily dose of 0.5% Natrosol (placebo) at the times 0800, 1300 and 1700 hours.
Group 2 ("roflumilast group"): Six male Wistar rats were given a daily dose of 0.5% Natrosol (placebo) at 0800 and 1700 hours and 10 mg/kg roflumilast (PDE4 inhibitor) at 1300 hours.
Group 3 ("roflumilast+SC-560 group"): Six male Wistar rats were given a daily dose of 2 mg/kg SC-560 (NSAID, selective for COX-1) at the times 0800 and 1700 hours and 10 mg/kg roflumilast (PDE4 inhibitor) at 1300 hours.
Group 4 ("roflumilast+lumiracoxib group"): Six male Wistar rats were given a daily dose of 2 mg/kg lumiracoxib (NSAID, selective for COX-2) at the times 0800 and 1700 hours and 10 mg/kg of roflumilast (PDE4 inhibitor) at 1300 hours.
Group 5 ("SC-560 group"): Six male Wistar rats were given a daily dose of 2 mg/kg SC-560 (NSAID, selective for COX-1) at the times 0800 and 1700 hours and 0.5% Natrosol at 1300 hours.
Group 6 ("lumiracoxib group"): Six male Wistar rats were given a daily dose of 2 mg/kg lumiracoxib (NSAID, selective for COX-2) at the times 0800 and 1700 hours and 0.5% Natrosol at 1300 hours.

For pharmacokinetic analysis (determining the plasma levels of the substances) on day 4 one rat from each group was used; these rats were no longer available for other parameters under investigation.

At the end of the experiment (95 hours after $t_0$ (=the time of the first administration on day 1, 0800 hours)) the rats from the individual groups were examined phenotypically and histopathologically for the presence of multifocal perivascular mononuclear infiltration (=inflammation parameter) in the mesentery and for the proliferation of fibroblasts in the mesentery. In addition, the occurrence of diarrhoea in the rats from the different groups was noted. The findings are summarised in Table 2 as follows:

TABLE 2

Phenotypical and histopathological findings

| Parameter | control (group 1) | roflumilast (group 2) | roflumilast + SC-560 (group 3) | roflumilast + lumiracoxib (group 4) | SC-560 (group 5) | lumiracoxib (group 6) |
|---|---|---|---|---|---|---|
| Diarrhoea | 0/6 (=0 von 6 Tieren) | 2/6 | 0/6 | 0/6 | 0/6 | 0/6 |
| Mesentery: multifocal perivascular mononuclear infiltration (=inflammation parameter) | 0/5 | 5/5 | 4/5 | 0/5 | 0/5 | 0/5 |

TABLE 2-continued

Phenotypical and histopathological findings

| Parameter | control (group 1) | roflumilast (group 2) | roflumilast + SC-560 (group 3) | roflumilast + lumiracoxib (group 4) | SC-560 (group 5) | lumiracoxib (group 6) |
|---|---|---|---|---|---|---|
| Mesentery: Proliferation of fibroblasts | 0/5 | 5/5 | 4/5 | 0/5 | 0/5 | 0/5 |

To summarise, it can be stated that the PDE4 inhibitor-mediated side effects such as weight loss (FIG. 2A), leukocytosis (FIG. 2, on the left), neutrophilia (FIG. 2B, on the right) and diarrhoea (including the presence of inflammation parameters and the proliferation of fibroblasts in the mesentery) observed in the roflumilast group can be substantially reduced or prevented (often even reduced to the level found in the control group), by co-administering a COX-2 selective NSAID such as lumiracoxib (cf. roflumilast+lumiracoxib) simultaneously or only a few hours apart. The COX-1 selective NSAID SC-560 has absolutely no protective effect on weight loss, leukocytosis and neutrophilia and only a very slight protective effect on the histopathological findings (multifocal perivascular mononuclear infiltration or proliferation of fibroblasts in the mesentery). It is difficult to make any pronouncements as to the effect of SC-560 on diarrhoea because in this experiment, in the roflumilast group, diarrhoea was only found per se in two animals (as a rule, an even greater percentage of the animals exhibit diarrhoea after the administration of roflumilast). The parameters measured after the administration of SC-560 or lumiracoxib alone were found to be very similar to the control groups.

To sum up, it can be concluded that the protective effect of an NSAID on the PDE4 inhibitor-mediated side effects are based on the inhibition of COX-2.

Formulations

The active substance combinations of 1 and 2 are preferably administered orally. For this purpose the ingredients ( ) and (2) have to be presented in suitable oral preparations.

Suitable oral forms for administration are for example tablets, capsules, solutions, syrups or emulsions. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension.

It is particularly preferable if the preparations are administered once or twice a day. Suitable tablets may be obtained, for example, by mixing the active substance(s) with known excipients, for example inert diluents such as calcium carbonate, calcium phosphate, microcrystalline cellulose, sorbitol, mannitol, isomaltose or lactose, disintegrants such as corn starch, crosslinked polyvinyl pyrrolidone, crosslinked sodium carboxymethylcellulose, sodium starch glycolate or alginic acid, binders such as starch, hydroxypropylmethylcellulose, polyvinylpyrrolidone or gelatine, lubricants, such as magnesium stearate or talc, and/or agents for delaying release, such as hydroxypropylcellulose, hydroxypropylmethylcellulose, ethylcellulose, aminomethacrylate, polyvinylpyrrolidone-polyvinylacetate copolymer, carboxymethylcellulose or polyvinylacetate. The tablets may also comprise several layers.

Coated tablets or film-coated tablets may be prepared accordingly by coating cores produced analogously to the tablets with substances normally used for tablet or film coatings, for example collidone or shellac, gum arabic, talc, titanium dioxide, sugar, hydroxypropylmethyl cellulose, ethycellulose, cellulose acetate phthalate, polymethacrylate, polyethyleneglycol, polyvinylalcohol, polyvinylalcohol-polyethyleneglycol copolymers or polyvinylacetate. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like.

Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

Examples of Formulations:

The following formulation examples for combined formulations are intended to serve to illustrate the invention without restricting it thereto. In particular, the active substances 1 and 2 may also be present in separate formulations and administered separately within a time window of not more than 6 hours.

1)
| | 0.05 | mg | active substance 1 |
|---|---|---|---|
| | 500 | mg | acetylsalicylic acid (active substance 2) |
| | 100 | mg | lactose |
| | 329.95 | mg | microcrystalline cellulose |
| | 30 | mg | polyvinylpyrrolidone |
| | 30 | mg | crosslinked polyvinylpyrrolidone |
| | 10 | mg | magnesium stearate |
| | 1000 | mg | |

2)
| | 0.1 | mg | active substance 1 |
|---|---|---|---|
| | 500 | mg | acetylsalicylic acid (active substance 2) |
| | 100 | mg | lactose |
| | 329.9 | mg | microcrystalline cellulose |
| | 30 | mg | crosslinked polyvinylpyrrolidone |
| | 30 | mg | polyvinylpyrrolidone |
| | 10 | mg | magnesium stearate |
| | 1000 | mg | |

3)
| | 0.5 | mg | active substance 1 |
|---|---|---|---|
| | 500 | mg | acetylsalicylic acid (active substance 2) |
| | 100 | mg | lactose |
| | 329.5 | mg | microcrystalline cellulose |
| | 30 | mg | crosslinked polyvinylpyrrolidone |
| | 30 | mg | polyvinylpyrrolidone |
| | 10 | mg | magnesium stearate |
| | 1000 | mg | |

4)
| | 5 | mg | active substance 1 |
|---|---|---|---|
| | 500 | mg | acetylsalicylic acid (active substance 2) |
| | 100 | mg | lactose |
| | 325 | mg | microcrystalline cellulose |
| | 30 | mg | crosslinked polyvinylpyrrolidone |
| | 30 | mg | polyvinylpyrrolidone |
| | 10 | mg | magnesium stearate |
| | 1000 | mg | |

5)
| | 20 | mg | active substance 1 |
|---|---|---|---|
| | 500 | mg | acetylsalicylic acid (active substance 2) |
| | 100 | mg | lactose |
| | 310 | mg | microcrystalline cellulose |
| | 30 | mg | crosslinked polyvinylpyrrolidone |
| | 30 | mg | polyvinylpyrrolidone |
| | 10 | mg | magnesium stearate |
| | 1000 | mg | |

6)
| | 0.05 | mg | active substance 1 |
|---|---|---|---|
| | 25 | mg | diclofenac (active substance 2) |
| | 170 | mg | lactose |
| | 269.95 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

7)
| | 0.1 | mg | active substance 1 |
|---|---|---|---|
| | 25 | mg | diclofenac (active substance 2) |
| | 170 | mg | lactose |
| | 269.9 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

8)
| | 0.5 | mg | active substance 1 |
|---|---|---|---|
| | 25 | mg | diclofenac (active substance 2) |
| | 170 | mg | lactose |
| | 269.5 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

9)
| | 5 | mg | active substance 1 |
|---|---|---|---|
| | 25 | mg | diclofenac (active substance 2) |
| | 170 | mg | lactose |
| | 265 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

10)
| | 20 | mg | active substance 1 |
|---|---|---|---|
| | 25 | mg | diclofenac (active substance 2) |
| | 170 | mg | lactose |
| | 240 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

11)
| | 0.05 | mg | active substance 1 |
|---|---|---|---|
| | 15 | mg | meloxicam (active substance 2) |
| | 170 | mg | lactose |
| | 279.95 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

12)
| | 0.1 | mg | active substance 1 |
|---|---|---|---|
| | 15 | mg | meloxicam (active substance 2) |
| | 170 | mg | lactose |
| | 279.9 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

13)
| | 0.5 | mg | active substance 1 |
|---|---|---|---|
| | 15 | mg | meloxicam (active substance 2) |
| | 170 | mg | lactose |
| | 279.5 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

14)
| | 5 | mg | active substance 1 |
|---|---|---|---|
| | 15 | mg | meloxicam (active substance 2) |
| | 170 | mg | lactose |
| | 275 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

15)
| | 20 | mg | active substance 1 |
|---|---|---|---|
| | 15 | mg | meloxicam (active substance 2) |
| | 170 | mg | lactose |
| | 260 | mg | microcrystalline cellulose |
| | 15 | mg | crosslinked polyvinylpyrrolidone |
| | 15 | mg | polyvinylpyrrolidone |
| | 5 | mg | magnesium stearate |
| | 500 | mg | |

16)
| | 0.05 | mg | active substance 1 |
|---|---|---|---|
| | 500 | mg | naproxen (active substance 2) |
| | 100 | mg | lactose |
| | 329.95 | mg | microcrystalline cellulose |
| | 30 | mg | crosslinked polyvinylpyrrolidone |
| | 30 | mg | polyvinylpyrrolidone |
| | 10 | mg | magnesium stearate |
| | 1000 | mg | |

17)
| | 0.1 | mg | active substance 1 |
|---|---|---|---|
| | 500 | mg | naproxen (active substance 2) |
| | 100 | mg | lactose |
| | 329.9 | mg | microcrystalline cellulose |
| | 30 | mg | crosslinked polyvinylpyrrolidone |
| | 30 | mg | polyvinylpyrrolidone |
| | 10 | mg | magnesium stearate |
| | 1000 | mg | |

18)
| | 0.5 | mg | active substance 1 |
|---|---|---|---|
| | 500 | mg | naproxen (active substance 2) |

-continued

|    |           |                                  |
|----|-----------|----------------------------------|
|    | 100 mg    | lactose                          |
|    | 329.5 mg  | microcrystalline cellulose       |
|    | 30 mg     | crosslinked polyvinylpyrrolidone |
|    | 30 mg     | polyvinylpyrrolidone             |
|    | 10 mg     | magnesium stearate               |
|    | 1000 mg   |                                  |
| 19)| 5 mg      | active substance 1               |
|    | 500 mg    | naproxen (active substance 2)    |
|    | 100 mg    | lactose                          |
|    | 325 mg    | microcrystalline cellulose       |
|    | 30 mg     | crosslinked polyvinylpyrrolidone |
|    | 30 mg     | polyvinylpyrrolidone             |
|    | 10 mg     | magnesium stearate               |
|    | 1000 mg   |                                  |
| 20)| 20 mg     | active substance 1               |
|    | 500 mg    | naproxen (active substance 2)    |
|    | 100 mg    | lactose                          |
|    | 310 mg    | microcrystalline cellulose       |
|    | 30 mg     | crosslinked polyvinylpyrrolidone |
|    | 30 mg     | polyvinylpyrrolidone             |
|    | 10 mg     | magnesium stearate               |
|    | 1000 mg   |                                  |
| 21)| 0.05 mg   | active substance 1               |
|    | 200 mg    | ibuprofen (active substance 2)   |
|    | 100 mg    | lactose                          |
|    | 258.95 mg | microcrystalline cellulose       |
|    | 18 mg     | crosslinked polyvinylpyrrolidone |
|    | 18 mg     | polyvinylpyrrolidone             |
|    | 5 mg      | magnesium stearate               |
|    | 600 mg    |                                  |
| 22)| 0.1 mg    | active substance 1               |
|    | 200 mg    | ibuprofen (active substance 2)   |
|    | 100 mg    | lactose                          |
|    | 258.9 mg  | microcrystalline cellulose       |
|    | 18 mg     | crosslinked polyvinylpyrrolidone |
|    | 18 mg     | polyvinylpyrrolidone             |
|    | 5 mg      | magnesium stearate               |
|    | 600 mg    |                                  |
| 23)| 0.5 mg    | active substance 1               |
|    | 200 mg    | ibuprofen (active substance 2)   |
|    | 100 mg    | lactose                          |
|    | 258.5 mg  | microcrystalline cellulose       |
|    | 18 mg     | crosslinked polyvinylpyrrolidone |
|    | 18 mg     | polyvinylpyrrolidone             |
|    | 5 mg      | magnesium stearate               |
|    | 600 mg    |                                  |
| 24)| 5 mg      | active substance 1               |
|    | 200 mg    | ibuprofen (active substance 2)   |
|    | 100 mg    | lactose                          |
|    | 254 mg    | microcrystalline cellulose       |
|    | 18 mg     | crosslinked polyvinylpyrrolidone |
|    | 18 mg     | polyvinylpyrrolidone             |
|    | 5 mg      | magnesium stearate               |
|    | 600 mg    |                                  |
| 25)| 20 mg     | active substance 1               |
|    | 200 mg    | ibuprofen (active substance 2)   |
|    | 100 mg    | lactose                          |
|    | 239 mg    | microcrystalline cellulose       |
|    | 18 mg     | crosslinked polyvinylpyrrolidone |
|    | 18 mg     | polyvinylpyrrolidone             |
|    | 5 mg      | magnesium stearate               |
|    | 600 mg    |                                  |

The finely ground active substance, lactose and some of the microcrystalline cellulose are mixed together. The mixture is screened, then moistened with a solution of polyvinylpyrrolidone in water, kneaded, wet-granulated and dried. The granules, the rest of the microcrystalline cellulose and the crosslinked polyvinylpyrrolidone are screened and mixed together. Then the magnesium stearate is screened in and briefly mixed in. The mixture is compressed to form tablets of suitable shape and size.

The invention claimed is:
1. A drug combination comprising a PDE4 inhibitor of formula 1

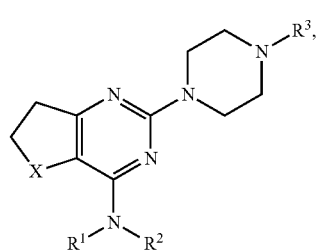

wherein:
X is SO or $SO_2$;
$R^1$ is H or $C_{1-6}$-alkyl;
$R^2$ is H or a group selected from $C_{1-40}$-alkyl and $C_{2-6}$-alkenyl, each optionally substituted by one or more groups selected from halogen and $C_{1-3}$-fluoroalkyl or optionally substituted by one or more groups selected from $OR^{2.1}$, $COOR^{2.1}$, $CONR^{2.2}R^{2.3}$, $SR^{2.1}$, $SO$—$R^{2.1}$, $SO_2$—$R^{2.1}$, $C_{6-10}$-aryl, het, hetaryl, a mono- or bicyclic $C_{3-10}$-cycloalkyl, $CH_2$—$NR^{2.2}R^{2.3}$, and $NR^{2.2}R^{2.3}$, which in turn is optionally substituted by one or more groups selected from OH, halogen, $OR^{2.1}$, oxo, $CF_3$, $CHF_2$, $CH_2F$, $C_{1-6}$-alkyl, $C_{1-6}$-alkanol, $C_{6-10}$-aryl, $COOR^{2.1}$, $CH_2$—$NR^{2.2}R^{2.3}$, and $NR^{2.2}R^{2.3}$,
$R^2$ is a mono- or polycyclic $C_{3-10}$ cycloalkyl optionally singly or multiply bridged by $C_{1-3}$-alkyl groups and optionally substituted by a group selected from branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, het, $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl, and $NR^{2.2}R^{2.3}$, each of which is optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{2.2}R^{2.3}$,
$R^2$ is a mono- or polycyclic $C_{6-10}$-aryl optionally substituted by OH, SH, or halogen or by one or more groups selected from $OR^{2.1}$, $COOR^{2.1}$, $NR^{2.2}R^{2.3}$, $CH_2$—$NR^{2.2}R^{2.3}$, $C_{3-10}$-cycloalkyl, het, —$C_{1-6}$-alkyl, $C_{1-3}$-fluoroalkyl, $C_{6-10}$-aryl-$C_{1-6}$-alkylene, het-$C_{1-6}$-alkylene, hetaryl-$C_{1-6}$-alkylene, $C_{6-10}$-aryl, $SO_2$—$CH_3$, $SO_2$—$CH_2CH_3$, and $SO_2$—$NR^{2.2}R^{2.3}$, each of which in turn is optionally substituted by one or more groups selected from OH, $OR^{2.1}$, $CF_3$, $CHF_2$, $CH_2F$, oxo, halogen, $CF_3$, $CHF_2$, $CH_2F$, $C_{1-6}$-alkyl, $C_{6-10}$-aryl, and $NR^{2.2}R^{2.3}$,
$R^2$ is a group selected from het and hetaryl, each optionally substituted by one or more groups selected from halogen, OH, oxo, $CF_3$, $CHF_2$, and $CH_2F$ or by one or more groups selected from $OR^{2.1}$, $C_{1-3}$-alkylene-$OR^{2.1}$, $SR^{2.1}$, $SO$—$R^{2.1}$, $SO_2$—$R^{2.1}$, $COOR^{2.1}$, $COR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl, $C_{1-3}$-alkylene-$OR^{2.1}$, and $NR^{2.2}R^{2.3}$, each of which in turn is optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{2.2}R^{2.3}$, or NR$^1$R$^2$ together is a heterocyclic four- to seven-membered ring optionally bridged, which contains 1, 2, or 3 heteroatoms selected from N, O, and S, and which is optionally substituted by one or more groups selected from OH, OR$^{2.1}$, C$_{1-3}$-alkylene-OR$^{2.1}$, oxo, halogen, C$_{1-6}$-alkyl, C$_{6-10}$-aryl, COOR$^{2.1}$, CH$_2$—NR$^{2.2}$—COO—R$^{2.1}$, CH$_2$—NR$^{2.2}$—CO—R$^1$, CH$_2$—NR$^{2.2}$—CO—CH$_2$—NR$^{2.2}$R$^{2.3}$, CH$_2$—NR$^{2.2}$—SO$_2$—C$_{1-3}$-alkyl, CH$_2$—NR$^{2.2}$—SO$_2$—NR$^{2.2}$R$^{2.3}$, CH$_2$—NR$^{2.2}$—CO—NR$^{2.2}$R$^{2.3}$, CO—NR$^{2.2}$R$^{2.3}$, CH$_2$—NR$^{2.2}$R$^{2.3}$, and NR$^{2.2}$R$^{2.3}$; and R$^3$ is a group selected from het and hetaryl, each optionally substituted by one or more groups selected from halogen, C$_{1-3}$-fluoroalkyl, CN, OH, oxo, —C$_{1-6}$-alkyl, —O—R$^{2.1}$, —COOR$^{2.1}$, SO—R$^{2.1}$, SO$_2$—R$^{2.1}$, C$_{6-10}$-aryl, C$_{1-3}$-alkylene-C$_{6-10}$-aryl, —C$_{1-3}$-alkylene-NR$^{2.2}$R$^{2.3}$, —NR$^{2.2}$R$^{2.3}$, a C$_{3-10}$-cycloalkyl, a C$_{1-3}$-alkylene-C$_{3-10}$-cycloalkyl, a het, a hetaryl, C$_{1-3}$-alkylene-hetaryl, and C$_{1-3}$-alkylene-het, each of which in turn is optionally substituted by one or more groups selected from OH, halogen, —C$_{1-3}$-fluoroalkyl, C$_{1-6}$-alkyl, C$_{6-10}$-aryl, —COO(C$_{1-3}$-alkyl), and O—(C$_{1-3}$-alkyl), and wherein:

het is a three- to eleven-membered, mono- or bicyclic, saturated or partly saturated, optionally annelated or optionally bridged heterocyclic group which contains 1, 2, 3, or 4 heteroatoms independently selected from N, S, or O, hetaryl is a five- to eleven-membered, mono- or bicyclic, optionally annelated heteroaryl which contains 1, 2, 3, or 4 heteroatoms independently selected from N, S, or O, cycloalkyl is saturated or partly saturated, R$^{2.1}$ is H or a group selected from C$_{1-6}$-alkyl, C$_{1-6}$-alkanol, C$_{1-3}$-haloalkyl, mono- or bicyclic C$_{3-10}$-cycloalkyl, C$_{6-10}$-aryl-C$_{1-6}$-alkylene, mono- or bicyclic hetaryl-C$_{1-6}$-alkylene, het-C$_{1-6}$-alkylene, C$_{3-10}$-cycloalkyl-C$_{1-6}$-alkylene, a mono- or bicyclic C$_{6-10}$-aryl, hetaryl, and het, each optionally substituted by one or more groups selected from OH, O—(C$_{1-3}$-alkyl), halogen, C$_{1-6}$-alkyl, and C$_{6-10}$-aryl, and R$^{2.2}$ and R$^{2.3}$ are each independently H or a group selected from C$_{1-6}$-alkyl, mono- or bicyclic C$_{3-10}$ cycloalkyl, C$_{6-10}$-aryl-C$_{1-6}$-alkylene, hetaryl-C$_{1-6}$-alkylene, mono- or bicyclic C$_{6-10}$-aryl, het, hetaryl, CO—NH$_2$, CO—NHCH$_3$, CO—N(CH$_3$)$_2$, SO$_2$—(C$_1$-C$_2$-alkyl), CO—R$^{2.1}$, and COOR$^{2.1}$, each optionally substituted by one or more groups selected from OH, halogen, C$_{1-6}$-alkyl, C$_{6-10}$-aryl and COOR$^{2.1}$, and an NSAID.

2. The drug combination according to claim 1, wherein:

X is SO;

R$^1$ is H;

R$^2$ is H or C$_{1-6}$-alkyl optionally substituted by one or more groups selected from F, CF$_3$, CHF$_2$, or CH$_2$F or optionally substituted by one or more groups selected from OR$^{2.1}$, COOR$^{2.1}$, CONR$^{2.2}$R$^{2.3}$, SR$^{2.1}$, SO—R$^{2.1}$, SO$_2$—R$^{2.1}$, phenyl, het, hetaryl, a monocyclic C$_{3-7}$-cycloalkyl, CH$_2$—NR$^{2.2}$R$^{2.3}$, and NR$^{2.2}$R$^{2.3}$, each of which in turn is optionally substituted by one or more groups selected from OH, F, Cl, Br, CF$_3$, CHF$_2$, CH$_2$F, OR$^{2.1}$, oxo, methyl, ethyl, propyl, isopropyl, C$_{1-2}$-alkanol, phenyl, COOR$^{2.1}$, CH$_2$—NR$^{2.2}$R$^{2.3}$, and NR$^{2.2}$R$^{2.3}$, R$^2$ is a monocyclic C$_{3-7}$ cycloalkyl optionally substituted by a group selected from branched or unbranched C$_{1-2}$-alkanol, C$_{1-3}$-fluoroalkyl, C$_{1-3}$-alkylene-OR$^{2.1}$, OR$^{2.1}$, COOR$^{2.1}$, SO$_2$—NR$^{2.2}$R$^{2.3}$, het, methyl, ethyl, propyl, isopropyl, phenyl, phenyl-C$_{1-2}$-alkylene, hetaryl-C$_{1-2}$-alkylene, monocyclic C$_{3-7}$ cycloalkyl, and NR$^{2.2}$R$^{2.3}$, each optionally substituted by one or more groups selected from OH, OR$^{2.1}$, oxo, halogen, CF$_3$, CHF$_2$, CH$_2$F, methyl, ethyl, propyl, isopropyl, phenyl, and NR$^{2.2}$R$^{2.3}$, or R$^2$ is a phenyl optionally substituted by OH, SH, F, Cl or Br or by one or more groups selected from OR$^{2.1}$, COOR$^{2.1}$, NR$^{2.2}$R$^{2.3}$, CH$_2$—NR$^{2.2}$R$^{2.3}$, C$_{3-7}$-cycloalkyl, het, methyl, ethyl, propyl, isopropyl, CF$_3$, CHF$_2$, CH$_2$F, phenyl-C$_{1-2}$-alkylene, het-C$_{1-2}$-alkylene, hetaryl-C$_{1-2}$-alkylene, phenyl, SO$_2$—CH$_3$, SO$_2$—CH$_2$CH$_3$, and SO$_2$—NR$^{2.2}$R$^{2.3}$, which in turn are optionally substituted by one or more groups selected from OH, OR$^{2.1}$, oxo, F, Cl, Br, CF$_3$, CHF$_2$, CH$_2$F, methyl, ethyl, propyl, isopropyl, phenyl, and NR$^{2.2}$R$^{2.3}$, or R$^2$ is a group selected from het and hetaryl, which are optionally substituted by one or more groups selected from F, Cl, Br, OH, oxo, CF$_3$, CHF$_2$, CH$_2$F and SH or by one or more groups selected from OR$^{2.1}$, C$_{1-3}$-alkylene-OR$^{2.1}$, SR$^{2.1}$, SO—R$^{2.1}$, SO$_2$—R$^{2.1}$, COOR$^{2.1}$, COR$^{2.1}$, C$_{1-2}$-alkanol, C$_{3-10}$-cycloalkyl, phenyl, methyl, ethyl, propyl, isopropyl, phenyl-C$_{1-2}$-alkylene, hetaryl-C$_{1-2}$-alkylene, het, hetaryl, C$_{1-2}$-alkanol, and NR$^{2.2}$R$^{2.3}$, which in turn are optionally substituted by one or more groups selected from OH, OR$^{2.1}$, oxo, F, Cl, Br, CF$_3$, CHF$_2$, CH$_2$F, C$_{1-6}$-alkyl, phenyl, and NR$^{2.2}$R$^{2.3}$, and wherein R$^3$ is a group selected from a saturated or partly saturated, monocyclic three- to seven-membered heterocyclic group, a saturated or partly saturated, bicyclic five- to eleven-membered heterocyclic group, a monocyclic, five- to six-membered heteroaryl and a bicyclic, seven- to eleven-membered heteroaryl, which contains in each case 1, 2, 3, or 4 heteroatoms selected independently from N, O, and S, and optionally substituted in each case by one or more groups selected from halogen, C$_{1-3}$-fluoroalkyl, CN, OH, oxo, —C$_{1-6}$-alkyl, —O—R$^{2.1}$, —COOR$^{2.1}$, SO—R$^{2.1}$, SO$_2$—R$^{2.1}$, C$_{6-10}$-aryl, C$_{1-3}$-alkylene-C$_{6-10}$-aryl, —C$_{1-3}$-alkylene-NR$^{2.2}$R$^{2.3}$, —NR$^{2.2}$R$^{2.3}$, a C$_{3-10}$-cycloalkyl, a C$_{1-3}$-alkylene-C$_{3-10}$-cycloalkyl, het, a hetaryl, C$_{1-3}$-alkylene-hetaryl, and C$_{1-3}$-alkylene-het, which in turn are optionally substituted by one or more groups selected from OH, halogen, —C$_{1-3}$-fluoroalkyl, C$_{1-6}$-alkyl, C$_{6-10}$-aryl, —COO(C$_{1-3}$-alkyl) and O—(C$_3$-alkyl), and wherein:

R$^{2.1}$ is H or a group selected from methyl, ethyl, propyl, isopropyl, monocyclic C$_{3-7}$ cycloalkyl, phenyl-C$_{1-2}$-alkylene, hetaryl-C$_{1-2}$-alkylene, het-C$_{1-2}$-alkylene, C$_{3-7}$-cycloalkyl-C$_{1-2}$-alkylene, phenyl, hetaryl, and het, each optionally substituted by one or more groups selected from OH, halogen, methyl, ethyl, propyl, isopropyl, —O-methyl, —O-ethyl, —O-propyl, —O-isopropyl, and phenyl, R$^{2.2}$ and R$^{2.3}$ are each independently H or a group selected from methyl, ethyl, propyl, isopropyl, monocyclic C$_{3-7}$cycloalkyl, phenyl-C$_{1-3}$-alkylene, hetaryl-C$_{1-3}$-alkylene, phenyl, het, hetaryl, CO—NH$_2$, CO—NHCH$_3$, CON(CH$_3$)$_2$, SO$_2$—(C$_1$-C$_2$-alkyl), CO—R$^{2.1}$, and COOR$^{2.1}$, each optionally substituted by one or more groups selected from OH, F, Cl, Br, methyl, ethyl, propyl, isopropyl, phenyl, and COOR$^{2.1}$, het is a three- to seven-membered, monocyclic, saturated or partly saturated heterocyclic group which contains 1, 2, or 3 heteroatoms independently selected from N, S, or O, and hetaryl is a five- to six-membered, monocyclic, aromatic heteroaryl which contains 1, 2, or 3 heteroatoms independently selected from N, S, or O.

3. The drug combination according to claim 1, wherein:
$R^2$ is a group according to formula 3

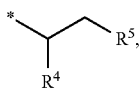

wherein:
$R^5$ is OH or $NH_2$, and
$R^4$ is a group selected from $C_{1-4}$-alkyl, hetaryl, and phenyl, each of which is optionally substituted by one or more groups selected from OH, F, Br, $OR^{2.1}$, oxo, methyl, ethyl, $C_{1-2}$-alkanol, phenyl, $COOR^{2.1}$, $CH_2$—$NR^{2.2}R^{2.3}$, and $NR^{2.2}R^{2.3}$.

4. The drug combination according to claim 3, wherein:
$R^4$ is methyl, ethyl, propyl, or isopropyl.

5. The drug combination according to claim 1, wherein:
$R^2$ is a monocyclic three-, four-, five-, six-, or seven-membered cycloalkyl ring optionally substituted in the spiro position by a group selected from —$CH_2$—$OR^{2.1}$, branched or unbranched $C_{2-6}$-alkylene-$OR^{2.1}$, methyl, ethyl, propyl, isopropyl, butyl, isobutyl, cyclopropyl, —$CF_3$, $CHF_2$, $CH_2F$, and $C_{2-4}$-fluoroalkyl, wherein $R^{2.1}$ is methyl, ethyl, propyl, isopropyl, butyl, or isobutyl.

6. The drug combination according to claim 1, wherein:
$R^2$ is phenyl optionally substituted in one or both meta positions by one or more groups selected from methyl, ethyl, propyl, isopropyl, cyclopropyl, F, Cl, Br, OH, $OR^{2.1}$, $COOR^{2.1}$, $CF_3$, $CHF_2$, $CH_2F$, $NH_2$, and $N(CH_3)_2$, wherein $R^{2.1}$ is H, methyl, or ethyl.

7. The drug combination according to claim 1, wherein:
$R^2$ is a monocyclic, saturated three-, four-, five-, six-, or seven-membered heterocyclic group with 1, 2, or 3 heteroatoms in each case selected from N, O, and S, which is optionally substituted by one or more groups selected from fluorine, chlorine, bromine, $CF_3$, $CHF_2$, $CH_2F$, OH, oxo, and SH or by one or more groups selected from $OR^{2.1}$, $C_{1-3}$-alkylene-$OR^{2.1}$, $SR^{2.1}$, $SO$—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl, and $NR^{2.2}R^{2.3}$, each of which in turn is optionally substituted by one or more groups selected from OH, $OR^{2.1}$, oxo, F, Cl, $CF_3$, $CHF_2$, $CH_2F$, $C_{1-6}$-alkyl, phenyl, and $NR^{2.2}R^2$.

8. The drug combination according to claim 7, wherein:
$R^2$ is a monocyclic, saturated, six-membered heterocyclic group with a heteroatom selected from N, O, and S, which is optionally substituted by one or more groups selected from F, Cl, Br, $CF_3$, $CHF_2$, $CH_2F$, OH, oxo, $NH_2$, $NHCH_3$, $N(CH_3)_2$, methyl, ethyl, propyl, isopropyl, cyclopropyl, methoxy, and ethoxy.

9. The drug combination according to claim 8, wherein:
$R^2$ is piperidine or tetrahydropyran, each optionally substituted by one or more groups selected from F, Cl, Br, OH, $CF_3$, $CHF_2$, $CH_2F$, $NH_2$, $NHCH_3$, $N(CH_3)_2$, oxo, methyl, and methoxy.

10. The drug combination according to claim 1, wherein:
$R^3$ is a monocyclic five- or six-membered heteroaryl ring optionally substituted by one or more groups selected from F, Cl, Br, $CF_3$, $CHF_2$, $CH_2F$, CN, OH, -methyl, ethyl, propyl, isopropyl, —O-methyl, —O-ethyl, —COOmethyl, —COOethyl, $SO_2$—$(CH_3)$, SO—$(CH_3)$, $SO_2$—$(CH_2CH_3)$, SO—$(CH_2CH_3)$, phenyl, -methylene-phenyl, -ethylene-phenyl, —$NH_2$, —NH$(CH_3)$, $N(CH_3)_2$, -methylene-$NH_2$, -methylene-NH$(CH_3)$, -methylene-$N(CH_3)_2$, $C_{3-6}$-cycloalkyl, methylene-$C_{3-6}$-cycloalkyl, a saturated or partly saturated, five- to six-membered heterocyclic group, a five- or six-membered heteroaryl, -methylene-hetaryl, and -methylene-het, each of which in turn is optionally substituted by one or more groups selected from OH, F, Cl, Br, $CF_3$, $CHF_2$, $CH_2F$, methyl, ethyl, propyl, isopropyl, phenyl, —COO$(CH_3)$, —O-methyl, and —O-ethyl.

11. The drug combination according to claim 1, wherein:
$R^3$ is a bicyclic 9- to 11-membered saturated, unsaturated, or partly saturated heterocyclic group optionally substituted by one or more groups selected from F, Cl, Br, $CF_3$, $CHF_2$, $CH_2F$, CN, OH, -methyl, ethyl, propyl, isopropyl, —O-methyl, —O-ethyl, —COOmethyl, —COOethyl, $SO_2$—$(CH_3)$, SO—$(CH_3)$, $SO_2$—$(CH_2CH_3)$, SO—$(CH_2CH_3)$, phenyl, -methylene-phenyl, -ethylene-phenyl, —$NH_2$, —NH$(CH_3)$, $N(CH_3)_2$, -methylene-$NH_2$, -methylene-NH$(CH_3)$, -methylene-$N(CH_3)_2$, $C_{3-6}$-cycloalkyl, methylene-$C_{3-6}$-cycloalkyl, a saturated, partly unsaturated, or unsaturated 5- to 6-membered heterocyclic group, a 5- to 6-membered heteroaryl, -methylene-hetaryl, and -methylene-het, each of which in turn is optionally substituted by one or more groups selected from OH, F, Cl, Br, $CF_3$, $CHF_2$, $CH_2F$, methyl, ethyl, propyl, isopropyl, phenyl, —COO$(CH_3)$, —O-methyl, and —O-ethyl.

12. The drug combination according to claim 10, wherein:
$R^3$ is pyrrole, pyrazole, furan, thiophene, thiazole, imidazole, oxazole, pyridazine, pyrimidine, pyrazine, thiadiazole, oxadiazole, triazine, isooxazole, isothiazole, or pyridine, each of which is optionally substituted by one or more groups selected from F, Cl, Br, $CF_3$, $CHF_2$, $CH_2F$, methyl, ethyl, propyl, isopropyl, —O-methyl, —O-ethyl, —COOmethyl, —COOethyl, $SO_2$—$(CH_3)$, $SO_2$—$(CH_2CH_3)$, phenyl, -methylene-phenyl, -ethylene-phenyl, —$NH_2$, —NH$(CH_3)$, $N(CH_3)_2$, -methylene-$NH_2$, -methylene-NH$(CH_3)$, -methylene-$N(CH_3)_2$, $C_{3-6}$-cycloalkyl, methylene-$C_{3-6}$-cycloalkyl, het, hetaryl, -methylene-hetaryl, and -methylene-het, each of which in turn is optionally substituted by one or more groups selected from OH, F, Cl, Br, $CF_3$, $CHF_2$, $CH_2F$, methyl, ethyl, propyl, isopropyl, phenyl, —COO$(CH_3)$, —O-methyl, and —O-ethyl.

13. The drug combination according to claim 11, wherein:
$R^3$ is benzoxazole, benzodioxole, dihydrobenzodioxin, benzodioxin, benzisoxazole, benzothiazole, benzisothiazole, thienopyrimidine, furopyrimidine, thienopyridine, furopyridine, indole, isoindole, quinoxaline, naphthyridine, pyridopyrazine, pyridopyrimidine, quinoline, isoquinoline, benzoimidazole, 6,7,8,9-tetrahydro-5H-pyrazino[2,3-d]azepine, benzothiophene, benzofuran, quinazoline, indazole, isobenzofuran, or pteridine, each of which is optionally substituted by one or more groups selected from F, Cl, Br, $CF_3$, $CHF_2$, $CH_2F$, CN, OH, methyl, ethyl, propyl, isopropyl, —O-methyl, —O-ethyl, —COOmethyl, —COOethyl, $SO_2$—$(CH_3)$, $SO_2$—$(CH_2CH_3)$, phenyl, -methylene-phenyl, -ethylene-phenyl, —$NH_2$, —NH (CH₃), N(CH₃)₂, -methylene-NH₂, -methylene-NH (CH₃), -methylene-N(CH₃)₂, $C_{3-6}$-cycloalkyl, methylene-$C_{3-6}$-cycloalkyl, het, hetaryl, -methylene-hetaryl, and -methylene-het, each of which in turn is optionally substituted by one or more groups selected from OH, F, Cl, Br, CF₃, CHF₂, CH₂F, methyl, ethyl, propyl, isopropyl, phenyl, —COO(CH₃), —O-methyl, and —O-ethyl.

14. The drug combination according to claim 1, wherein:

$R^1$ is H;

$R^2$ is a group selected from

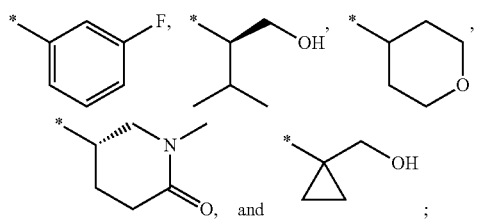

and;

$R^3$ is a group selected from

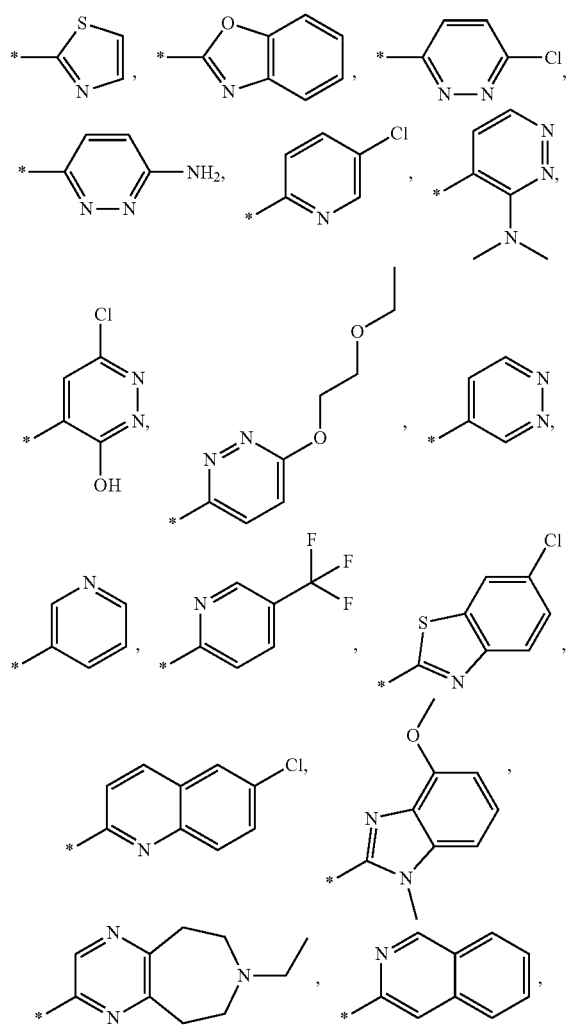

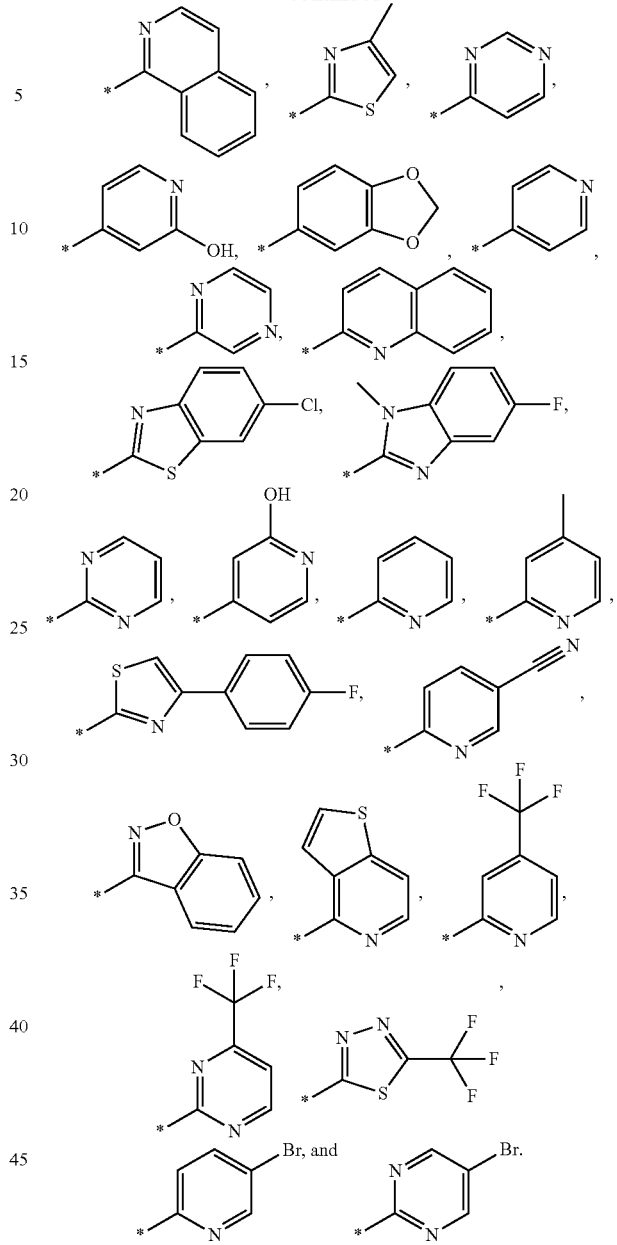

15. The drug combination according to claim 1, wherein the PDE4 inhibitor is selected from:

1.1 (3-fluorophenyl)-[5-oxo-2-(4-thiazol-2-yl-piperazin-1-yl)-6,7-dihydro-5H-5λ⁴ thieno[3,2-d]pyrimidin-4-yl]-amine 1.2 (R)-3-methyl-2-[5-oxo-2-(4-thiazol-2-yl-piperazin-1-yl)-6,7-dihydro-5H-5λ⁴ thieno[3,2-d]pyrimidin-4-ylamino]-butan-1-ol 1.3 [2-(4-benzoxazol-2-yl-piperazin-1-yl)-5-oxo-6,7-dihydro-5H-5λ⁴-thieno[3,2-d]pyrimidin-4-yl]-(3-fluorophenyl)-amine 1.3 [2-(4-benzoxazol-2-yl-piperazin-1-yl)-5-oxo-6,7-dihydro-5H-5λ⁴-thieno[3,2-d]pyrimidin-4-yl]-(3-fluorophenyl)-amine 1.4 [2-(4-benzoxazol-2-yl-piperazin-1-yl)-5-oxo-6,7-dihydro-5H-5λ⁴-thieno[3,2-d]pyrimidin-4-yl]-(tetrahydropyran-4-yl)-amine 1.5 (R)-2-{2-[4-(6-chloropyridazin-3-yl)-piperazin-1-yl]-5-oxo-6,7-dihydro-5H-5λ$^4$-thieno[3,2-d]pyrimidin-4-ylamino}-3-methylbutan-1-ol 1.6 {2-[4-(6-chloropyridazin-3-yl)-piperazin-1-yl]-5-oxo-6,7-dihydro-5H-5λ$^4$-thieno[3,2-d]pyrimidin-4-yl}-(3-fluorophenyl)-amine 1.7 (R)-2-[2-(4-benzoxazol-2-yl-piperazin-1-yl)-5-oxo-6,7-dihydro-5H-5λ$^4$-thieno[3,2-d]pyrimidin-4-ylamino]-3-methylbutan-1-ol 1.8 (1-{2-[4-(5-chloropyridin-2-yl)-piperazin-1-yl]-5-oxo-6,7-dihydro-5H-5λ$^4$-thieno[3,2-d]pyrimidin-4-ylamino}-cyclopropyl)-methanol 1.9 {2-[4-(5-chloropyridin-2-yl)-piperazin-1-yl]-5-oxo-6,7-dihydro-5H-5λ$^4$-thieno[3,2-d]pyrimidin-4-yl}-(tetrahydropyran-4-yl)-amine 1.10 {2-[4-(3-dimethylaminopyridazin-4-yl)-piperazin-1-yl]-5-oxo-6,7-dihydro-5H-5λ$^4$-thieno[3,2-d]pyrimidin-4-yl}-(3-fluorophenyl)-amine 1.11 6-chloro-4-{4-[4-(3-fluorophenylamino)-5-oxo-6,7-dihydro-5H-5λ$^4$-thieno[3,2-d]pyrimidin-2-yl]-piperazin-1-yl}-pyridazin-3-ol 1.12 2-{4-[6-(2-ethoxyethoxy)-pyridazin-3-yl]-piperazin-1-yl}-5-oxo-6,7-dihydro-5H-5λ$^4$-thieno[3,2-d]pyrimidin-4-yl)-(3-fluorophenyl)-amine 1.13 (3-fluorophenyl)-[5-oxo-2-(4-pyridazin-4-yl-piperazin-1-yl)-6,7-dihydro-5H-5λ$^4$-thieno[3,2-d]pyrimidin-4-yl]-amine 1.14 (R)-2-{2-[4-(4-methoxy-1-methyl-1H-benzimidazol-2-yl)-piperazin-1-yl]-5-oxo-6,7-dihydro-5H-5λ$^4$-thieno[3,2-d]pyrimidin-4-ylamino}-3-methylbutan-1-ol 1.15 (R)-2-{2-[4-(7-ethyl-6,7,8,9-tetrahydro-5H-pyrazino[2,3-d]azepin-2-yl)-piperazin-1-yl]-5-oxo-6,7-dihydro-5H-5λ$^4$-thieno[3,2-d]pyrimidin-4-ylamino}-3-methylbutan-1-ol 1.16 (R)-3-methyl-2-[5-oxo-2-(4-pyrimidin-4-yl-piperazin-1-yl)-6,7-dihydro-5H-5λ$^4$-thieno[3,2-d]pyrimidin-4-ylamino]-butan-1-ol 1.17 4-{4-[4-((R)-1-hydroxymethyl-2-methylpropylamino)-5-oxo-6,7-dihydro-5H-5λ$^4$-thieno[3,2-d]pyrimidin-2-yl]-piperazin-1-yl}-pyridin-2-ol 1.18 (R)-3-methyl-2-[5-oxo-2-(4-pyrimidin-4-yl-piperazin-1-yl)-6,7-dihydro-5H-5λ$^4$-thieno[3,2-d]pyrimidin-4-ylamino]-butan-1-ol 1.19 (R)-2-{2-[4-(3-dimethylaminopyridazin-4-yl)-piperazin-1-yl]-5-oxo-6,7-dihydro-5H-5λ$^4$-thieno[3,2-d]pyrimidin-4-ylamino}-3-methylbutan-1-ol 1.20 6-chloro-4-{4-[4-((R)-1-hydroxymethyl-2-methylpropylamino)-5-oxo-6,7-dihydro-5H-5λ$^4$-thieno[3,2-d]pyrimidin-2-yl]-piperazin-1-yl}-pyridazin-3-ol 1.21 (R)-2-(2-{4-[6-(2-ethoxyethoxy)-pyridazin-3-yl]-piperazin-1-yl}-5-oxo-6,7-dihydro-5H-5λ$^4$-thieno[3,2-d]pyrimidin-4-ylamino)-3-methylbutan-1-ol 1.22 (R)-3-methyl-2-[5-oxo-2-(4-pyridazin-4-yl-piperazin-1-yl)-6,7-dihydro-5H-5λ$^4$-thieno[3,2-d]pyrimidin-4-ylamino]-butan-1-ol 1.23 {1-[5-oxo-2-(4-pyrimidin-4-yl-piperazin-1-yl)-6,7-dihydro-5H-5λ$^4$-thieno[3,2-d]pyrimidin-4-ylamino]-cyclopropyl}-methanol 1.24 {1-[5-oxo-2-(4-pyridin-4-yl-piperazin-1-yl)-6,7-dihydro-5H-5λ$^4$-thieno[3,2-d]pyrimidin-4-ylamino]-cyclopropyl}-methanol 1.25 (S)-1-methyl-5-[5-oxo-2-(4-pyrimidin-4-yl-piperazin-1-yl)-6,7-dihydro-5H-5λ4-thieno[3,2-d]pyrimidin-4-ylamino]-piperidin-2-one 1.26 {2-[4-(5-fluoro-1-methyl-1H-benzoimidazol-2-yl)-piperazin-1-yl]-5-oxo-6,7-dihydro-5H-5λ4-thieno[3,2-d]pyrimidin-4-yl}-(tetrahydropyran-4-yl)-amine 1.27 [5-oxo-2-(4-pyridin-4-yl-piperazin-1-yl)-6,7-dihydro-5H-5)-4-thieno[3,2-d]pyrimidin-4-yl]-(tetrahydropyran-4-yl)-amine 1.28 (3-fluorophenyl)-{2-[4-(4-methoxy-1-methyl-1H-benzimidazol-2-yl)-piperazin-1-yl]-5-oxo-6,7-dihydro-5H-5λ4-thieno[3,2-d]pyrimidin-4-yl}-amine 1.29 {2-[4-(7-ethyl-6,7,8,9-tetrahydro-5H-pyrazino[2,3-d]azepin-2-yl)-piperazin-1-yl]-5-oxo-6,7-dihydro-5H-5λ4-thieno[3,2-d]pyrimidin-4-yl}-(3-fluorophenyl)-amine 1.30 (3-fluorophenyl)-[5-oxo-2-(4-pyrimidin-4-yl-piperazin-1-yl)-6,7-dihydro-5H-5λ4-thieno[3,2-d]pyrimidin-4-yl]-amine 1.31 4-{4-[4-(3-fluorophenylamino)-5-oxo-6,7-dihydro-5H-5λ4-thieno[3,2-d]pyrimidin-2-yl]-piperazin-1-yl}-pyridin-2-ol 1.32 (3-fluorophenyl)-[5-oxo-2-(4-pyridin-4-yl-piperazin-1-yl)-6,7-dihydro-5H-5λ4-thieno[3,2-d]pyrimidin-4-yl]-amine 1.33 (3-fluorophenyl)-(2-{4-[4-(4-fluorophenyl)-thiazol-2-yl]-piperazin-1-yl}-5-oxo-6,7-dihydro-5H-5λ4-thieno[3,2-d]pyrimidin-4-yl)-amine 1.34 [2-(4-benzo[d]isoxazol-3-yl-piperazin-1-yl)-5-oxo-6,7-dihydro-5H-5λ4-thieno[3,2-d]pyrimidin-4-yl]-(3-fluorophenyl)-amine 1.35 (R)-2-(2-{4-[4-(4-fluorophenyl)-thiazol-2-yl]-piperazin-1-yl}-5-oxo-6,7-dihydro-5H-5λ4-thieno[3,2-d]pyrimidin-4-ylamino)-3-methylbutan-1-ol 1.36 (R)-2-[2-(4-benzo[d]isoxazol-3-yl-piperazin-1-yl)-5-oxo-6,7-dihydro-5H-5λ$^4$-thieno[3,2-d]pyrimidin-4-ylamino]-3-methylbutan-1-ol.

16. The drug combination according to claim 1, wherein the NSAID is a COX 1-inhibitor or COX 2-inhibitor.

17. The drug combination according to claim 16, wherein the NSAID is selected from aceclofenac (2.1), acemetacin (2.2), acetylsalicylic acid (2.3), alclofenac (2.4), alminoprofen (2.5), amfenac (2.6), ampiroxicam (2.7), antolmetinguacil (2.8), anirolac (2.9), antrafenine (2.10), azapropazone (2.11), benorilate (2.12), bermoprofen (2.13), bindarit (2.14), bromfenac (2.15), bucloxinic acid (2.16), bucolom (2.17), bufexamac (2.18), bumadizone (2.19), butibufen (2.20), butixirate (2.21), carbasalate calcium (2.22), carprofen (2.23), choline magnesium trisalicylate (2.24), celecoxib (2.25), cinmetacin (2.26), cinnoxicam (2.27), clidanac (2.28), clobuzarit (2.29), deboxamet (2.30), dexibuprofen (2.31), dexketoprofen (2.32), diclofenac (2.33), diflunisal (2.34), droxicam (2.35), eltenac (2.36), enfenamic acid (2.37), etersalate (2.38), etodolac (2.39), etofenamat (2.40), etoricoxib (2.41), feclobuzon (2.42), felbinac (2.43), fenbufen (2.44), fenclofenac (2.45), fenoprofen (2.46), fentiazac (2.47), fepradinol (2.48), feprazone (2.49), flobufen (2.50), floctafenin (2.51), flufenamic acid (2.52), flufenisal (2.53), flunoxaprofen (2.54), flurbiprofen (2.55), flurbiprofenaxetil (2.56), furofenac (2.57), furprofen (2.58), glucametacin (2.59), ibufenac (2.60), ibuprofen (2.61), indobufen (2.62), indometacin (2.63), indometacinfarnesil (2.64), indoprofen (2.65), isoxepac (2.66), isoxicam (2.67), ketoprofen (2.68), ketorolac (2.69), lobenzarit (2.70), lonazolac (2.71), lornoxicam (2.72), loxoprofen (2.73), lumiracoxib (2.74), meclofenamic acid (2.75), meclofen, mefenamic acid (2.76), meloxicam (2.77), mesalazin (2.78), miroprofen (2.79), mofezolac (2.80), nabumetone (2.81), naproxen (2.82), nifluminic acid (2.83), olsalazine (2.84), oxaprozin (2.85), oxipinac (2.86), oxyphenbutazone (2.87), parecoxib (2.88), phenylbutazone (2.89), pelubiprofen (2.90), pimeprofen (2.91), pirazolac (2.92), priroxicam (2.93), pirprofen (2.94), pranoprofen (2.95), prifelon (2.96), prinomod (2.97), proglumetacin (2.98), proquazone (2.99), protizinic acid (2.100), rofecoxib (2.101), romazarit (2.102), salicylamide (2.103), salicylic acid (2.104), salmistein (2.105), salnacedin (2.106), salsalate (2.107), sulindac (2.108), sudoxicam (2.109), suprofen (2.110), talniflumat (2.111), tenidap (2.112), tenosal (2.113), tenoxicam (2.114), tepoxalin (2.115), tiaprofenic acid (2.116), taramide (2.117), tilnoprofenarbamel (2.118), timegadine (2.119), tinoridine (2.120), tiopinac (2.121), tolfenamic acid (2.122), tolmetin (2.123), ufenamate (2.124), valdecoxib (2.125), ximoprofen (2.126), zaltoprofen (2.127), and zoliprofen (2.128).

18. The drug combination according to claim 17, wherein the NSAID is selected from celecoxib (2.25), etoricoxib (2.41), lumiracoxib (2.74), parecoxib (2.88), rofecoxib (2.101), and valdecoxib (2.125).

19. The drug combination according to claim 18, wherein the NSAID is selected from acetylsalicylic acid (2.3), celecoxib (2.25), diclofenac (2.33), ibuprofen (2.61), indometacin (2.63), lumiracoxib (2.74), meloxicam (2.77), naproxen (2.82), and priroxicam (2.93).

20. The drug combination according to claim 19, wherein the NSAID is selected from acetylsalicylic acid (2.3), diclofenac (2.33), meloxicam (2.77), naproxen (2.82), and ibuprofen (2.61).

21. The drug combination according to claim 20, comprising the PDE4 inhibitor in a single dose of 0.01 mg to 50 mg.

22. The drug combination according to claim 21, wherein the NSAID comprises acetylsalicylic acid (2.3) in a single dose of 50 to 2000 mg, diclofenac (2.33) in a single dose of 25 mg to 150 mg, meloxicam (2.77) in a single dose of 7.5 mg to 30 mg, naproxen in a single dose of 250 to 1000 mg, or ibuprofen in a single dose of 200 to 2400 mg.

* * * * *